United States Patent
Cui et al.

(10) Patent No.: US 11,098,322 B2
(45) Date of Patent: *Aug. 24, 2021

(54) AAD-1 EVENT DAS-40278-9, RELATED TRANSGENIC CORN LINES, AND EVENT-SPECIFIC IDENTIFICATION THEREOF

(71) Applicant: DOW AGROSCIENCES LLC, Indianapolis, IN (US)

(72) Inventors: Yunxing Cory Cui, Cary, NC (US); Jill Bryan, Brownsburg, IN (US); Donald Maum, Champaign, IL (US); Greg Gilles, Alpharetta, GA (US); Terry Wright, Carmel, IN (US); Jennifer Hamilton, Indianapolis, IN (US); Nicole Arnold, Carmel, IN (US); Nathan VanOpdorp, Indianapolis, IN (US); Tina Kaiser, Carmel, IN (US); Ning Zhou, Kaunakakai, HI (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 96 days.

This patent is subject to a terminal disclaimer.

(21) Appl. No.: 16/279,055

(22) Filed: Feb. 19, 2019

(65) Prior Publication Data
US 2019/0233904 A1    Aug. 1, 2019

Related U.S. Application Data

(60) Continuation of application No. 14/989,787, filed on Jan. 6, 2016, now Pat. No. 10,323,287, which is a division of application No. 13/390,969, filed as application No. PCT/US2010/045869 on Aug. 18, 2010, now Pat. No. 9,402,358.

(60) Provisional application No. 61/235,248, filed on Aug. 19, 2009.

(51) Int. Cl.
*C12N 15/82* (2006.01)
*C12Q 1/6895* (2018.01)
*C12N 9/02* (2006.01)

(52) U.S. Cl.
CPC ....... *C12N 15/8274* (2013.01); *C12N 9/0069* (2013.01); *C12N 9/0071* (2013.01); *C12Q 1/6895* (2013.01); *C12Q 2600/16* (2013.01); *C12Y 113/00* (2013.01)

(58) Field of Classification Search
CPC ................................................ C12N 15/8274
See application file for complete search history.

(56) References Cited

U.S. PATENT DOCUMENTS

| | | | |
|---|---|---|---|
| 5,770,212 A | 6/1998 | Falkner et al. | |
| 6,069,298 A | 5/2000 | Gengenbach et al. | |
| 7,323,556 B2 | 1/2008 | Bing et al. | |
| 7,745,391 B2 | 6/2010 | Mintz et al. | |
| 7,838,733 B2 | 11/2010 | Wright et al. | |
| 7,960,612 B2 | 6/2011 | Zhang et al. | |
| 8,106,169 B2 | 1/2012 | Briggs et al. | |
| 9,127,289 B2 | 9/2015 | Wright et al. | |
| 10,174,337 B2 | 1/2019 | Wright et al. | |
| 2004/0031072 A1 | 2/2004 | La Rosa et al. | |
| 2004/0034888 A1 | 2/2004 | Liu et al. | |
| 2005/0223430 A1 | 10/2005 | Bakker et al. | |
| 2007/0089201 A1* | 4/2007 | Briggs .................. | C07K 16/00 800/288 |
| 2007/0092871 A1 | 4/2007 | Lodes et al. | |
| 2008/0028485 A1* | 1/2008 | Whitehead .............. | A01H 5/10 800/278 |
| 2008/0083042 A1 | 4/2008 | Butruille et al. | |
| 2008/0311096 A1 | 12/2008 | Lang et al. | |
| 2009/0093366 A1 | 4/2009 | Wright et al. | |
| 2011/0289620 A1 | 11/2011 | Cui et al. | |
| 2012/0220460 A1 | 8/2012 | Hanger et al. | |
| 2012/0222153 A1 | 8/2012 | Cui et al. | |

FOREIGN PATENT DOCUMENTS

| | | |
|---|---|---|
| JP | 2007-513641 | 5/2007 |
| JP | 2010-512153 | 4/2010 |
| JP | 2010-526535 | 8/2010 |
| JP | 2013-505706 | 2/2013 |
| RU | 2187555 | 8/2008 |

(Continued)

OTHER PUBLICATIONS

Spencer et al, Plant Molecular Biology (1992) 18:201-210.*

(Continued)

*Primary Examiner* — Mykola V. Kovalenko
(74) *Attorney, Agent, or Firm* — Barnes & Thornburg LLP

(57) ABSTRACT

This invention relates in part to plant breeding and herbicide tolerant plants. This invention includes a novel aad-1 transformation event in corn plants comprising a polynucleotide sequence, as described herein, inserted into a specific site within the genome of a corn cell. In some embodiments, said event/polynucleotide sequence can be "stacked" with other traits, including, for example, other herbicide tolerance gene(s) and/or insect-inhibitory proteins. Additionally, the subject invention provides assays for detecting the presence of the subject event in a sample (or corn grain, for example). The assays can be based on the DNA sequence of the recombinant construct, inserted into the corn genome, and on the genomic sequences flanking the insertion site. Kits and conditions useful in conducting the assays are also provided.

1 Claim, 7 Drawing Sheets

Specification includes a Sequence Listing.

(56) References Cited

FOREIGN PATENT DOCUMENTS

| WO | WO 1996/031609 | 10/1996 |
|---|---|---|
| WO | 03/024227 | 3/2003 |
| WO | WO 2005/059103 | 6/2005 |
| WO | WO 2005/107437 | 11/2005 |
| WO | WO 2007/101273 | 9/2007 |
| WO | WO 2007/106407 | 9/2007 |
| WO | WO 2007/053482 | 10/2007 |
| WO | WO 2008/021207 | 2/2008 |
| WO | WO 2008/141154 | 11/2008 |
| WO | WO 2008/143993 | 11/2008 |
| WO | WO 2010/077319 | 7/2010 |
| WO | WO 2011/022469 | 2/2011 |
| WO | WO 2011/022470 | 2/2011 |
| WO | WO 2012/094555 | 7/2012 |

OTHER PUBLICATIONS

GM Crops, 2010, vol. 1(5), pp. 294-311.
Chander et al, "Genetic dissection of tocopherol content and composition in maize grain using quantitative trait loci analysis and the candidate gene approach," Molecular Breeding, Apr. 12, 2008, 353-365, vol. 22, Issue 3.
Corn Growth Stage Day and GDU Calendar 10.
Database EMBL [Online] Mar. 25, 2005 (Mar. 25, 2005), "ZMMBF0071 J08f ZMMBF *Zea mays* genomic clone ZMMBF0071 J08 5', genomic survey sequence.", retrieved from EBI accession No. EM GSS:CZ299402 Database accession No. CZ299402.
Database EMBL [Online] Oct. 18, 2000 (Oct. 18, 2000), "CIT-HSP-2021 P24.TFB CIT-HSP *Homo sapiens* genomic clone 2021 P24, DNA sequence.", EPO Form 2906 01.91 TRI retrieved from EBI accession No. EM GSS:AZ515693 Database accession No. AZ515693.
EMBL entry AC177898, Aug. 26, 2006, available at <http://www.ebi.ac.uk/ena/data/view/AC177898>.
EMBL entry AC212814 Oct. 29, 2007 (Oct. 29, 2007).
EMBL, entry AC193348, Apr. 20, 2008, available at <http://www.ebi.ac.uk/ana/data/view/AC193348>.
Fourgoux-Nicol et al, Isolation of Rapeseed Genes Expressed Early and Specifically During Development of the Male Gametophyte, Plant Mol. Biol. (1999) 40:857-872.
Frankel et al., "Characterization of diphtheria fusion proteins targeted to the human interleukin-3 receptor, Protein Eng," 13(3): 575-581 (2000).
GenBank Accession DQ141598—*Zea mays* cultivar Nongda 105 polyubiquitin-1 (Ubi-1) gene, promoter region and 5' UTR—Sep. 6, 2005.
GenBank Accession DQ469641—Transformation vector pYW310, complete sequence—Jun. 30, 2007.
GenBank Accession No. DT773202, published Sep. 14, 2005.
GenBank Accession No. DT773202.1, published Sep. 14, 2005.
GenBank Accession No. FT392126.1, submitted by Nakamura et al, on Jul. 27, 2010.
GenBank. Accession AR014675—Sequence 1 from patent U.S. Pat. No. 5773695—Dec. 5, 1998.
GenBank. Accession AR157937—Sequence 20 from patent U.S. Pat. No. 6,245,974—Oct. 17, 2001.
GenBank. Accession AX417132—Sequence 9 from patent WO02/20811—Jun. 14, 2002.
GenBank. Accession AX840288—Sequence 10 from patent WO03/078614—Dec. 16, 2003.
GenBank. Accession AX840289—Sequence 11 from Patent WO03/078614—Dec. 16, 2003.
GenBank. Accession AY178047—Expression vector pYPX143, complete sequence—Dec. 6, 2006.
GenBank. Accession AY178048—Expression vector pYPX145, complete sequence—Nov. 16, 2006.
GenBank. Accession AY178049—Expression vector pYPX245, complete sequence—Dec. 6, 2006.
GenBank. Accession BD058093—Improved SAR plant transformation process—Nov. 17, 2009.
GenBank. Accession BT060890—*Zea mays* full-length cDNA clone ZM_BFb0066G16 mRNA, complete cds—Feb. 21, 2009.
GenBank. Accession DD239963—GNTIII expression in plants—Apr. 26, 2006.
GenBank. Accession DD239964—GNTIII expression in plants—Apr. 26, 2006.
GenBank. Accession DD406929—Plant production of immunoglobulins with reduced fucosylation—Feb. 21, 2007.
GenBank. Accession DD406930—Plant production of immunoglobulins with reduced fucosylation—Feb. 21, 2007.
GenBank. Accession DD406931—Plant production of immunoglobulins with reduced fucosylation—Feb. 21, 2007.
GenBank. Accession DI000194—GNTIII expression in plants—Feb. 21, 2008.
GenBank. Accession DI000700—GNTIII expression in plants—Feb. 21, 2008.
GenBank. Accession DM036186—Anti-T Cell and Autoantigen Treatment of Autoimmune Disease—Feb. 27, 2009.
GenBank. Accession DM036191—Anti-T Cell and Autoantigen Treatment of Autoimmune Disease—Feb. 27, 2009.
GenBank. Accession EU161574—Binary vector pIPKb008, complete sequence—Dec. 7, 2007.
GenBank. Accession EU947402—*Zea mays* clone 342363 mRNA sequence—Oct. 30, 2008.
GenBank. Accession FJ750579—Cre-lox Univector acceptor vector pCR703, complete sequence—Jul. 13, 2009.
GenBank. Accession GN362809—Sequence 2 from Patent WO09/046384—May 12, 2009.
GenBank. Accession GP673705—Sequence 81709 from patent U.S. Pat. No. 7,560,542—Sep. 28, 2009.
GenBank. Accession U67919—Nicotiana tabacum Rb7 matrix attachment region/scaffold attachment region sequence—Feb. 7, 2005.
GenBank. Accession XM_002447175—Sorghum bicolor hypothetical protein, mRNA Jul. 13, 2009.
Guo et al., "Protein tolerance to random amino acid change." Proceedings of the National Academy of Sciences of the United States of America 101.25 (2004): 9205-9210.
Hake et al., Report from "The Maize Genetics Executive Committee," 2007, esp: UMC1265 and MMC0111 p. 79 first column.
Herman et al., "Compositional safety of event DAS-40278-9 (AAD-1) herbicide-tolerant maize," GM Crops, Nov./Dec. 2010, 1-18 (294-311), 1(5).
Japan Biosafety Clearing House (J-BCH). Maize tolerant to aryloxyalkanoate herbicide (Modified aad-1, *Zea mays* subsp. mays), [online] Jul. 30, 2009 (retrieved Jul. 29, 2014), Available on the internet: <URL: http://www.bch.biodic.go.jp/english/lmo_2009.html> & <URL: http://www.bch.biodic.go.jp/download/en_lmo/DAS40278enUR.pdf.
Matzke et al., "Position effects and epigenetic silencing of plant transgenes," Apr. 1, 1998, 142-148, vol. 1, Issue 2.
Pakula et al., "Genetic analysis of protein stability and function," Anna. Rev. Genet., 23: 289-310 (1989).
Product label of the herbicide composition WEEDAR®-64 by Nufarm Americas Inc—USA, available to public on or before Jul. 14, 2007.
Rang et al., "Competition of Bacillus thuringiensis Cry1 toxins for midgut binding sites: a basis for the development and management of transgenic tropical maize resistant to several stemborers," *Curr. Microbiol.*, 49(1): 22-27 (2004).
Sauka et al., "Bacillus thuringiensis: generalidades: Un acercamiento a su empleo en el biocontrol de insectos lepidopteros que son plagas agrícolas," Revista Argentina De Microbiologia, 40: 124-140 (2008).
Summary of the written application of aryloxyalkanoate herbicide-resistant corn plant (modified aad-1, *Zea mays*subsp. mays (L.)Iltis.) (DAS40278, OECD UI: DAS-40278-9), pp. 1-25, [online], Jun. 12, 2009, Ministry of the Environment (in Japanese), [searched on Nov. 26, 2014], Internet <URL: http://www.env.go.jp/press/file_view.php?serial=13699&hou_id=11233>.
Swiecicka et al., "Novel isolate of *Bacillus thuringiensis* subsp. thuringiensis that produces a quasicuboidal crystal of Cry1Ab21 toxic to larvae of Trichoplusia ni.," *Appl. Environ. Microbiol.*, 74(4): 923-930 (2008).

(56) References Cited

OTHER PUBLICATIONS

Zhang et al., "Mapping quantitative trait loci for oil, starch, and protein concentrations in grain with high-oil maize by SSR markers," Aug. 3, 2007, 335-344, vol. 162, Issue 3.

* cited by examiner

DAS-40278-9 Insert

5' End Border
SEQ ID NO: 34      ACAGCACCGT  *ACCTTGAAGCGGAATACAATG*————

Original Locus
SEQ ID NO: 35      ACAGCACCGT  CC

DAS-40278-9 Insert

3' End Border
SEQ ID NO: 36      ————*T*  TACCCAAAAGCACCGCAAGGGGTAGCCCTGG

Original Locus
SEQ ID NO: 37              TACCCAAAAGCACCGCAAGGGGTAGCCCTGG

Fig. 6

SEQUENCE LISTING

<160> NUMBER OF SEQ ID NOS: 37

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
tgcactgcag gtcgactcta gaggat            26

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gcggtggcca ctattttcag aag                                    23

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ttgttacggc atatatccaa tagcgg                                 26

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
ccgtggccta ttttcagaag aagttc                                 26

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
acaaccatat tggctttggc tga                                    23

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
cctgttgtca aaatactcaa ttgtcctt                               28

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
ctccattcag gagacctcgc ttg                                    23

<210> SEQ ID NO 8
<211> LENGTH: 23
<212> TYPE: DNA
<213> ORGANISM: Artificial Sequence
<220> FEATURE:

<223> OTHER INFORMATION: Primer

<400> SEQUENCE: 8
gtacaggtcg catccgtgta cga                                    23

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
ccccccctct ctaccttctc tagat                                  25

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gtcatgccct caattctctg aca                                    23

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gtcgcttcag caacacctca gtc                                    23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
agctcagatc aaagacacac ccc                                    23

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
tcgtttgact aatttttcgt tgatgtac                               28

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tctcactttc gtgtcatcgg tcg                                    23

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
ccagcacgaa ccattga                                                17

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
cgtgtatata aggtccagag ggta                                        24

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
ttgggagaga gggctga                                                17

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tggtaagtgt ggaaggcatc                                             20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gaggtacaac cggagcgttt                                             20

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
ccgacgcttt tctggagta                                              19

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tgtgccacat aatcacgtaa ca                                    22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gagacgtatg cgaaaattcg                                       20

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ttgcttcagt tcctctatga gc                                    22

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
tccgtgtcca ctcctttgt                                        19

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
gcaaaggaaa actgccattc tt                                    22

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tctctaagcg gcccaaactt                                       20

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
attctggctt tgctgtaaat cgt                                   23

<210> SEQ ID NO 28
<211> LENGTH: 24

```
<212> TYPE: DNA
<213> ORGANISM: Artificial Sequence
<220> FEATURE:
<223> OTHER INFORMATION: Primer

<400> SEQUENCE: 28
ttacaatcaa cagcaccgta cctt                                           24

<210> SEQ ID NO 29
<211> LENGTH: 8557
<212> TYPE: DNA
<213> ORGANISM: Artificial Sequence
<220> FEATURE:
<223> OTHER INFORMATION: Insert and Flanking Sequences for Event DAS-
      40278-9

<400> SEQUENCE: 29
actggtattt aatatacttt aataaatatt attagattcc tcgtcaaaga acttttttaca    60 atatatctat ttagaatcat atatgtcata gttttttttc taagagtcta gtttactagt   120
aaaatccgac tcacattttt cgaacttggg atgcaacact taaatagtac aaaaccttgg   180
tatgcagtat tttacattgt aagattcaaa atttctaaag cagtatatat atgtttccag   240
aaacttatag atatagaaaa aacagagaga cgtatgcgaa aattcgataa aggtgtacat   300
tggattcgca aggctaaata catatttatc gtggatccat gcagagtttg gtaataaaa    360 ttagatactt ccaatcatgt gccacataat cacgtaacat tagtaattta aatgacatta   420
ccatgtccaa ctgatttaaa acacaaactc ttcttgaacc atatagtttg acaaaccaaa   480
tatatataac tggagctact agttatgaat caattaaaaa ttactttgaa gattcaacgt   540
agtgccagtt tggctctagc acatctaacc agaagggcta aggctggctt caacaggaac   600
agccaaatcc gagatcgagc catttgccat ttttgggtag ttagtttaac tttcatatat   660
cttcccatcc ttttttgcct agcctaaatg ctttgatgt tgaagaccat attaatttgc    720
ttcagtggca ctaggacaac catattggct ttggctgacc cgttagagtt agcctaatgg   780
gtggaagggg agggaagggg aggatcgatg gtggcatgag agaggggttg acgatcacga   840
tgatgatgcg agtgaggagg agaggtggc gacgacacag gggagaaagg agagggacgc    900
taggagcgtc aagggcgtgg gggaggggag ggtcggaggg atgaaggatg acctaaatat   960
tattgttgag tgatagaggg ttattcaact atccgacccg tcgattttga tggtatgtta  1020
aatttgtgtg tcatttgttt gatggattta gtaaaggtta tgggtctaga ggtgattttt  1080
gttgggtggg tttacagag tttaaactag cggattatat agtggtatag aagatatagt   1140
tttattagaa catctccaaa atgtgactcg aaataatacc cccaaaattt aaaatactac  1200
atcattttga taaaaaggt aaagtagagc actgttggaa cagttttttaa aagttgtgcc   1260 ctatattta aaatagggta ctgatttaaa atattgttgt gggggataga tatccccggg   1320
tccactagaa ggcgagaagg cctcgcgtgt ggccacgggc cagttacccc gcaaggccat  1380
cccttcgtgg gtcgagctag aattactggt agaatgggct gaccgaagaa ggcaacagac  1440
tcgagcccaa acaatccatc ggctcgtgcg ctatccacag aaactacccg actttccggc  1500
gcatggcatc ctagaatatc ggggcgtatt agggatgagt cagcgagatt tcggaagat   1560 tagttcagtt tgttcgctat tatttaggag acatatgatc ctcatgtacg tatggagtgc  1620
cccacggtcg tgtatataag gtccagaggg taccccatca tttctatcga ccatctacct  1680
atctcatcag ctttttctcca ttcaggagac ctcgcttgta acccaccaca tatagatcca  1740
tcccaagaag tagtgtatta cgcctctcta agcggcccaa acttgcagaa aaccgcctat  1800
```

```
ccctctctcg tgcgtccagc acgaaccatt gagttacaat caacagcacc gtaccttgaa    1860
gcggaataca atgaaggtta gctacgattt acagcaaagc cagaatacaa tgaaccataa    1920
agtgattgaa gctcgaaata tacgaaggaa caaatatttt taaaaaaata cgcaatgact    1980
tggaacaaaa gaaagtgata tatttttttgt tcttaaacaa gcatcccctc taaagaatgg   2040
cagtttttcct ttgcatgtaa ctattatgct cccttcgtta caaaaatttt ggactactat   2100
tgggaacttc ttctgaaaat agtggccacc gcttaattaa ggcgcgccat gcccgggcaa    2160
gcggccgctt aattaaattt aaatgtttaa actaggaaat ccaagcttgc atgcctgcag    2220
atccccgggg atcctctaga gtcgacctgc agtgcagcgt gacccggtcg tgcccctctc    2280
tagagataat gagcattgca tgtctaagtt ataaaaaatt accacatatt ttttttgtca    2340
cacttgtttg aagtgcagtt tatctatctt tatacatata tttaaacttt actctacgaa    2400
taatataatc tatagtacta caataatatc agtgttttag agaatcatat aaatgaacag    2460
ttagacatgg tctaaaggac aattgagtat tttgacaaca ggactctaca gttttatctt    2520
tttagtgtgc atgtgttctc ctttttttttt gcaaatagct tcacctatat aatacttcat   2580
ccattttatt agtacatcca tttagggttt agggttaatg gttttttatag actaattttt    2640
ttagtacatc tattttattc tattttagcc tctaaattaa gaaaactaaa actctatttt    2700
agttttttta tttaatagtt tagatataaa atagaataaa ataaagtgac taaaaattaa    2760
acaaataccc tttaagaaat taaaaaaact aaggaaacat ttttcttgtt tcgagtagat    2820
aatgccagcc tgttaaacgc cgtcgacgag tctaacggac accaaccagc gaaccagcag    2880
cgtcgcgtcg ggccaagcga agcagacggc acggcatctc tgtcgctgcc tctggacccc    2940
tctcgagagt tccgctccac cgttggactt gctccgctgt cggcatccag aaattgcgtg    3000
gcggagcggc agacgtgagc cggcacggca ggcggcctcc tcctcctctc acggcaccgg    3060
cagctacggg ggattccttt cccaccgctc cttcgctttc ccttcctcgc cgccgtaat    3120
aaatagacac cccctccaca ccctctttcc ccaacctcgt gttgttcgga gcgcacacac    3180
acacaaccag atctccccca aatccacccg tcggcacctc cgcttcaagg tacgccgctc    3240
gtcctccccc cccccccccc tctctacctt ctctagatcg gcgttccggt ccatgcatgg    3300
ttagggcccg gtagttctac ttctgttcat gtttgtgtta gatccgtgtt tgtgttagat    3360
ccgtgctgct agcgttcgta cacgatgcg acctgtacgt cagacacgtt ctgattgcta    3420
acttgccagt gtttctcttt ggggaatcct gggatggctc tagccgttcc gcagacggga    3480
tcgatttcat gattttttttt gtttcgttgc atagggtttg gtttgccctt ttcctttatt    3540
tcaatatatg ccgtgcactt gtttgtcggg tcatcttttc atgcttttttt ttgtcttggt    3600
tgtgatgatg tggtctggtt gggcggtcgt tctagatcgg agtagaattc tgtttcaaac    3660
tacctggtgg atttattaat tttggatctg tatgtgtgtg ccatacatat tcatagttac    3720
gaattgaaga tgatggatgg aaatatcgat ctaggatagg tatacatgtt gatgcgggtt    3780
ttactgatgc atatacagag atgctttttg ttcgcttggt tgtgatgatg tggtgtggtt    3840
gggcggtcgt tcattcgttc tagatcggag tagaatactg tttcaaacta cctggtgtat    3900
ttattaattt tggaactgta tgtgtgtgtc atacatcttc atagttacga gtttaagatg    3960
gatggaaata tcgatctagg ataggtatac atgttgatgt gggttttact gatgcatata    4020
catgatggca tatgcagcat ctattcatat gctctaacct tgagtaccta tctattataa    4080
taaacaagta tgttttataa ttatttcgat cttgatatac ttggatgatg gcatatgcag    4140
```

```
cagctatatg tggattttttt tagccctgcc ttcatacgct atttatttgc ttggtactgt    4200
ttcttttgtc gatgctcacc ctgttgtttg gtgttacttc tgcagggtac ccccgggtc     4260 gaccatggct catgctgccc tcagccctct ctcccaacgc tttgagagaa tagctgtcca    4320
gccactcact ggtgtccttg gtgctgagat cactggagtg gacttgaggg aaccacttga    4380
tgacagcacc tggaatgaga tattggatgc cttccacact taccaagtca tctactttcc    4440
tggccaagca atcaccaatg agcagcacat tgcattctca agaaggtttg gaccagttga    4500
tccagtgcct cttctcaaga gcattgaagg ctatccagag gttcagatga tccgcagaga    4560
agccaatgag tctggaaggg tgattggtga tgactggcac acagactcca ctttccttga    4620
tgcacctcca gctgctgttg tgatgagggc catagatgtt cctgagcatg gcggagacac    4680
tgggttcctt tcaatgtaca cagcttggga gaccttgtct ccaaccatgc aagccaccat    4740
cgaagggctc aacgttgtgc actctgccac acgtgtgttc ggttccctct accaagcaca    4800
gaaccgtcgc ttcagcaaca cctcagtcaa ggtgatggat gttgatgctg gtgacagaga    4860
gacagtccat cccttggttg tgactcatcc tggctctgga aggaaaggcc tttatgtgaa    4920
tcaagtctac tgtcagagaa ttgagggcat gacagatgca gaatcaaagc cattgcttca    4980
gttcctctat gagcatgcca ccagatttga cttcacttgc cgtgtgaggt ggaagaaaga    5040
ccaagtcctt gtctgggaca acttgtgcac catgcaccgt gctgttcctg actatgctgg    5100
caagttcaga tacttgactc gcaccacagt tggtggagtt aggcctgccc gctgagtagt    5160
tagcttaatc acctagagct cgtttaaact gagggcactg aagtcgcttg acgtgctgaa    5220
ttgtttgtga tgttggtggc gtattttgtt taaataagta agcatggctg tgattttatc    5280
atatgatcga tctttggggt tttatttaac acattgtaaa atgtgtatct attaataact    5340
caatgtataa gatgtgttca ttcttcggtt gccatagatc tgcttatttg acctgtgatg    5400
ttttgactcc aaaaaccaaa atcacaactc aataaactca tggaatatgt ccacctgttt    5460
cttgaagagt tcatctacca ttccagttgg catttatcag tgttgcagcg gcgctgtgct    5520
ttgtaacata acaattgtta cggcatatat ccaatagcgg ccggcctcct gcagggttta    5580
aacttgccgt ggcctatttt cagaagaagt tcccaatagt agtccaaaat ttttgtaacg    5640
aagggagcat aatagttaca tgcaaaggaa aactgccatt ctttagaggg gatgcttgtt    5700
taagaacaaa aaatatatca ctttcttttg ttccaagtca ttgcgtattt ttttaaaaat    5760
atttgttcct tcgtatattt cgagcttcaa tcactttatg gttctttgta ttctggcttt    5820
gctgtaaatc gtagctaacc ttcttcctag cagaaattat taatacttgg gatattttt     5880 tagaatcaag taaattacat attaccacca catcgagctg cttttaaatt catattacag    5940
ccatataggc ttgattcatt ttgcaaaatt tccaggatat tgacaacgtt aacttaataa    6000
tatcttgaaa tattaaagct attatgatta ggggtgcaaa tggaccgagt tggttcggtt    6060
tatatcaaaa tcaaaccaaa ccaactatat cggtttggat tggttcggtt ttgccgggtt    6120 ttcagcatt tctggttttt tttttgttag atgaatatta ttttaatctt actttgtcaa     6180 attttgata agtaaatata tgtgttagta aaaattaatt tttttacaa acatatgatc      6240 tattaaaata ttcttatagg agaattttct taataacaca tgatatttat ttattttagt    6300
cgtttgacta atttttcgtt gatgtacact ttcaaagtta accaaattta gtaattaagt    6360
ataaaaatca atatgatacc taaataatga tatgttctat ttaatttaa attatcgaaa     6420 tttcacttca aattcgaaaa agatatataa gaattttgat agattttgac atatgaatat    6480
ggaagaacaa agagattgac gcattttagt aacacttgat aagaaagtga tcgtacaacc    6540
```

```
aattatttaa agttaataaa aatggagcac ttcatattta acgaaatatt acatgccaga    6600
agagtcgcaa atatttctag atattttta aagaaaattc tataaaaagt cttaaaggca    6660
tatatataaa aactatatat ttatattttt tacccaaaag caccgcaagg ggtagccctg    6720
ggtgtgcgga cggactctaa acaccgacag ctggcgcgcc aggtaggggg tgtgtctttg    6780
atctgagcta gctcaatgac cattacctcc aaatgcaaga tcgcccttcg ccccgggact    6840
atgttttgct ttggaaccat ctcatccata gcagatgaag agggaactct gcaccgcata    6900
gcagatctat tggagaagaa gctttcctca gaaatctcga ggggagccag ggcagaacag    6960
cgggtggcac catcacccgc acctcaagcg aagatgacct cttacaaacc gaaagtcggg    7020
agctcaccta cccgaaaaac tccgctgtcc acttcgccca caaggagtg gacacggatt    7080 actcgaaaga aggaagcgag tgtcccgagt caggggacgg gaacacgcca agccatctt    7140 ccgacgcctt cgccctcaaa tgaggatgga aagaagagcg ccatcgcgct ggctcctttc    7200
taccccgacg tcctcttcat caggggggaga ttggagttag cacccgtctt caacgatgag    7260
ccaaccatgc aaggggaaga gcctccccag cgtgaggcgc gacgacggag gaatagaagc    7320
cagaacgtgc ggcgacatca cgaggctggg gaacgggatc cggcgcaacc cgtatcccgg    7380
gacgaagctt tagaagtagg aaaaactccc gacgagtggg tacaccgaga aaggcggaac    7440
tctcgccgcc gtgatcgccg acaagcttag gaccgagaac gagagcaagc cgagcaaggt    7500
gcaaggctgc gccgagagaa tgctctcttt gctcggaacc tgtaccccga cttcgctcgt    7560
gcaatgaaca cgccgagtga agtcggaggg gtactggccc agatagctga cggcctcccg    7620
cgaaccctag acacggaagg ctaccggcgg ctgcttactc gagcagttaa tcaccttcta    7680
cccatcacta atcctccaag cgacctacgc catgccatca acagccggcg agacacgcgg    7740
agctccatca acgcttcgcg cgaccgatga cacgaaagtg agatagggaa ccgagaggag    7800
tatgtccgag atcatgccat cctggcatga agtcatgcca cccgagctga gtcggttgcg    7860
gcctcgacca gtgtcccgtt ccaggacga tcaagatgac acacaactgg ctccccctcct    7920 tgggaccgac ctcacgaacg ccgacatgaa gacacgtgcg gagtcttcgc acttactccg    7980
tgtctccggg ccatccagtg gcccctaact tcaaggtctc caacgtcagc aagtatgagc    8040
gcaagcagga cctgggtggc tggttagcca tctacacgat tgtcacatgg gccgccggag    8100
cgacggagga cgtgatgaca gtgtattttc ccattgtcct agggcaagac gcaatgcagt    8160
ggctccgaca tctaccccaa cattgcatag acaattggag cgacttcagt tggtgcttca    8220
tcgccaactt ccagtccctc tttgacaagc cggcgcagcc atgggaccta aaatccattg    8280
ggcatcaggg cgatgaaacg ctccggttgt acctcaagag gttttagacc atgaggaacc    8340 acaccccga agtcgccgag gcggggtga ttgaagactt ctaccgagga tccaatgact    8400
cggctttcgt ccgagccata ctccagaaaa gcgtcggcca cctccgaaca cttgttccgg    8460
gaggcagacc tctacatcac cacgattaa cgggccagg acctcatcgg aggcacgaaa    8520
gccgcgccac acgcgccacg gtgtgacacg aaccagc                           8557
```

<210> SEQ ID NO 30
<211> LENGTH: 23
<212> TYPE: DNA
<213> ORGANISM: Artificial Sequence
<220> FEATURE:
<223> OTHER INFORMATION: Primer for Flanking Marker

<400> SEQUENCE: 30

-continued

```
gcctagtcgc ctaccctacc aat                                             23

<210> SEQ ID NO 31
<211> LENGTH: 24
<212> TYPE: DNA
<213> ORGANISM: Artificial Sequence
<220> FEATURE:
<223> OTHER INFORMATION: Primer for Flanking Marker

<400> SEQUENCE: 31
tgtgttcttg attgggtgag acat                                            24

<210> SEQ ID NO 32
<211> LENGTH: 21
<212> TYPE: DNA
<213> ORGANISM: Artificial Sequence
<220> FEATURE:
<223> OTHER INFORMATION: Primer for Flanking Marker

<400> SEQUENCE: 32
tactggggat tagagcagaa g                                               21

<210> SEQ ID NO 33
<211> LENGTH: 21
<212> TYPE: DNA
<213> ORGANISM: Artificial Sequence
<220> FEATURE:
<223> OTHER INFORMATION: Primer for Flanking Marker

<400> SEQUENCE: 33
aatctatgtg tgaacagcag c                                               21

<210> SEQ ID NO 34
<211> LENGTH: 31
<212> TYPE: DNA
<213> ORGANISM: artificial sequence
<220> FEATURE:
<223> OTHER INFORMATION: 5' end border with DAS-40278-9 Insert

<400> SEQUENCE: 34
acagcaccgt accttgaagc ggaatacaat g                                    31

<210> SEQ ID NO 35
<211> LENGTH: 12
<212> TYPE: DNA
<213> ORGANISM: artificial sequence
<220> FEATURE:
<223> OTHER INFORMATION: 5' original locus

<400> SEQUENCE: 35
acagcaccgt cc                                                         12

<210> SEQ ID NO 36
<211> LENGTH: 32
<212> TYPE: DNA
<213> ORGANISM: artificial sequence
<220> FEATURE:
<223> OTHER INFORMATION: 3' end border with DAS-40278-9 Insert

<400> SEQUENCE: 36
ttacccaaaa gcaccgcaag gggtagccct gg                                   32

<210> SEQ ID NO 37
<211> LENGTH: 31
<212> TYPE: DNA
<213> ORGANISM: artificial sequence
```

```
<220> FEATURE:
<223> OTHER INFORMATION: 3' original locus

<400> SEQUENCE: 37
tacccaaaag caccgcaagg ggtagccctg g                             31
```

AAD-1 EVENT DAS-40278-9, RELATED TRANSGENIC CORN LINES, AND EVENT-SPECIFIC IDENTIFICATION THEREOF

CROSS REFERENCE TO RELATED APPLICATIONS

This application is a continuation of U.S. application Ser. No. 14/989,787, filed Jan. 6, 2016 (now U.S. Pat. No. 10,323,287), which is a divisional of U.S. application Ser. No. 13/390,969, filed May 7, 2012 (now U.S. Pat. No. 9,402,358), which is a national stage entry of PCT/US2010/045869, filed Aug. 18, 2010 which claims priority to U.S. Provisional Patent Application No. 61/235,248, filed on Aug. 19, 2009, the disclosures of which are each incorporated by reference in their entirety into the present application.

INCORPORATION BY REFERENCE OF MATERIAL SUBMITTED ELECTRONICALLY

Incorporated by reference in its entirety is a computer-readable nucleotide/amino acid sequence listing submitted concurrently herewith as an 18 kilobyte ASCII (Text) file named "291670_ST25.txt", created on Feb. 19, 2019.

BACKGROUND OF THE INVENTION

The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides and may be used as a selectable marker during plant transformation and in breeding nurseries. The aad-1 gene, itself, for herbicide tolerance in plants was first disclosed in WO 2005/107437 (see also US 2009-0093366).

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., Ann. Rev. Genet. 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgres sing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

U.S. Patent Apps. 20020120964 A1 and 20040009504 A1 relate to cotton event PV-GHGT07(1445) and compositions and methods for the detection thereof. WO 02/100163 relates to cotton event MON15985 and compositions and methods for the detection thereof. WO 2004/011601 relates to corn event MON863 plants and compositions and methods for the detection thereof. WO 2004/072235 relates to cotton event MON 88913 and compositions and methods for the detection thereof.

WO 2006/098952 relates to corn event 3272. WO 2007/142840 relates to corn event M1R162.

U.S. Pat. No. 7,179,965 relates to cotton having a cry1F event and a cry1Ac event.

AAD-1 corn having the specific event disclosed herein has not previously been disclosed.

BRIEF SUMMARY OF THE INVENTION

The present invention is related to the AAD-1 corn event designated DAS-40278-9 having seed deposited with American Type Culture Collection (ATCC) with Accession No. PTA-10244, and progeny derived thereof. Other aspects of the invention comprise the progeny plants, seeds and grain or regenerable parts of the plants and seeds and progeny of corn event DAS-40278-9, as well as food or feed products made from any thereof. The invention also includes plant parts of corn event DAS-40278-9 that include, but are not limited to, pollen, ovule, flowers, shoots, roots, and leaves, and nuclei of vegetative cells, pollen cells, and egg cells. The invention further relates to corn plants having tolerance to phenoxy auxinic and/or aryloxyalkanoate herbicides, novel genetic compositions of corn event DAS-40278-9, and aspects of agronomic performance of corn plants comprising corn event DAS-40278-9.

This invention relates in part to plant breeding and herbicide tolerant plants. This invention includes a novel aad-1 transformation event in corn plants comprising a polynucleotide sequence, as described herein, inserted into a specific site within the genome of a corn cell.

In some embodiments, said event/polynucleotide sequence can be "stacked" with other traits, including, for example, other herbicide tolerance gene(s) and/or insect-inhibitory proteins. However, the subject invention includes plants having the single event, as described herein.

The additional traits may be stacked into the plant genome via plant breeding, re-transformation of the transgenic plant containing corn event DAS-40278-9, or addition of new traits through targeted integration via homologous recombination.

Other embodiments include the excision of polynucleotide sequences which comprise corn event DAS-40278-9, including for example, the pat gene expression cassette. Upon excision of a polynucleotide sequence, the modified event may be re-targeted at a specific chromosomal site wherein additional polynucleotide sequences are stacked with corn event DAS-40278-9.

In one embodiment, the present invention encompasses a corn chromosomal target site located on chromosome 2 at approximately 20 cM between SSR markers UMC1265 (see SEQ ID) NO:30 and SEQ ID NO:31) and MMC0111 (see SEQ ID NO:32 and SEQ ID NO:33) at approximately 20 cM on the 2008 DAS corn linkage map, wherein the target site comprises a heterologous nucleic acid. In another embodiment, the present invention encompasses a corn chromosomal target site comprising a location defined in or by SEQ ID NO:29 and the residues thereof as described herein, as would be recognized by one skilled in the art.

In one embodiment, the present invention encompasses a method of making a transgenic corn plant comprising inserting a heterologous nucleic acid at a position on chromosome 2 at approximately 20 cM between SSR markers UMC1265 (see SEQ ID NO:30 and SEQ ID NO:31) and MMC0111 (see SEQ ID NO:32 and SEQ ID NO:33) at approximately 20 cM on the 2008 DAS corn linkage map. In still another embodiment, the inserted heterologous nucleic acid is flanked 5' by all or part of the 5' flanking sequence as defined herein with reference to SEQ ID NO:29, and flanked 3' by all or part of the 5' flanking sequence as defined herein with reference to SEQ ID NO:29.

Additionally, the subject invention provides assays for detecting the presence of the subject event in a sample (of corn grain, for example). The assays can be based on the DNA sequence of the recombinant construct, inserted into the corn genome, and on the genomic sequences flanking the insertion site. Kits and conditions useful in conducting the assays are also provided.

Thus, the subject invention relates in part to the cloning and analysis of the DNA sequences of a whole AAD-1 insert, and the border regions thereof (in transgenic corn lines). These sequences are unique. Based on these insert and border sequences, event-specific primers were generated. PCR analysis demonstrated that these events can be identified by analysis of the PCR amplicons generated with these event-specific primer sets. Thus, these and other related procedures can be used to uniquely identify corn lines comprising the event of the subject invention.

BRIEF DESCRIPTION OF THE FIGURES

FIG. 6 illustrates the junction regions and insertion for DAS-40278-9.

BRIEF DESCRIPTION OF THE SEQUENCES

Figure 1:
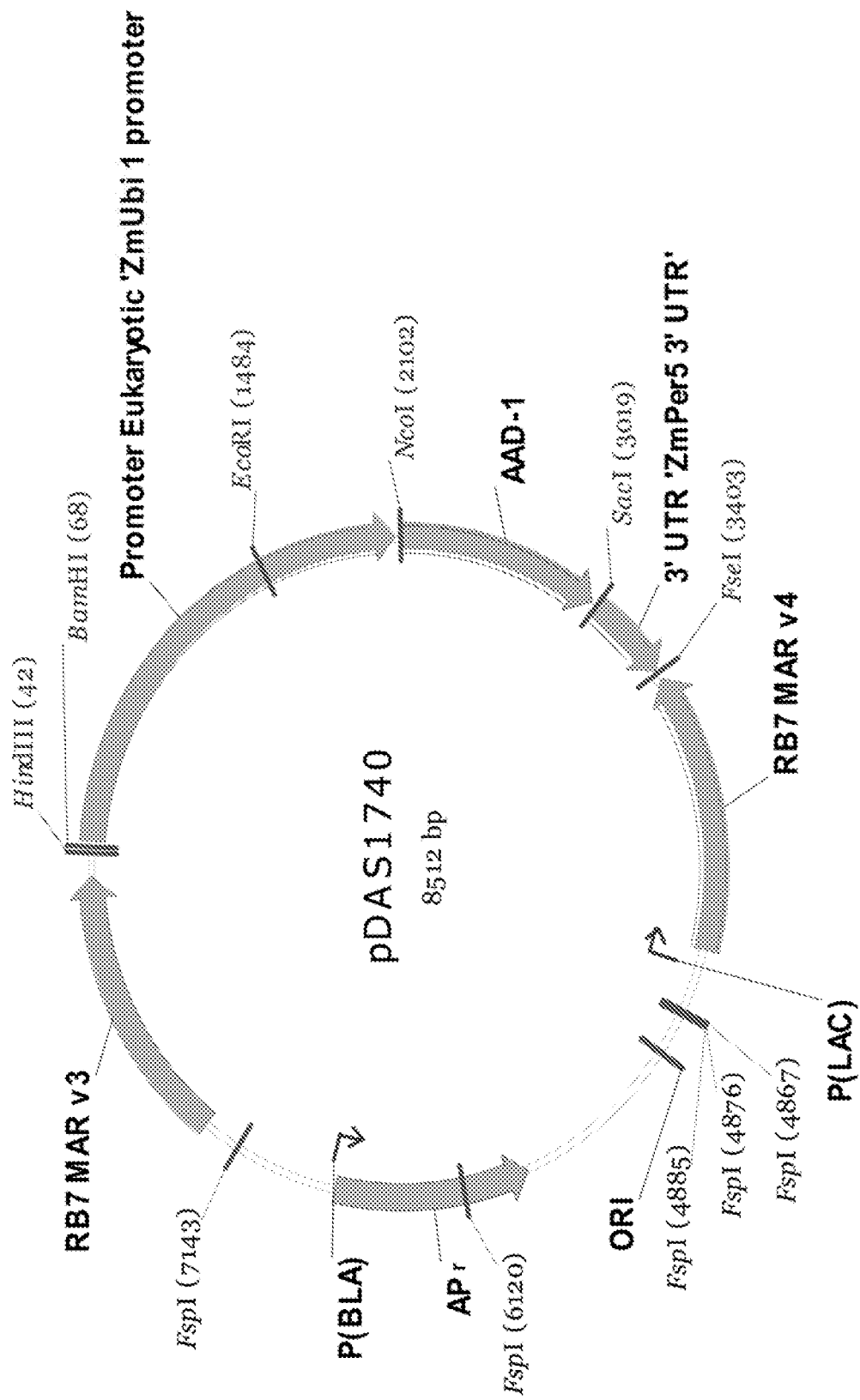
FIG. 1 shows a plasmid map of pDAS 1740.

SEQ ID NOs: 1-28 are primers as described herein.

SEQ ID NO:29 provides insert and flanking sequences for the subject event DAS-40278-9.

SEQ ID NOs: 30-33 are primers for flanking markers as described in Example 4.

DETAILED DESCRIPTION OF THE INVENTION

This invention relates in part to plant breeding and herbicide tolerant plants. This invention includes novel transformation events of corn plants (maize) comprising a subject aad-1 polynucleotide sequences, as described herein, inserted into specific site within the genome of a corn cell. In some embodiments, said polynucleotide sequence can be "stacked" with other traits (such as other herbicide tolerance gene(s) and/or gene(s) that encode insect-inhibitory proteins, for example. In some embodiments said polynucleotide sequences can be excised and subsequently re-targeted with additional polynucleotide sequences. However, the subject invention includes plants having a single event, as described herein.

Additionally, the subject invention provides assays for detecting the presence of the subject event in a sample. Aspects of the subject invention include methods of designing and/or producing any diagnostic nucleic acid molecules exemplified or suggested herein, particularly those based wholly or partially on the subject flanking sequences.

More specifically, the subject invention relates in part to transgenic corn event DAS-40278-9 (also known as pDAS 1740-278), plant lines comprising these events, and the cloning and analysis of the DNA sequences of this insert, and/or the border regions thereof. Plant lines of the subject invention can be detected using sequences disclosed and suggested herein.

In some embodiments, this invention relates to herbicide-tolerant corn lines, and the identification thereof. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example. It is possible to detect the presence of the subject event by any well-known nucleic acid detection method such as polymerase chain reaction (PCR) or DNA hybridization using nucleic acid probes. An event-specific PCR assay is discussed, for example, by Windels et al. (Med. Fac. Landbouww, Univ. Gent 64/5b: 459462, 1999). This related to the identification of glyphosate tolerant soybean event 40-3-2 by PCR using a primer set spanning the junction between the insert and flanking DNA. More specifically, one primer included sequence from the insert and a second primer included sequence from flanking DNA.

Corn was modified by the insertion of the aad-1 gene from Sphingobium herbicidovorans which encodes the aryloxy-alkanoate dioxygenase (AAD-1) protein. The trait confers tolerance to 2,4-dichlorophenoxyacetic acid and aryloxy-phenoxypropionate (commonly referred to as "fop" herbicides such as quizalofop) herbicides and may be used as a selectable marker during plant transformation and in breeding nurseries. Transformation of corn with a DNA fragment from the plasmid pDAS1740 was carried forward, through breeding, to produce event DAS-40278-9.

Genomic DNA samples extracted from twenty individual corn plants derived from five generations and four plants per generation of event DAS-40278-9 were selected for molecular characterization of the AAD-1 corn event DAS-40278-9. AAD-1 protein expression was tested using an AAD-1 specific rapid test strip kit. Only plants that tested positive for AAD-1 protein expression were selected for subsequent molecular characterization. Southern hybridization confirmed that the aad-1 gene is present in corn plants that tested positive for AAD-1 protein expression, and the aad-1 gene was inserted as a single intact copy in these plants when hybridized with an aad-1 gene probe.

Molecular characterization of the inserted DNA in AAD-1 corn event DAS-40278-9 is also described herein. The event was produced via Whiskers transformation with the Fsp I fragment of plasmid pDAS 1740. Southern blot analysis was used to establish the integration pattern of the inserted DNA fragment and determine insert/copy number of the aad-1 gene in event DAS-40278-9. Data were generated to demonstrate the integration and integrity of the aad-1 transgene inserted into the corn genome. Characterization of the integration of noncoding regions (designed to regulate the coding regions), such as promoters and terminators, the matrix attachment regions RB7 Mar v3 and RB7 Mar v4, as well as stability of the transgene insert across generations, were evaluated. The stability of the inserted DNA was demonstrated across five distinct generations of plants. Furthermore, absence of transformation plasmid backbone sequence including the Ampicillin resistance gene ($Ap^r$) region was demonstrated by probes covering nearly the whole backbone region flanking the restriction sites (Fsp I) of plasmid pDAS 1740. A detailed physical map of the insertion was drawn based on these Southern blot analyses of event DAS-40278-9.

Levels of AAD-1 protein were determined in corn tissues. In addition, compositional analysis was performed on corn forage and grain to investigate the equivalency between the isogenic non-transformed corn line and the transgenic corn line DAS-40278-9 (unsprayed, sprayed with 2,4-D, sprayed with quizalofop, and sprayed with 2,4-D and quizalofop). Agronomic characteristics of the isogenic non-transformed corn line were also compared to the DAS-40278-9 corn.

Field expression, nutrient composition, and agronomic trials of a non-transgenic control and a hybrid corn line containing Aryloxyalkanoate Dioxygenase-1 (AAD-1) were conducted in the same year at six sites located in Iowa, Illinois (2 sites), Indiana, Nebraska and Ontario, Canada. Expression levels are summarized herein for the AAD-1 protein in leaf, pollen, root, forage, whole plant, and grain, the results of agronomic determinations, and compositional analysis of forage and grain samples from the control and DAS-40278-9 AAD-1 corn.

The soluble, extractable AAD-1 protein was measured using a quantitative enzyme-linked immunosorbent assay (ELISA) method in corn leaf, pollen, root, forage, whole plant, and grain. Good average expression values were observed in root and pollen tissue, as discussed in more detail herein. Expression values were similar for all the sprayed treatments as well as for the plots sprayed and unsprayed with 2,4-D and quizalofop herbicides.

Compositional analyses, including proximates, minerals, amino acids, fatty acids, vitamins, anti-nutrients, and secondary metabolites were conducted to investigate the equivalency of DAS-40278-9 AAD-1 corn (with or without herbicide treatments) to the control. Results for DAS-40278-9 AAD-1 composition samples were all as good as, or better than (biologically and agronomically), based on control lines and/or conventional corn, analysis of agronomic data collected from control and DAS-40278-9 AAD-1 corn plots.

As alluded to above in the Background section, the introduction and integration of a transgene into a plant genome involves some random events (hence the name "event" for a given insertion that is expressed). That is, with many transformation techniques such as *Agrobacterium* transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

As "events" are originally random events, as part of this disclosure at least 2500 seeds of a corn line comprising the event have been deposited and made available to the public without restriction (but subject to patent rights), with the American Type Culture Collection (ATCC), 10801 University Boulevard, Manassas, Va., 20110. The deposit has been designated as ATCC Deposit No. PTA-10244 (Yellow Dent maize hybrid seed (Zea Mays L.):DAS-40278-9; Deposited on behalf of Dow AgroSciences LLC; Date of receipt of seeds/strain(s) by the ATTC: Jul. 10, 2009; viability confirmed Aug. 17, 2009). This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, corn plants can be grown from these seeds, and such plants are part of the subject invention. The subject invention also relates to DNA sequences contained in these corn plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR § 1.822 is used.

As used herein, the term "progeny" denotes the offspring of any generation of a parent plat which comprises AAD-1 corn evend DAS-40278-9.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the corn native genome flanking the insertion point, the identification or detection of one or the other junction sequences in a plant's genetic material being sufficient to be diagnostic for the event. Included are the DNA sequences that span the insertions in herein-described corn events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates to the identification of such flanking, junction, and insert sequences. Related PCR primers and amplicons are included in the invention. According to the subject invention, PCR analysis methods using amplicons that span across inserted DNA and its borders can be used to detect or identify commercialized transgenic corn varieties or lines derived from the subject proprietary transgenic corn lines.

The entire sequences of each of these inserts, together with portions of the respective flanking sequences, are provided herein as SEQ ID NO:29. The coordinates of the insert and flanking sequences for this event with respect to SEQ ID NO:29 (8557 basepairs total) are printed below. This is discussed in more detail in Example 3.8, for example.

|  | 5' Flanking | Insert | 3' Flanking |
| --- | --- | --- | --- |
| residue #s (SEQ: 29): | 1-1873 | 1874-6689 | 6690-8557 |
| length (bp): | 1873 bp | 4816 bp | 1868 bp |

Figure 2:
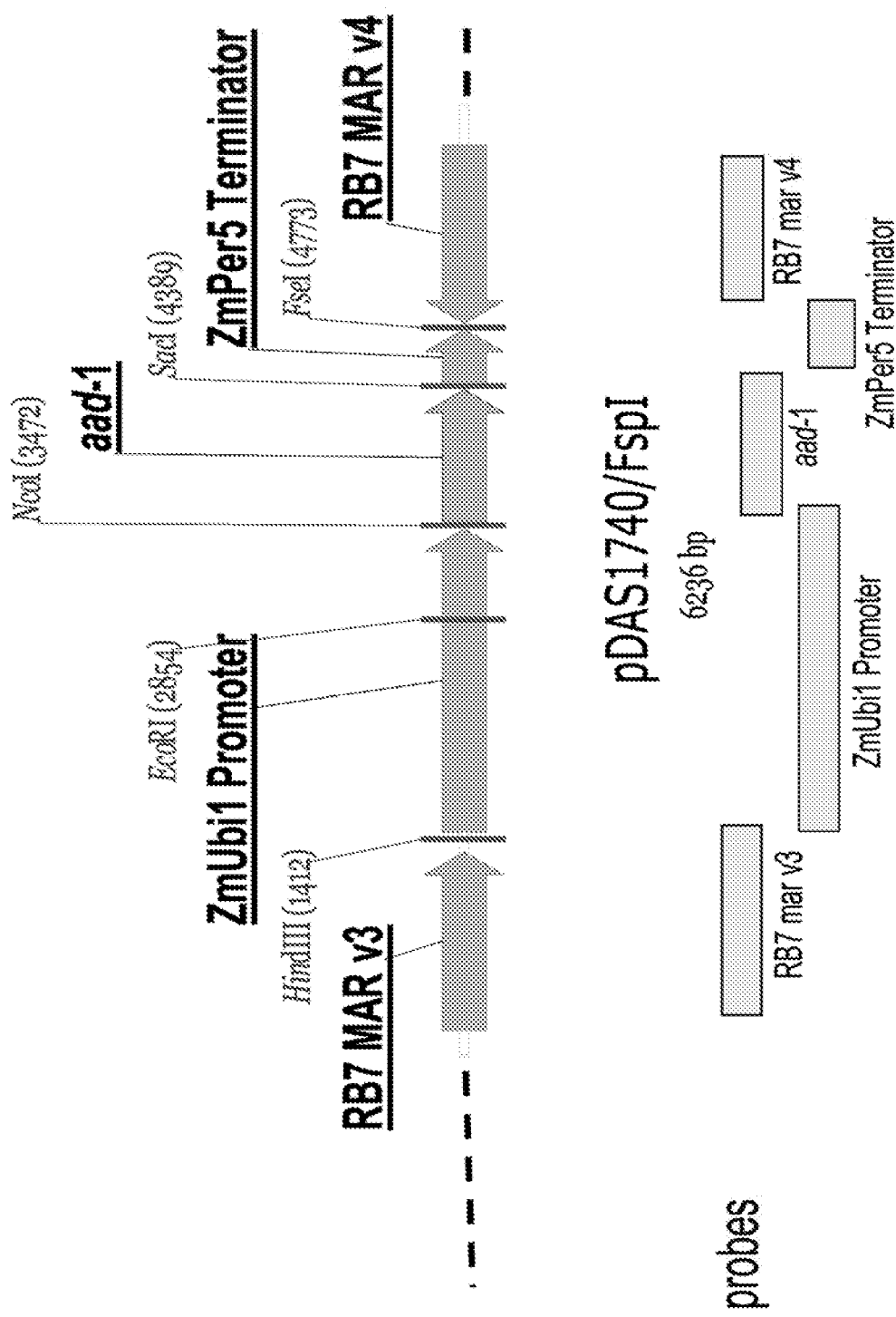
FIG. 2 shows components of the insert for DAS-40278-9 (pDAS 1740).

This insertion event, and further components thereof, are further illustrated in FIGS. 1 and 2. These sequences (particularly the flanking sequences) are unique. Based on these insert and border sequences, event-specific primers were generated. PCR analysis demonstrated that these corn lines can be identified in different corn genotypes by analysis of the PCR amplicons generated with these event-specific primer sets. Thus, these and other related procedures can be used to uniquely identify these corn lines. The sequences identified herein are unique. For example, BLAST searches against GENBANK databases did not reveal any significant homology between the cloned border sequences and sequences in the database.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit corn breeding programs as well as quality control, especially for commercialized transgenic cornseeds. PCR detection kits for these transgenic corn lines can also now be made and used. This can also benefit product registration and product stewardship.

Furthermore, flanking corn/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that the subject invention includes seeds available under ATCC Deposit No. PTA-10244. The subject invention also includes a herbicide-resistant corn plant grown from a seed deposited with the ATCC under accession number PTA-10244. The subject invention further includes parts of said plant, such as leaves, tissue samples, seeds produced by said plant, pollen, and the like.

Still further, the subject invention includes descendant and/or progeny plants of plants grown from the deposited seed, preferably a herbicide-resistant corn plant wherein said plant has a genome comprising a detectable wild-type genomic DNA/insert DNA junction sequence as described herein. As used herein, the term "corn" means maize (*Zea mays*) and includes all varieties thereof that can be bred with corn.

This invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

A herbicide-tolerant corn plant can be bred by first sexually crossing a first parental corn plant consisting of a corn plant grown from seed of any one of the lines referred to herein, and a second parental corn plant, thereby producing a plurality of first progeny plants; and then selecting a first progeny plant that is resistant to a herbicide (or that possesses at least one of the events of the subject invention); and selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental corn plant or a third parental corn plant. A corn crop comprising corn seeds of the subject invention, or progeny thereof, can then be planted.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The herbicide-resistance trait can be tracked in the progeny of a cross with a corn plant of the subject invention (or progeny thereof and any other corn cultivar or variety) using the MAB methods. The DNA molecules are markers for this trait, and MAB methods that are well known in the art can be used to track the hebicide-resistance trait(s) in corn plants where at least one corn line of the subject invention, or progeny thereof, was a parent or ancestor. The methods of the present invention can be used to identify any corn variety having the subject event.

Methods of the subject invention include a method of producing a herbicide-tolerant corn plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One preferred embodiment of the latter is a plant comprising the subject event combined with a gene encoding resistance to the herbicide dicamba.

Thus, the subject invention can be combined with, for example, traits encoding glyphosate resistance (e.g., resistant plant or bacterial EPSPS, GOX, GAT), glufosinate resistance (e.g., Pat, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Regarding additional herbicides, some additional preferred ALS (also known as AHAS) inhibitors include the triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include mesotrione, isoxaflutole, and sulcotrione. Some preferred PPO inhibitors include flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-1 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in US Patent Application Publication No. 2009/0111188 A1 describes the use of recombinases or integrases to mediate the introduction of a donor polynucleotide sequence into a chromosomal target. In addition, International Patent Application No. WO 2008/021207 describes zinc finger mediated-homologous recombination to integrate one or more donor polynucleotide sequences within specific locations of the genome. The use of recombinases such as FLP/FRT as described in U.S. Pat. No. 6,720,475 or CRE/LOX as described in U.S. Pat. No. 5,658,772 can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060.

Other various methods for site specific integration within plant cells are generally known and applicable (Kumar et al., Trands in Plant Sci. 6 (4) (2001) pp. 155-159). Furthermore, site-specific recombination systems which have been identified in several prokaryotic and lower eukaryotic organisms may be applied to use in plants. Examples of such systems include, but are not limited too: the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it can be desirable to excise polynucleotide sequences from a transgenic event. For instance transgene excision as described in Provisional U.S. Patent Application No. 61/297,628 describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 2 in the corn genome that is excellent for insertion of heterologous nucleic acids. Also disclosed is a 5' molecular marker, a 3' molecular marker, a 5' flanking sequence, and a 3' flanking sequence useful in identifying the location of a targeting site on chromosome 2. Thus, the subject invention provides methods to introduce heterologous nucleic acids of interest into this pre-established target site or in the vicinity of this target site. The subject invention also encompasses a corn seed and/or a corn plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

The subject AAD-1 enzyme enables transgenic expression resulting in tolerance to combinations of herbicides that would control nearly all broadleaf and grass weeds. AAD-1 can serve as an excellent herbicide tolerant crop (HTC) trait to stack with other HTC traits (e.g., glyphosate resistance, glufosinate resistance, imidazolinone resistance, bromoxynil resistance, et al.), and insect resistance traits (Cry1F, Cry1Ab, Cry 34/45, et al.) for example. Additionally, AAD-1 can serve as a selectable marker to aid in selection of primary transformants of plants genetically engineered with a second gene or group of genes.

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

Additionally, glyphosate tolerant crops grown worldwide are prevalent. Many times in rotation with other glyphosate tolerant crops, control of glyphosate-resistant volunteers may be difficult in rotational crops. Thus, the use of the subject transgenic traits, stacked or transformed individually into crops, provides a tool for controlling other HTC volunteer crops.

A preferred plant, or a seed, of the subject invention comprises in its genome the insert sequences, as identified herein, together with at least 20-500 or more contiguous flanking nucleotides on both sides of the insert, as identified herein. Unless indicated otherwise, reference to flanking sequences refers to those identified with respect to SEQ ID NO:29 (see the Table above). Again, SEQ ID NO:29 includes the heterologous DNA inserted in the original transformant and illustrative flanking genomic sequences immediately adjacent to the inserted DNA. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when
  (i) it is predominantly derived from the initial variety, or from a variety that is itself predominantly derived from the initial variety, while retaining the expression of the essential characteristics that result from the genotype or combination of genotypes of the initial variety;

(ii) it is clearly distinguishable from the initial variety; and (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably .+-0.15%, more preferably .+-0.10%, most preferably .+-0.5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the insect resistance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the corn genomic flanking sequence meets the insert sequence). For example, this includes a polynucleotide probes, primers, and/or amplicons designed to identify one or both junction sequences (where the insert meets the flanking sequence), as indicated in Table 1. One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 200 bases or beyond the junction. Thus, typical flanking primers would be designed to comprise at least 15 residues of either strand within 200 bases into the flanking sequences from the beginning of the insert. That is, primers comprising sequence of an appropriate size in residues ~1674-1873 and/or ~6690-6890 of SEQ ID NO:29 are within the scope of the subject invention. Insert primers can likewise be designed anywhere on the insert, but residues ~1874-2074 and ~6489-6689, can be used, for example, non-exclusively for such primer design.

One skilled in the art will also recognize that primers and probes can be designed to hybridize, under a range of standard hybridization and/or PCR conditions, to a segment of SEQ ID NO:29 (or the complement), and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from corn genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice than any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Some of these difference(s) are discussed below in the Examples section. Adjustments to probes and primers can be made accordingly.

The components of each of the "inserts" are illustrated in FIGS. 1 and 2 and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a corn plant. DNA sequences are provided that comprise the subject transgene/genomic insertion region junction sequence provided herein (between residues 1873-1874 and 6689-6690 of SEQ ID NO:29), segments thereof, and complements of the exemplified sequences and any segments thereof. The insertion region junction sequence spans the junction between heterologous DNA inserted into the genome and the DNA from the corn cell flanking the insertion site. Such sequences can be diagnostic for the given event.

Based on these insert and border sequences, event-specific primers can be generated. PCR analysis demonstrated that corn lines of the subject invention can be identified in different corn genotypes by analysis of the PCR amplicons generated with these event-specific primer sets. These and other related procedures can be used to uniquely identify these corn lines. Thus, PCR amplicons derived from such primer pairs are unique and can be used to identify these corn lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of corn genomic sequence from one or more of the three aforementioned corn plants and/or sequences that are useful as primer sequences for the production of an amplicon product diagnostic for one or more of these corn plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:29 and segments thereof), or complements thereof, and a similar length of flanking corn DNA sequence from these sequences, or complements thereof. Such sequences are useful as DNA primers in DNA amplification methods. The amplicons produced using these primers are diagnostic for any of the corn events referred to herein. Therefore, the invention also includes the amplicons produced by such DNA primers and homologous primers.

This invention also includes methods of detecting the presence of DNA, in a sample, that corresponds to the corn event referred to herein. Such methods can comprise: (a) contacting the sample comprising DNA with a primer set that, when used in a nucleic acid amplification reaction with DNA from at least one of these corn events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to at least one of said events, wherein said method comprises: (a) contacting the sample comprising DNA with a probe that hybridizes under stringent hybridization conditions with DNA from at least one of said corn events and which does not hybridize under the stringent hybridization conditions with a control corn plant (non-event-of-interest DNA); (b) subjecting the sample and probe to stringent hybridization conditions; and (c) detecting hybridization of the probe to the DNA.

In still further embodiments, the subject invention includes methods of producing a corn plant comprising the aad-1 event of the subject invention, wherein said method comprises the steps of: (a) sexually crossing a first parental corn line (comprising an expression cassettes of the present invention, which confers said herbicide resistance trait to plants of said line) and a second parental corn line (that lacks this herbicide tolerance trait) thereby producing a plurality of progeny plants; and (b) selecting a progeny plant by the use of molecular markers. Such methods may optionally comprise the further step of back-crossing the progeny plant to the second parental corn line to producing a true-breeding corn plant that comprises said insect tolerance trait.

According to another aspect of the invention, methods of determining the zygosity of progeny of a cross with any one (or more) of said three events are provided. Said methods can comprise contacting a sample, comprising corn DNA, with a primer set of the subject invention. Said primers, when used in a nucleic-acid amplification reaction with genomic DNA from at least one of said corn events, produces a first amplicon that is diagnostic for at least one of said corn events. Such methods further comprise performing a nucleic acid amplification reaction, thereby producing the first amplicon; detecting the first amplicon; and contacting the sample comprising corn DNA with said primer set (said primer set, when used in a nucleic-acid amplification reaction with genomic DNA from corn plants, produces a second amplicon comprising the native corn genomic DNA homologous to the corn genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject corn event DNA in a sample and can be applied to methods for breeding corn plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said corn events, whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence set forth in SEQ ID NOS:3-14, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the corn plant resulting from a sexual cross contains transgenic event genomic DNA from the corn plant of the present invention, DNA extracted from a corn plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject corn event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the corn genome that is excellent for an insertion, the subject invention also comprises a corn seed and/or a corn plant comprising at least one non-aad 1 insert in the general vicinity of this genomic location. One option is to substitute a different insert in place of the aad-1 insert exemplified herein. In these generally regards, targeted homologous recombination, for example, can be used according to the subject invention. This type of technology is the subject of for example, WO 03/080809 A2 and the corresponding published U.S. application (US 20030232410). Thus, the subject invention includes plants and plant cells comprising a heterologous insert (in place of or with multi-copies of aad-1), flanked by all or a recognizable part of the flanking sequences identified herein (e.g. residues 1-1873 and 6690-8557 of SEQ ID NO:29).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

AAD-1 aryloxyalkanoate dioxygenase-1
bp base pair
° C. degrees Celcius
DNA deoxyribonucleic acid
DIG digoxigenin
EDTA ethylenediaminetetraacetic acid
kb kilobase
µg microgram
µL microliter
mL milliliter
M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1

Transformation and Selection of the AAD1 Event pDAS1740-278

The AAD1 event, pDAS1740-278, was produced by WHISKER—mediated transformation of maize line Hi-11. The transformation method used is described in US Patent Application #20090093366. An FspI fragment of plasmid pDAS1740, also referred to as pDAB3812, (FIG. 1) was transformed into the maize line. This plasmid construct contains the plant expression cassette containing the RB7 MARv3:: Zea mays Ubiquitin 1 promoter v2//AAD1 v3// Zea mays PERS 3'UTR:: RB 7 MARv4 plant transcription unit (PTU).

Numerous events were produced. Those events that survived and produced healthy, haloxyfop-resistant callus tissue were assigned unique identification codes representing putative transformation events, and continually transferred to fresh selection medium. Plants were regenerated from tissue derived from each unique event and transferred to the greenhouse.

Leaf samples were taken for molecular analysis to verify the presence of the AAD-1 transgene by Southern Blot, DNA border confirmation, and genomic marker assisted confirmation. Positive T0 plants were pollinated with inbred lines to obtain T1 seed. T1 plants of Event pDAS1470-278-9

(DAS-40278-9) was selected, self-pollinated and characterized for five generations. Meanwhile, the T1 plants were backcrossed and introgressed into elite germplasm (XHH13) through marker-assisted selection for several generations. This event was generated from an independent transformed isolate. The event was selected based on its unique characteristics such as single insertion site, normal Mendelian segregation and stable expression, and a superior combination of efficacy, including herbicide tolerance and agronomic performance in broad genotype backgrounds and across multiple environmental locations. The following examples contain the data which were used to characterize event pDAS-1740-278-9.

Example 2 pDAS1740-278-9 Event Characterization via Southern Blot

Southern blot analysis was used to establish the integration pattern of the inserted DNA fragment and determine insert/copy number of the aad-1 gene in event pDAS-1740-278-9 (DAS-40278-9). Data were generated to demonstrate the integration and integrity of the aad-1 transgene inserted into the corn genome.

Southern blot data suggested that the pDAS1740/Fsp I fragment insert in corn event DAS-40278-9 occurred as a simple integration of a single, intact copy of the aad-1 PTU from plasmid pDAS 1740. Detailed Southern blot analysis was conducted using probes specific to gene, promoter, terminator, and other regulation elements contained in the plasmid region and descriptive restriction enzymes that have cleavage sites located within the plasmid and produce hybridizing fragments internal to the plasmid or fragments that span the junction of the plasmid with corn genomic DNA (border fragments). The molecular weights indicated from the Southern hybridization for the combination of the restriction enzyme and the probe were unique for the event, and established its identification patterns. These analyses also showed that the plasmid fragment had been inserted into corn genomic DNA without rearrangements of the aad-1 PTU. Identical hybridization fragments were observed in five distinct generations of transgenic corn event DAS-40278-9 indicating stability of inheritance of the aad-1 PTU insertion across generations. Hybridization with a mixture of three backbone probes located outside of the restriction site of Fsp I on plasmid pDAS 1740 did not detect any specific DNA/gene fragments, indicating the absence of the Ampicillin resistance gene and the absence of the other vector backbone regions immediately adjacent to the Fsp I restriction sites of the plasmid pDAS 1740 in transgenic corn event DAS-40278-9. The illustrated map of the insert in aad-1 corn event DAS-40278-9 is presented in FIGS. 2-3.

Example 2.1

Corn Leaf Sample Collection and Genomic DNA (gDNA) Isolation gDNA prepared from leaf of the individual plants of the aad-1 corn event DAS-40278-9. gDNA was extracted from leaf tissue harvested from individual plants carrying aad-1 corn event DAS-40278-9. Transgenic corn seeds from five distinct generations of event DAS-40278-9 were used. Twenty individual corn plants, derived from four plants per generation, for event DAS-40278-9 were selected. In addition, gDNA was isolated from a conventional corn plant, XHH13, which contains the genetic background that is representative of the substance line, absent the aad-1 gene.

Prior to isolating the gDNA, leaf punches were taken from each plant to test aad-1 protein expression using a rapid test strip kit (American Bionostica, Swedesboro, N.J.) according to the manufacturer's recommended procedure. Each leaf punch sample was given a score of + or − for the presence or absence of aad-1, respectively. Only positive plants from the five generations of event DAS-40278-9 were subjected to further characterization.

Corn leaf samples were collected from the individual plants of the event DAS-40278-9 and the conventional control XHH13. Leaf samples were quickly frozen in liquid nitrogen and stored at approximately −80° C. until usage.

Individual genomic DNA was extracted from frozen corn leaf tissue following the standard CTAB method. When necessary, some of the genomic DNA was further purified with Qiagen Genomic-Tip (Qiagen, Valencia, Calif.) following procedures recommended by the manufacturer. Following extraction, the DNA was quantified spectrofluorometrically using Pico Green reagent (Invitrogen, Carlsbad, Calif.). The DNA was then visualized on an agarose gel to confirm values from the Pico Green analysis and to determine the DNA quality.

Example 2.2

DNA Digestion and Separation

For molecular characterization of the DNA, nine micrograms (9 μg) of genomic DNA from the corn event DAS-40278-9 DNA sample and the conventional control were digested by adding approximately five to eleven units of selected restriction enzyme per μg of DNA and the corresponding reaction buffer to each DNA sample. Each sample was incubated at approximately 37° C. overnight. The restriction enzymes EcoR I, Nco I, Sac I, Fse I, and Hind III were used for the digests (New England Biolabs, Ipswich, Mass.). A positive hybridization control sample was prepared by combining plasmid DNA, pDAS1740 (pDAB3812), with genomic DNA from the conventional control at a ratio of approximately equivalent to 1 copy of transgene per corn genome, and digested using the same procedures and restriction enzyme as the test samples. DNA from the conventional corn control (XHH13) was digested using the same procedures and restriction enzymes as the test samples to serve as a negative control.

The digested DNA samples were precipitated with Quick-Precip (Edge BioSystems, Gaithersburg, Md.) and resuspended in 1' Blue Juice (Invitrogen, Carlsbad, Calif.) to achieve the desired volume for gel loading. The DNA samples and molecular size markers were then electrophoresed through 0.8% agarose gels with 1×TBE buffer (Fisher Scientific, Pittsburgh, Pa.) at 55-65 volts for approximately 18-22 hours to achieve fragment separation. The gels were stained with ethidium bromide (Invitrogen, Carlsbad, Calif.) and the DNA was visualized under ultraviolet (UV) light.

Example 2.3

Southern Transfer and Membrane Treatment

Southern blot analysis was performed essentially as described by Memelink, et al. (1994) Southern, Northern, and Western Blot Analysis. Plant Mol. Biol. Manual F1:1-23. Briefly, following electrophoretic separation and visualization of the DNA fragments, the gels were depurinated with 0.25N HCl (Fisher Scientific, Pittsburgh, Pa.) for approximately 15 minutes, and then exposed to a denaturing solution (AccuGENE, Sigma, St. Louis, Mo.) for approximately 30 minutes followed by neutralizing solution (AccuGENE, Sigma, St. Louis, Mo.) for at least 30 minutes. Southern transfer was performed overnight onto nylon membranes (Roche Diagnostics, Indianapolis, Ind.) using a wicking system with 10×SSC (Sigma, St. Louis, Mo.). After transfer the membranes were washed in a 2×SSC solution and the DNA was bound to the membrane by UV crosslinking. This process resulted in Southern blot membranes ready for hybridization.

Example 2.4

DNA Probe Labeling and Hybridization

The DNA fragments bound to the nylon membrane were detected using a labeled probe. Probes used for the study were generated by a PCR-based incorporation of a digoxigenin (DIG) labeled nucleotide, [DIG-11]-dUTP, from fragments generated by primers specific to gene elements and other regions from plasmid pDAS 1740. Generation of DNA probes by PCR synthesis was carried out using a PCR DIG Probe Synthesis Kit (Roche Diagnostics, Indianapolis, Ind.) following the manufacturer's recommended procedures. A list of probes used for the study is described in Table 1.

TABLE 1

Location and Length of Probes used in Southern Analysis.

| Probe Name | Genetic Element | Position on pDAS1740 (bp) | Length (bp) |
|---|---|---|---|
| OLP1-3 | ubiquitin promoter (ZmUbi1) | 28-2123 | 2096 |
| OLP2 | aad-1 gene | 2103-3022 | 920 |
| OLP3A | peroxidase terminator (ZmPer5) | 3002-3397 | 396 |
| OLP3B | RB7 Mar v4 | 3375-4865 | 1491 |
| OLP4ABC | Backbone (OLP4A) | 4900-5848 | 949 |
|  | Backbone Ap$^r$ gene (OLP4B) | 5828-6681 | 855 |
|  | Backbone (OLP4C) | 6660-7144 | 485 |
| OLP5-2 | RB7 Mar v3 | 7124-8507 | 1384 |

Labeled probes were analyzed by agarose gel electrophoresis to determine their quality and quantity. A desired amount of labeled probe was then used for hybridization to the target DNA on the nylon membranes for detection of the specific fragments using the procedures described for DIG Easy Hyb Solution (Roche Diagnostics, Indianapolis, Ind.). Briefly, nylon membrane blots with DNA fixed on were briefly washed in 2×SSC and prehybridized with 20-25 mL of prewarmed DIG Easy Hyb solution in hybridization bottles at approximately 50° C. for a minimal of 30 minutes in a hybridization oven. The prehybridization solution were then decanted and replaced with 20 mL of prewarmed DIG Easy Hyb solution containing a desired amount of specific probes predenatured by boiling in water for 5 minutes. The hybridization step was then conducted at approximately 40-60° C. overnight in the hybridization oven.

Example 2.5

Detection

At the end of the probe hybridization, DIG Easy Hyb solutions containing the probes were decanted into clean tubes and stored at −20° C. These probes could be reused for 2-3 times according to the manufacturer's recommended procedure. The membrane blots were rinsed briefly and washed twice in clean plastic containers with low stringency wash buffer (2×SSC, 0.1% SDS) for approximately 5 minutes at room temperature, followed by washing twice with high stringency wash buffer (0.1×SSC, 0.1% SDS) for 15 minutes each at approximately 65° C. The membrane blots were then transferred to other clean plastic containers and briefly washed with 1× washing buffer from the DIG Wash and Block Buffer Set (Roche Diagnostics, Indianapolis, Ind.) for approximately 2 minutes, proceeded to blocking in 1× blocking buffer for a minimum of 30 minutes, followed by incubation with anti-DIG-AP (alkaline phosphatase) antibody (1:5,000 dilution, Roche Diagnostics, Indianapolis, Ind.) in 1× blocking buffer for a minimum of 30 minutes. After 2-3 washes with 1× washing buffer, specific DNA probes remain bound to the membrane blots and DIG-labeled DNA standards were visualized using CDP-Star Chemiluminescent Nucleic Acid Detection System (Roche Diagnostics, Indianapolis, Ind.) following the manufacturer's recommendation. Blots were exposed to chemiluminescent film (Roche Diagnostics, Indianapolis, Ind.) for one or more time points to detect hybridizing fragments and to visualize molecular size standards. Films were then developed with an All-Pro 100 Plus film developer (Konica SRX-101) and images were scanned for report. The number and sizes of detected bands were documented for each probe. DIG-labeled DNA Molecular Weight Marker II (MWM DIG II), visible after DIG detection as described, was used to determine hybridizing fragment size on the Southern blots.

Example 2.6

Probe Stripping

DNA probes were stripped off the membrane blots after the Southern hybridization data were obtained, and the membrane blots could be reused for hybridization with a different DNA probe according to the manufacturer's recommended procedures (DIG Application Manual for Filter Hybridization, (2003). Roche Diagnostics). Briefly, after signal detection and film exposure, membrane blots were thoroughly rinsed with Milli-Q water and followed by washing twice in stripping buffer (0.2N NaOH, 0.1% SDS) for approximately 15 minutes at room temperature or at 37° C. The membrane blots were then briefly washed in 2×SSC and were ready for prehybridization and hybridization with another DNA probe. The membrane blots were exposed to a new chemiluminescent film to ensure all the DNA probes were stripped of before proceeding to the next hybridization. The re-exposed films were kept along with the previous hybridization data package in the study file for record.

Example 2.7

Southern Blot Results

Figure 3:
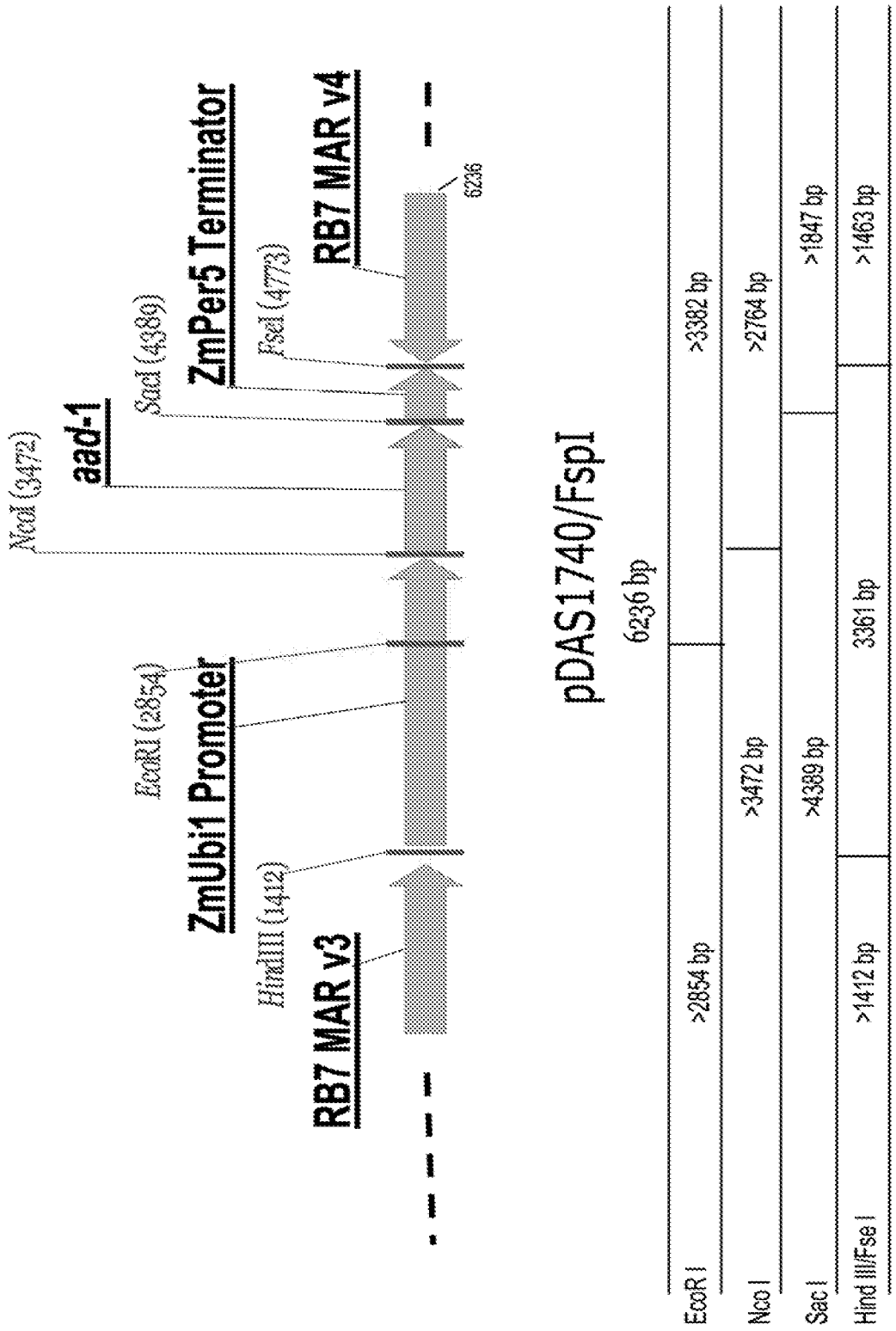
FIG. 3 shows a restriction map and components of the insert for DAS-40278-9 (pDAS 1740).

Expected and observed fragment sizes with a particular digest and probe, based on the known restriction enzyme sites of the pDAS1740/Fsp I fragment, are given in Table 2. Two types of fragments were identified from these digests and hybridizations: internal fragments, where known enzyme sites flank the probe region and are completely contained within the pDAS1740/Fsp I fragment, and border fragments where a known enzyme site is located at one end of the probe region and a second site is expected in the corn genome. Border fragment sizes vary by event because, in most cases, DNA fragment integration sites are unique for each event. The border fragments provide a means to locate a restriction enzyme site relative to the integrated DNA and to evaluate the number of DNA insertions. Based on the Southern blot analyses completed in this study, it was concluded that a single copy of an intact aad-1 PTU from plasmid pDAS1740/Fsp I inserted into the corn genome of event DAS-40278-9 as detailed in the insert map (FIGS. 2-3).

TABLE 2

Predicted and Observed Hybridizing Fragments in Southern Blot Analysis.

| DNA Probe | Restriction Enzymes | | Expected Fragment Sizes (bp) [1] | Observed Fragment Size (bp)2 |
|---|---|---|---|---|
| aad-1 | EcoR I | pDAS1740 | 8512 | 8512 |
| | | XHH13 | none | none |
| | | DAS-40278-9 | >3382 (border) | ~12000 |
| | Nco I | pDAS1740 | 8512 | 8512 |
| | | XHH13 | none | none |
| | | DAS-40278-9 | >2764 (border) | ~4000 |
| | Sac I | pDAS1740 | 8512 | 8512 |
| | | XHH13 | none | none |
| | | DAS-40278-9 | >4389 (border) | ~16000 |
| | Fse I/ Hind III | pDAS1740 | 3361 | 3361 |
| | | XHH13 | none | none |
| | | DAS-40278-9 | 3361 | 3361 |
| ZmUbi1 prom. | Nco I | pDAS1740 | 8512 | 8512, ~3600* |
| | | XHH13 | none | ~3600* |
| | | DAS-40278-9 | >3472 (border) | ~6300, ~3600* |
| | Sac I | pDAS1740 | 8512 | 8512, ~3800* |
| | | XHH13 | none | ~3800* |
| | | DAS-40278-9 | >4389 (border) | ~3800*, ~16000 |
| | Fse I/ Hind III | pDAS1740 | 3361 | 3361, ~6400* |
| | | XHH13 | none | ~6400* |
| | | DAS-40278-9 | 3361 | 3361, ~6400*# |
| ZmPer5 term. | Nco I | pDAS1740 | 8512 | 8512, ~3900* |
| | | XHH13 | none | ~3900* |
| | | DAS-40278-9 | >2764 (border) | ~4000, ~3900* |
| | Sac I | pDAS1740 | 8512 | 8512, ~9000* |
| | | XHH13 | none | ~9000* |
| | | DAS-40278-9 | >1847 (border) | ~1900, ~9000* |
| | Fse I/ Hind III | pDAS1740 | 3361 | 3361, ~2100* |
| | | XHH13 | none | ~2100* |
| | | DAS-40278-9 | 3361 | 3361, ~2100* |
| RB7 mar4 | Nco I | pDAS1740 | 8512 | 8512 |
| | | XHH13 | none | none |
| | | DAS-40278-9 | >2764 (border) | ~4000 |
| | | | >3472 (border) | ~6300 |
| | Sac I | pDAS1740 | 8512 | 8512 |
| | | XHH13 | none | none |
| | | DAS-40278-9 | >1847 (border) | ~1900 |
| | | | >4389 (border) | ~16000 |
| RB7 mar3 | Nco I | pDAS1740 | 8512 | 8512 |
| | | XHH13 | none | none |
| | | DAS-40278-9 | >2764 (border) | ~4000 |
| | | | >3472 (border) | ~6300 |
| | Sac I | pDAS1740 | 8512 | 8512 |
| | | XHH13 | none | none |
| | | DAS-40278-9 | >1847 (border) | ~1900 |
| | | | >4389 (border) | ~16000 |
| back-bone | Nco I | pDAS1740 | 8512 | 8512 |
| | | XHH13 | none | none |
| | | DAS-40278-9 | none | none |
| | Sac I | pDAS1740 | 8512 | 8512 |
| | | XHH13 | none | none |
| | | DAS-40278-9 | none | none |

Note:
*An asterisk after the observed fragment size indicates endogenous sequence hybridization that was detected across all samples (including negative controls)
Doublets in the conventional control, BC3S1, and some BC3S2 samples
[1] Expected fragment sizes are based on the plasmid map of the pDAS1740 (pDAB3812) as shown in FIG. 1
2Observed fragment sizes are considered approximately from these analyses and are based on the indicated sizes of the DIG-labeled DNA Molecular Weight Marker II fragments. Due to the incorporation of DIG molecules for visualization, the marker fragments typically run approximately 5-10% larger than their actual indicated molecular weight.

Restriction enzymes with unique restriction site in plasmid pDAS 1740, EcoR I, Nco I, Sac I, Fse I/Hind III, were selected to characterize aad-1 gene insert in event DAS-40278-9. Border fragment of >3382 bp, >2764 bp, >4389 bp was predicted to hybridize with the aad-1 gene probe following EcoR I, Nco I, and Sac I digest respectively (Table 2). Single aad-1 hybridization band of ~12000 bp, ~4000 bp, and ~16000 bp were observed when EcoR I, Nco I, and Sac I were used respectively, indicating a single site of aad-1 gene insertion in the corn genome of event DAS-40278-9. Double digestion with Fse I and Hind III was selected to release a fragment of 3361 bp which contains the aad-1 plant transcription unit (PTU, promoter/gene/terminator) (Table 2). The predicted 3361 bp fragment was observed with the aad-1 gene probe following Fse I/Hind III digestion. Results obtained with all four enzymes/enzyme combination digestion of the DAS-40278-9 sample followed by aad-1 gene probe hybridization indicated that a single copy of an intact aad-1 PTU from plasmid pDAS 1740 was inserted into the corn genome of event DAS-40278-9.

Restriction enzymes Nco I, Sac I and Fse I/Hind III were selected to characterize the promoter (ZmUbil) region for aad-1 in event DAS-40278-9. Nco I and Sac I digests were expected to generate a border region fragment of >3472 bp and >4389 bp, respectively, when hybridized to DNA probes specifically to the ZmUbil promoter region (Table 2). Two hybridization bands of ~6300 bp and ~3600 bp were detected with ZmUbil promoter probe following Nco I digestion. The ~3600 bp band, however, was present across all sample lanes including the conventional controls, suggesting that the ~3600 bp band is a non-specific signal band resulting from the homologous binding of the corn-derived ubiquitin promoter (ZmUbil) probe to the corn endogenous ubi gene. On the contrary, the ~6300 bp signal band was detected in the tested DAS-40278-9 samples but not in the conventional controls, indicating that the ~6300 bp band is specific to the ZmUbil promoter probe from plasmid pDAS1740 and therefore it is the expected Nco I/ZmUbil band indicated in Table 2. Similarly, two hybridization bands of ~3800 bp and ~16000 bp were detected with ZmUbil promoter probe following Sac I digestion. The ~3800 bp band appeared in all sample lanes including conventional controls and thus is considered as non-specific hybridization of ZmUbil promoter probe to the corn endogenous ubi gene. The ~16000 bp hybridization band that is only present in DAS-40278-9 samples is considered the expected Sac I/ZmUbil band.

Double digestion with Fse I/Hind III is expected to release the aad-1 PTU fragment of 3361 bp that hybridizes to the ZmUbi1 promoter probe (Table 2). This 3361 bp band and a non-specific hybridization band of ~6400 bp were detected by ZmUbi1 promoter probe following Fse I/Hind III digestion. The ~6400 bp band is considered non-specific binding of the ZmUbi1 promoter probe to the corn endogenous ubi gene because this band is present in all sample lanes including the conventional controls. Additionally, another band very close to ~6400 bp was observed in the conventional control, BC3S1, and some of the BC3S2 samples. This additional band very close to ~6400 bp is also considered non-specific because it is present in the conventional control XHH13 sample lanes and is most likely associated with the genetic background of XHH13.

The same restriction enzymes/enzyme combination, Nco I, Sac I and Fse I/Hind III were selected to characterize the terminator (ZmPer5) region for aad-1 in event DAS-40278-9. Nco I digest is expected to generate a border region fragment of >2764 bp when hybridized to DNA probes specifically to the ZmPer5 terminator region (Table 2). Two hybridization bands of ~4000 bp and ~3900 bp were detected with ZmPer5 terminator probe following Nco I digestion. The ~3900 bp band was present across all sample lanes including the conventional controls, suggesting that the ~3900 bp band is a non-specific signal band probably due to the homologous binding of the corn-derived peroxidase gene terminator (ZmPer5) probe to the corn endogenous per gene. On the contrary, the ~4000 bp signal band was detected in the tested DAS-40278-9 samples but not in the conventional controls, indicating that the ~4000 bp band is specific to the ZmPer5 terminator probe from plasmid pDAS 1740 and therefore it is the expected Nco I/ZmPer5 band indicated in Table 2. A >1847 bp border fragment is expected to hybridized to the ZmPer5 terminator probe following Sac I digestion. Two hybridization bands of ~1900 bp and ~9000 bp were detected with ZmPer5 terminator probe following Sac I digestion. The ~9000 bp band appeared in all sample lanes including conventional controls and thus considered as non-specific hybridization of ZmPer5 terminator probe to the corn endogenous per gene. The ~1900 bp hybridization band that was only present in DAS-40278-9 samples is considered the expected Sac I/ZmPer5 band. Double digestion with Fse I/Hind III is expected to release the aad-1 PTU fragment of 3361 bp that hybridizes to the ZmPer5 terminator probe (Table 2). This 3361 bp band and an additional non-specific hybridization band of ~2100 bp were detected by ZmPer5 terminator probe following Fse I/Hind III digestion. The additional ~2100 bp band is the non-specific binding of the ZmPer5 terminator probe to the corn endogenous gene since this band is present in all sample lanes including the negative controls. Results obtained with these digestions of the DAS-40278-9 sample followed by ZmUbi1 promoter and ZmPer5 terminator probe hybridization further confirmed that a single copy of an intact aad-1 PTU from plasmid pDAS 1740 was inserted into the corn genome of event DAS-40278-9.

Restriction enzymes, Nco I and Sac I, were selected to characterize the rest of the components from pDAS1740/Fsp I fragment in AAD-1 corn event DAS-40278-9 (Table 2). DNA sequences of components RB7 Mar v3 and RB7 Mar v4 have over 99.7% identity, therefore DNA probes specific for RB7 Mar v3 or RB7 Mar v4 were expected to hybridize to DNA fragments containing either version of the RB7 Mar. Two border fragments of >2764 bp and >3472 bp were expected to hybridize with RB7 Mar v4 and RB7 Mar v3 probes following Nco I digestion (Table 2). Two hybridization bands of ~4000 bp and ~6300 bp were observed with either RB7 Mar v4 or RB7 Mar v3 probe after Nco I digestion in DAS-40278-9 samples. Similarly, two border fragments of >1847 bp and >4389 bp were predicted with RB7 Mar v4 and RB7 Mar v3 probes following Sac I digestion (Table 2). Hybridization bands of ~1900 bp and ~16000 bp were detected in DAS-40278-9 samples with RB7 Mar v4 or RB7 Mar v3 probe after Sac I digestion.

Taken together, the Southern hybridization results obtained with these element probes indicated that the DNA inserted in corn event DAS-40278-9 contains an intact aad-1 PTU along with the matrix attachment regions RB7 Mar v3 and RB7 Mar v4 at the 5' and 3' ends of the insert, respectively.

Example 2.8

Absence of Backbone Sequences

Equal molar ratio combination of three DNA fragments (Table 1) covering nearly the entire Fsp I backbone region (4867-7143 bp in plasmid pDAS 1740) of plasmid pDAS 1740 were used as the backbone probe to characterize AAD-1 corn event DAS-40278-9. Plasmid pDAS 1740/Fsp I fragment was used to generate event DAS-40278-9, therefore, no specific hybridization signal was expected with the backbone probe combination (Table 2) following any restriction enzyme digestion. It was confirmed that no specific hybridization signal was detected with backbone probe following Nco I or Sac I digestion in all DAS-40278-9 samples. Positive control lanes contained the expected hybridizing bands demonstrating that the probes were capable of hybridizing to any homologous DNA fragments if present in the samples. The data suggested that the insertion in corn event DAS-40278-9 did not include any vector backbone sequence outside of the Fsp I region from plasmid pDAS 1740.

Leaf samples from five distinct generations of the event DAS-40278-9 were used to conduct the Southern blot analysis for molecular characterization. The integration pattern was investigated using selected restriction enzyme digest and probe combinations to characterize the inserted gene, aad-1, as well as the non-coding regions including promoter, terminator of gene expression, and the matrix attachment regions.

Southern blot characterization of the DNA inserted into event DAS-40278-9 indicate that a single intact copy of the aad-1 PTU has been integrated into event DAS-40278-9. The molecular weights indicated by the Southern hybridization for the combination of the restriction enzyme and the probe were unique for the event, and established its identification patterns. The hybridization pattern is identical across all five generations, indicating that the insert is stable in the corn genome. Hybridization with probes covering the backbone region beyond the pDAS1740/Fsp I transformation fragment from plasmid pDAS1740 confirms that no vector backbone sequences have been incorporated into the event DAS-40278-9.

Example 3

Cloning and Characterization of DNA Sequence in the Insert and the Flanking Border Regions of Corn Event DAS-40278-9

To characterize the inserted DNA and describe the genomic insertion site, DNA sequences of the insert and the border regions of event DAS-40278-9 were determined. In total, 8557 bp of event DAS-40278-9 genomic sequence were confirmed, comprising 1873 bp of 5' flanking border sequence, 1868 bp of 3' flanking border sequence, and 4816 bp of DNA insert. The 4816 bp DNA insert contains an intact aad-1 expression cassette, a 259 bp partial MAR v3 on the 5' terminus, and a 1096 bp partial MAR v4 on the 3' terminus. Sequence analysis revealed a 21 bp insertion at 5'-integration junction and a two base pair deletion from the insertion locus of the corn genome. A one base pair insertion was found at 3'-integration junction between the corn genome and the DAS-40278-9 insert. Also, a single base change (T to C) was found in the insert at position 5212 in the non-coding region of the 3' UTR. None of these changes affect the open reading frame composition of the aad-1 expression cassette.

PCR amplification based on the event DAS-40278-9 insert and border sequences confirmed that the border regions were of corn origin and that the junction regions could be used for event-specific identification of DAS-40278-9. Analysis of the sequence spanning the junction regions indicated that no novel open reading frames (ORF>=200 codons) resulted from the DNA insertion in event DAS-40278-9 and also no genomic open reading frames were interrupted by the DAS-40278-9 integration in the native corn genome. Overall, characterization of the insert and border sequences of the AAD-1 corn event DAS-40278-9 indicated that a single intact copy of the aad-1 expression cassette was integrated into the native corn genome.

Example 3.1

Genomic DNA Extraction and Quantification

Genomic DNA was extracted from lyophilized or freshly ground leaf tissues using a modified CTAB method. DNA samples were dissolved in 1×TE (10 mM Tris pH8.0, 1 mM EDTA) (Fluka, Sigma, St. Louis, Mo.) and quantified with the Pico Green method according to manufacturer's instructions (Molecular Probes, Eugene, Oreg.). For PCR analysis, DNA samples were diluted with molecular biology grade water (5 PRIME, Gaithersburg, Md.) to result in a concentration of 10-100 ng/µL.

Example 3.2

PCR Primers

Figure 4:
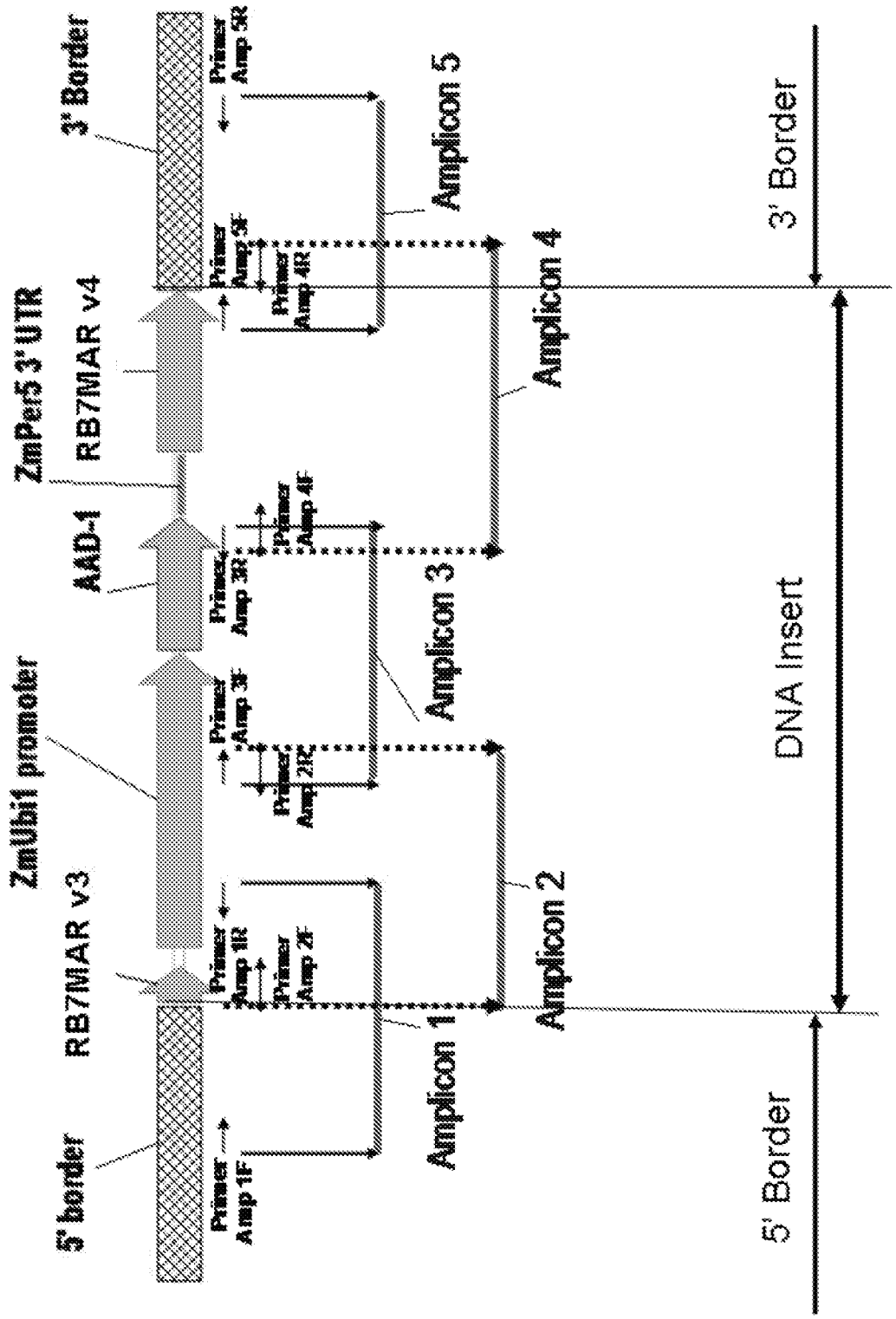
FIG. 4 shows amplicons, primers, and a cloning strategy for the DNA insert and borders for DAS-40278-9.
Figure 5:
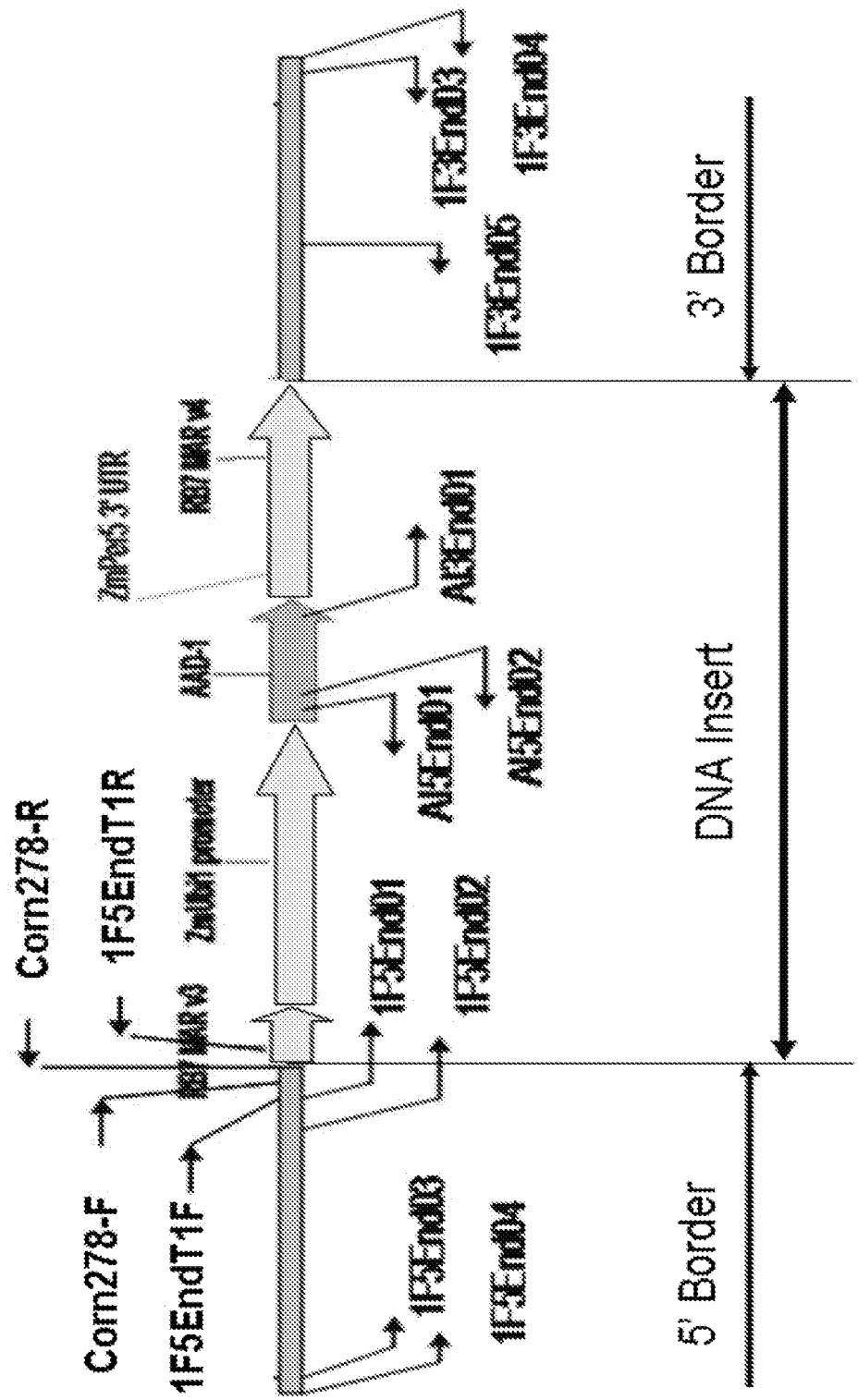
FIG. 5 illustrates primer locations with respect to the insert and borders for DAS-40278-9.
Figure 7:
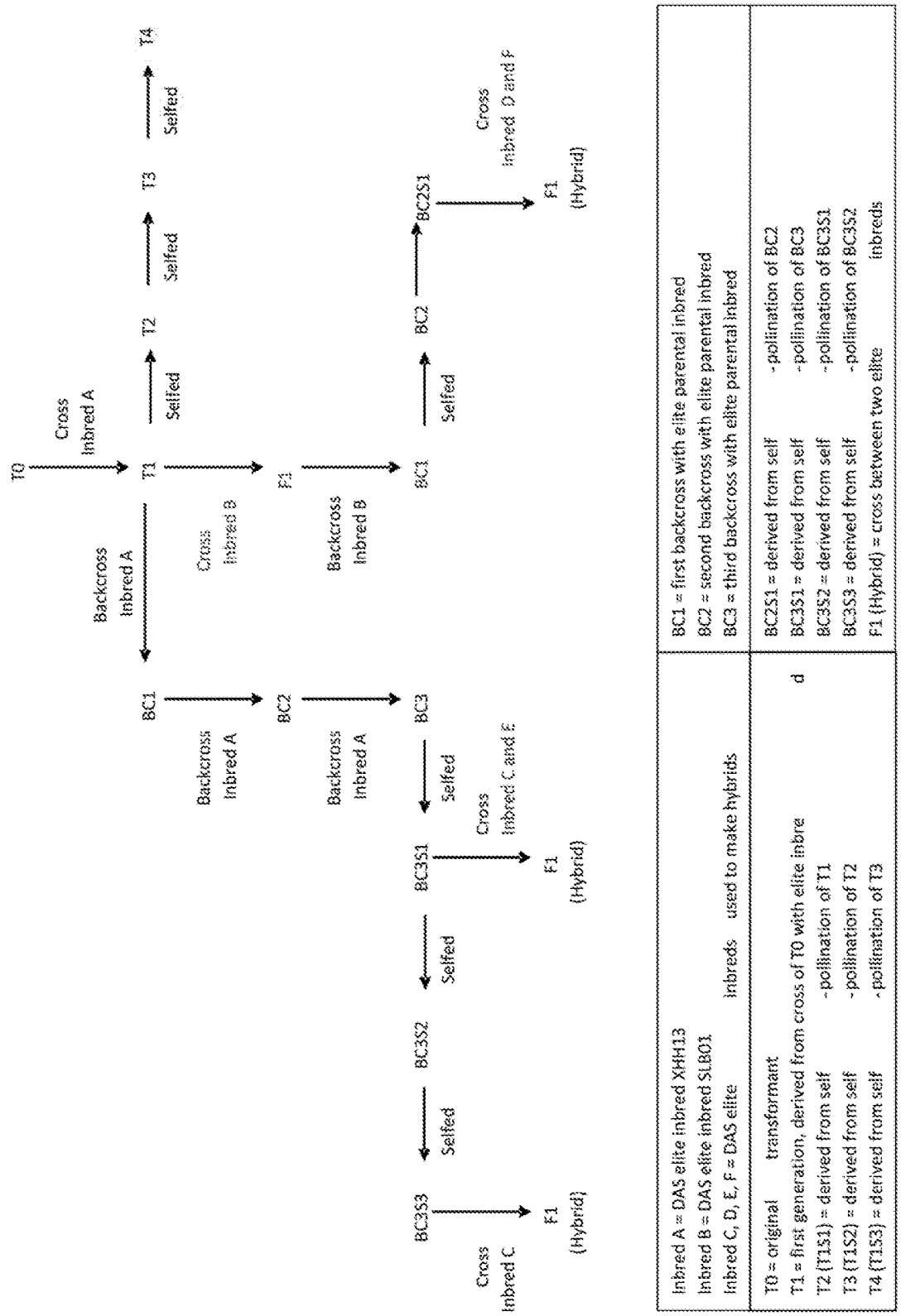
FIG. 7 is a breeding diagram referenced in Example 7.

Table 3 lists the primer sequences that were used to clone the DNA insert and the flanking border regions of event DAS-40278-9, with positions and descriptions marked in FIG. 4. Table 4 lists the primer sequences that were used to confirm the insert and border sequences. The primer positions were marked in FIGS. 4 and 5, respectively. All primers were synthesized by Integrated DNA Technologies, Inc. (Coralville, Iowa). Primers were dissolved in water (5 PRIME, Gaithersburg, Md.) to a concentration of 100 µM for the stock solution and diluted with water to a concentration of 10 µM for the working solution.

TABLE 3

List of primer sequences used in the cloning of the insert in Corn Event DAS-40278-9 and flanking border sequence.

| Primer Name | Size (bp) | Location (bp) | Sequence | Purpose |
|---|---|---|---|---|
| 5End3812_A | 26 | 2231-2256 (−) | Seq ID No: 1:<br>5'TGCACTGCAGGTCGACTCTAGAGGAT-3' | Primary PCR for 5' border sequence |
| 5End3812_B | 23 | 2110-2132 (−) | Seq ID No: 2:<br>5'-GCGGTGGCCACTATTTTCAGAAG-3' | Second PCR for 5' border sequence |
| 3End3812_C | 26 | 5535-5560 (+) | Seq ID No: 3:<br>5'-TTGTTACGGCATATATCCAATAGCGG-3' | Primary PCR for 3' border sequence |
| 3End3812_D | 26 | 5587-5612 (+) | Seq ID No: 4:<br>5'-CCGTGGCCTATTTTCAGAAGAAGTTC-3' | Secondary PCR for 3' border sequence |
| Amp 1F | 23 | 736-758 (+) | Seq ID NO: 5:<br>5'-ACAACCATATTGGCTTTGGCTGA-3' | Amplification of the insert, Amplicon 1, used with Amp 1R |
| Amp 1R | 28 | 2475-2502 (−) | Seq ID NO: 6:<br>5'CCTGTTGTCAAAATACTCAATTGTCCTT-3' | Amplification of the insert, Amplicon 1, used with Amp 1F |
| Amp 2F | 23 | 1696-1718 (+) | Seq ID NO: 7:<br>5'-CTCCATTCAGGAGACCTCGCTTG-3' | Amplification of the insert, Amplicon 2, used with Amp 2R |
| Amp 2R | 23 | 3376-3398 (−) | Seq ID NO: 8:<br>5'GTACAGGTCGCATCCGTGTACGA-3' | Amplification of the insert, Amplicon 2, used with Amp 2F |
| Amp 3F | 25 | 3254-3278 (+) | Seq ID NO: 9:<br>5'-CCCCCCCTCTCTACCTTCTCTAGAT-3' | Amplification of the insert, Amplicon 3, used with Amp 3R |
| Amp 3R | 23 | 4931-4953 (−) | Seq ID NO: 10:<br>5'-GTCATGCCCTCAATTCTCTGACA-3' | Amplification of the insert, Amplicon 3, used with Amp 3F |

TABLE 3-continued

List of primer sequences used in the cloning of the insert in
Corn Event DAS-40278-9 and flanking border sequence.

| Primer Name | Size (bp) | Location (bp) | Sequence | Purpose |
|---|---|---|---|---|
| Amp 4F | 23 | 4806-4828 (+) | Seq ID NO: 11:<br>5'-GTCGCTTCAGCAACACCTCAGTC-3' | Amplification of the insert, Amplicon 4, used with Amp 4R |
| Amp 4R | 23 | 6767-6789 (-) | Seq ID NO: 12:<br>5'-AGCTCAGATCAAAGACACACCCC-3' | Amplification of the insert, Amplicon 5, used with Amp 5F |
| Amp 5F | 28 | 6300-6327 (+) | Seq ID NO: 13:<br>5'-TCGTTTGACTAATTTTTCGTTGATGTAC-3' | Amplification of the insert, Amplicon 5, used with Amp 5R |
| Amp 5R | 23 | 7761-7783 (-) | Seq ID NO: 14:<br>5'-TCTCACTTTCGTGTCATCGGTCG-3' | Amplification of the insert, Amplicon 5, used with Amp 5F |

(+): Direct sequence;
(-): Complementary sequence;

TABLE 4

List of primer sequences used in the confirmation of corn genomic DNA

| Primer Name | Size (bp) | Location (bp) | Sequence | Purpose |
|---|---|---|---|---|
| 1F5End01 | 17 | 1716-1832 (+) | Seq ID NO: 15:<br>5'-CCAGCACGAACCATTGA-3' | Confirmation of 5' border genomic DNA, used with AI5End01 |
| 1F5End02 | 24 | 1629-1652 (+) | Seq ID NO: 16:<br>5'-CGTGTATATAAGGTCCAGAGGGTA-3' | Confirmation of 5' border genomic DNA, used with AI5End02 |
| AI5End01 | 17 | 4281-4297 (-) | Seq ID NO: 17:<br>5'-TTGGGAGAGAGGGCTGA-3' | Confirmation of 5' border genomic DNA, used with 1F5End01 |
| AI5End02 | 20 | 4406-4426 (-) | Seq ID NO: 18:<br>5'-TGGTAAGTGTGGAAGGCATC-3' | Confirmation of 5' border genomic DNA, used with 1F5End02 |
| 1F3End03 | 20 | 8296-8315 (-) | Seq ID NO: 19:<br>5'-GAGGTACAACCGGAGCGTTT-3' | Confirmation of genomic DNA, used with 1F5End03 |
| 1F3End04 | 19 | 8149-8437 (-) | Seq ID NO: 20:<br>5'-CCGACGCTTTTCTGGAGTA-3' | Confirmation of genomic DNA, used with 1F5End04 |
| 1F5End03 | 22 | 378-399 (+) | Seq ID NO: 21:<br>5'-TGTGCCACATAATCACGTAACA-3' | Confirmation of genomic DNA, used with 1F3End03 |
| 1F5End04 | 20 | 267-286 (+) | Seq ID NO: 22:<br>5'-GAGACGTATGCGAAAATTCG-3' | Confirmation of genomic DNA, used with 1F3End04 |
| AI3End01 | 22 | 4973-4994 (+) | Seq ID NO: 23:<br>5'-TTGCTTCAGTTCCTCTATGAGC-3' | Confirmation of 3' border genomic DNA, used with 1F3End05 |
| 1F3End05 | 19 | 7060-7078 (-) | Seq ID NO: 24:<br>5'-TCCGTGTCCACTCCTTTGT-3' | Confirmation of 3' border genomic DNA, used with AI3End01 |
| 1F5End T1F | 22 | 2033-2054 (-) | Seq ID NO: 25:<br>5'-GCAAAGGAAAACTGCCATTCTT-3' | 278 specific sequence amplification at 5' junction |
| 1F5EndT1R | 20 | 1765-1784 (+) | Seq ID NO: 26:<br>5'-TCTCTAAGCGGCCCAAACTT-3' | 278 specific sequence amplification at 5' junction |
| Corn278-F | 23 | 1884-1906 (-) | Seq ID NO: 27:<br>5'-ATTCTGGCTTTGCTGTAAATCGT-3' | 278 specific sequence amplification at 5' junction |

TABLE 4-continued

List of primer sequences used in the confirmation of corn genomic DNA

| Primer Name | Size (bp) | Location (bp) | Sequence | Purpose |
|---|---|---|---|---|
| Corn278-R | 24 | 1834-1857 (+) | Seq ID NO: 28:<br>5'-TTACAATCAACAGCACCGTACCTT | 278 specific sequence amplification at 5' junction |

(+): Direct sequence;
(−): Complementary sequence;

Example 3.3

Genome Walking

The GenomeWalker™ Universal Kit (Clontech Laboratories, Inc., Mountain View, Calif.) was used to clone the 5' and 3' flanking border sequences of corn event DAS-40278-9. According to the manufacturer's instruction, about 2.5 μg of genomic DNA from AAD-1 corn event DAS-40278-9 was digested overnight with EcoR V, Stu I (both provided by the kit) or Sca I (New England Biolabs, Ipswich, Mass.). Digested DNA was purified using the DNA Clean & Concentrator™-25 (ZYMO Research, Orange, Calif.) followed by ligation to GenomeWalker™ adaptors to construct GenomeWalker™ libraries. Each GenomeWalker™ library was used as DNA template for primary PCR amplification with the adaptor primer AP1, provided in the kit, and each construct-specific primer 5End3812_A and 3End3812_C. One microliter of 1:25 dilution of primary PCR reaction was then used as template for secondary PCR amplification with the nested adaptor primer AP2 and each nested construct-specific primer 5End3812_B and 3End3812_D. TaKaRa LA Taq™ HS (Takara Bio Inc., Shiga, Japan) was used in the PCR amplification. In a 50 μL PCR reaction, 1 μL of DNA template, 8 μL of 2.5 mM of dNTP mix, 0.2 μM of each primer, 2.5 units of TaKaRa LA Taq™ HS DNA Polymerase, 5 μl of 10×LA PCR Buffer II (Mg2+ plus), and 1.5 μL of 25 mM $MgCl_2$ were used. Specific PCR conditions are listed in Table 5.

TABLE 5

Conditions for Genome Walking of the AAD-1 Corn Event DAS-40278-9 to Amplify the Flanking Border Regions

| Target Sequence | Primer Set | Pre-denature (° C./min) | Denature (° C./sec.) | Anneal (° C./sec.) | Extension (° C./min:sec) | Denature (° C./sec) | Anneal (° C./sec.) | Extension (° C. /min:sec) | Final Extension (° C./min) |
|---|---|---|---|---|---|---|---|---|---|
| 5' border | 5End3812_A/ AP1 | 95/3 | 95/30 | $68^{-0.5/cycle} \to 64/30$<br>8 cycles | 68/10:00 | 95/30 | 64/30<br>22 cycles | 68/10:00 | 72/10 |
| 5' border (nested) | 5End3812_B/ AP2 | 95/3 | 95/30 | $68^{-0.5/cycle} \to 64/30$<br>8 cycles | 68/10:00 | 95/30 | 64/30<br>22 cycles | 68/10:00 | 72/10 |
| 3' border | 3End3812_C/ AP1 | 95/3 | 95/30 | $68^{-0.5/cycle} \to 64/30$<br>8 cycles | 68/10:00 | 95/30 | 64/30<br>22 cycles | 68/10:00 | 72/10 |
| 3' border (nested) | 3End3812_D/ AP2 | 95/3 | 95/30 | $68^{-0.5/cycle} >64/30$<br>8 cycles | 68/10:00 | 95/30 | 64/30<br>22 cycles | 68/10:00 | 72/10 |

Example 3.4

Conventional PCR

Standard PCR was used to clone and confirm the DNA insert and border sequence in the corn event DAS-40278-9. TaKaRa LA Taq™ (Takara Bio Inc., Shiga, Japan), HotStarTaq DNA Polymerase (Qiagen, Valencia, Calif.), Expand High Fidelity PCR System (Roche Diagnostics, Inc., Indianapolis, Ind.), or the Easy-A® High-Fidelity PCR Cloning Enzyme & Master Mix (Stratagene, LaJolla, Calif.) was used for conventional PCR amplification according to the manufacturer's recommended procedures. Specific PCR conditions and amplicon descriptions are listed in Table 6.

TABLE 6

Conditions for Standard PCR Amplification of the Border Regions in the Corn Event DAS-40278-9

| Target Sequence | Primer Set | Pre-denature (° C./min) | Denature (° C./sec.) | Anneal (° C./sec.) | Extension (° C./min:sec) | Final Extension (° C./min) |
|---|---|---|---|---|---|---|
| 5' border | 1F5End01/ AI5End01 | 95/3 | 95/30 | 60/30 35 cycles | 68/5:00 | 72/10 |
| 5' border | 1F5End02/ AI5End02 | 95/3 | 95/30 | 60/30 35 cycles | 68/5:00 | 72/10 |
| Across the insert locus | 1F3End03/ 1F5End03 | 95/3 | 95/30 | 60/30 35 cycles | 68/5:00 | 72/10 |
| Across the insert locus | 1F3End04/ 1F5End04 | 95/3 | 95/30 | 60/30 35 cycles | 68/5:00 | 72/10 |
| 5' junction (Amplicon 1) | Amp 1F/ Amp 1R | 95/2 | 94/60 | 55/60 35 cycles | 72/2:00 | 72/10 |
| Amplicon 2 | Amp 1F/ Amp 1R | 95/2 | 94/60 | 55/60 35 cycles | 72/2:00 | 72/10 |
| Amplicon 3 | Amp 1F/ Amp 1R | 95/2 | 94/60 | 55/60 35 cycles | 72/2:00 | 72/10 |
| Amplicon 4 | Amp 1F/ Amp 1R | 95/2 | 94/60 | 55/60 35 cycles | 72/2:00 | 72/10 |
| 3' junction (Amplicon 5) | Amp 1F/ Amp 1R | 95/2 | 94/60 | 55/60 35 cycles | 72/2:00 | 72/10 |
| 3' border | 1F3End05/ A13End01 | 95/3 | 95/30 | 60/30 35 cycles | 68/5:00 | 72/10 |

Example 3.5

PCR Product Detection, Purification, Sub-Cloning of PCR Products, and Sequencing PCR products were inspected by electrophoresis using 1.2% or 2% E-gel (Invitrogen, Carlsbad, Calif.) according to the product instruction. Fragment size was estimated by comparison with the DNA markers. If necessary, PCR fragments were purified by excising the fragments from 1% agarose gel in 1×TBE stained with ethidium bromide, using the QiAquick Gel Extraction Kit (Qiagen, Carlsbad, Calif.).

PCR fragments were sub-cloned into the pCR®4-TOPO® using TOPO TA Cloning® Kit for Sequencing (Invitrogen, Carlsbad, Calif.) according to the product instruction. Specifically, two to five microliters of the TOPO® cloning reaction was transformed into the One Shot chemically competent TOP10 cells following the manufacturer's instruction. Cloned fragments were verified by miniprepa-ration of the plasmid DNA (QIAprep Spin Miniprep Kit, Qiagen, Carlsbad, Calif.) followed by restriction digestion with EcoR I or by direct colony PCR using T3 and T7 primers, provided in the kit. Plasmid DNA or glycerol stocks of the selected colonies were then sent for sequencing.

After sub-cloning, the putative target PCR products were sequenced initially to confirm that the expected DNA fragments had been cloned. The colonies containing appropriate DNA sequences were selected for primer walking to determine the complete DNA sequences. Sequencing was performed by Cogenics (Houston, Tex.).

Final assembly of insert and border sequences was completed using Sequencher software (Version 4.8 Gene Codes Corporation, Ann Arbor, Mich.). Annotation of the insert and border sequences of corn event DAS-40278-9 was performed using the Vector NTI (Version 10 and 11, Invitrogen, Carlsbad, Calif.).

Homology searching was done using the BLAST program against the GenBank database. Open reading frame (ORF) analysis using Vector NTI (Version 11, Invitrogen) was performed to identify ORFs (>=200 codons) in the full insert and flanking border sequences.

Example 3.6

5' End Border Sequence

A DNA fragment was amplified from each corn event DAS-40278-9 GenomeWalker™ library using the specific nested primer set for 5' end of the transgene. An approximately 800 bp PCR product was observed from both the event DAS-40278-9 EcoR V and Stu I GenomeWalker™ libraries. The Sca I GenomeWalker™ library generated a product around 2 kb. The fragments were cloned into pCR® 4-TOPO and six colonies from each library were randomly picked for end sequencing to confirm the insert contained the expected sequences. Complete sequencing by primer walking of the inserts revealed that the fragments amplified from corn event DAS-40278-9 Stu I, EcoR V, and Sca I GenomeWalker™ libraries were 793, 822, and 2132 bp, respectively. The DNA fragments generated from the Stu I and EcoR V GenomeWalker™ libraries were a 100% match to the DNA fragment generated from Sca GenomeWalker™ library, suggesting that these DNA fragments were amplified from the 5' region of the transgene insert. BLAST search of the resultant 1873 bp corn genomic sequence indicated a high similarity to the sequence of a corn BAC clone. Moreover, sequence analysis of the insertion junction indicated that 917 bp of the MAR v3 at its 5' end region was truncated compared to the plasmid pDAS1740/Fsp I fragment, leaving a 259 bp partial MAR v3 at the 5' region of the aad-1 expression cassette.

Example 3.7

3' End Border Sequence

A DNA fragment with size of approximately 3 kb was amplified from corn event DAS-40278-9 Stu I GenomeWalker™ library using the specific nested primer set for the 3' end of the transgene. The DNA fragment was cloned into pCR®4-TOPO® and ten colonies were randomly picked for end sequencing to confirm the insertion of the expected sequences. Three clones with the expected inserts were completely sequenced, generating a 2997 bp DNA fragment. Sequence analysis of this DNA fragment revealed a partial MAR v4 element (missing 70 bp of its 5' region) and 1867 bp corn genomic sequence. BLAST search showed the 1867 bp genomic DNA sequence was a 100% match to sequence in the same corn BAC clone as was identified with the 5' border sequence.

Example 3.8

DNA Insert and Junction Sequence

The DNA insert and the junction regions were cloned from corn event DAS-40278-9 using PCR based methods as previously described. Five pairs of primers were designed based on the 5' and 3' flanking border sequences and the expected transgene sequence. In total, five overlapping DNA fragments (Amplicon 1 of 1767 bp, Amplicon 2 of 1703 bp, Amplicon 3 of 1700 bp, Amplicon 4 of 1984 bp, and Amplicon 5 of 1484 bp) were cloned and sequenced (FIG. 4). The whole insert and flanking border sequences were assembled based on overlapping sequence among the five fragments. The final sequence confirms the presence of 4816 bp of the DNA insert derived from pDAS1740/Fsp I, 1873 bp of the 5' flanking border sequence, and 1868 bp of 3' flanking border sequence. The 4816 bp DNA insert contains an intact aad-1 expression cassette, a 259 bp partial MAR v3 on the 5' terminus, and a 1096 bp partial MAR v4 on the 3' terminus (Seq ID No: 29).

At least two clones for each primer pair were used for primer walking in order to obtain the complete sequence information on the DNA insert and its border sequences. Sequence analysis indicated a 21 bp insertion at 5'-integration junction between corn genome DNA and the integrated partial MAR v3 from the pDAS1740/Fsp I. BLAST search and Vector NTI analysis results indicated that the 21 bp insert DNA did not demonstrate homology to any plant species DNA or the pDAS1740 plasmid DNA. A single base pair insertion was found at the 3'-integration junction between corn genome DNA and the partial MAR v4 from the pDAS 1740/Fsp I. DNA integration also resulted in a two base pair deletion at the insertion locus of the corn genome (FIG. 6). In addition, one nucleotide difference (T to C) at the position of 5212 bp was observed in the non-translated 3' UTR region of the DNA insert (Seq ID No: 29). However, none of these changes seem to be critical to aad-1 expression or create any new ORFs (>=200 codons) across the junctions in the insert of DAS-40278-9.

Example 3.9

Confirmation of Corn Genomic Sequences

To confirm the insertion site of event DAS-40278-9 transgene in the corn genome, PCR amplification was carried out with different pairs of primers (FIG. 4). Genomic DNA from event DAS-40278-9 and other transgenic or non-transgenic corn lines was used as a template. Two aad-1 specific primers, A15End01 and A15End02, and two primers designed according to the 5' end border sequence, 1F5End01 and 1F5End02, were used to amplify DNA fragments spanning the aad-1 gene to 5' end border sequence. Similarly, to amplify a DNA fragment spanning the aad-1 to 3' end border sequence, 1F3End05 primer derived from the 3' end border sequence and aad-1 specific AI3End01 primer were used. DNA fragments with expected sizes were amplified only from the genomic DNA of AAD-1 corn event DAS-40278-9, with each primer pair consisting of one primer located on the flanking border of AAD-1 corn event DAS-40278-9 and one aad-1 specific primer. The control DNA samples did not yield PCR products with the same primer pairs indicating that the cloned 5' and 3' end border sequences are indeed the upstream and downstream sequence of the inserted aad-1 gene construct, respectively. It is noted that a faint band with size of about 8 kb was observed in all the corn samples including AAD-1 corn event DAS-40278-9, AAD-1 corn event DAS-40474 and non transgenic corn line XHH13 when the primer pair of 1F5End01 and AI5End01 were used for PCR amplification. An observed faint band (on a prepared gel) could be a result of nonspecific amplification in corn genome with this pair of primers.

To further confirm the DNA insertion in the corn genome, two primers located at the 5' end border sequence, 1F5End03 and 1F5End04, and two primers located at the 3' end border sequence, 1F3End03 and 1F3End04, were used to amplify DNA fragments spanning the insertion locus. PCR amplification with either the primer pair of 1F5End03/1F3End03 or the primer pair of 1F5End04/1F3End04 resulted in a fragment with expected size of approximately 8 kb from the genomic DNA of AAD-1 corn event DAS-40278-9. In contrast, no PCR products resulted from the genomic DNA of AAD-1 corn event DAS-40474-7 or the non-transgenic corn line XHH13. Given that AAD-1 corn event DAS-40278-9 and event DAS-40474-7 were generated by transformation of Hill, followed by backcrossing the original transgenic events with the corn line XHH13, the majority of genome in each of these two events is theoretically from the corn line XHH13. It is very likely that only the flanking border sequences close to the aad-1 transgene are carried over from the original genomic DNA and preserved during the AAD-1 event introgression process, while other regions of genome sequences might have been replaced by the genome sequences of XHH13. Therefore, it is not surprising that no fragments were amplified from the genomic DNA of AAD-1 corn event DAS-40474-7 and XHH13 with either the primer pair of 1F5End03/1F3End03 or the primer pair of 1F5End04/1F3End04. Approximately 3.1 and 3.3 kb fragments were amplified with the primer pair of 1F5End03/1F3End03 and 1F5End04/1F3End04 respectively in the genomic DNA of the corn lines Hill and B73 but not in the corn line A188. The results indicate that the border sequences originated from the genome of the corn line B73.

Additional cloning of corn genomic DNA from B73/HiII was performed to ensure validity of the flanking border sequences. The PCR amplified fragments were sequenced in order to prove the insert DNA region integrated into the specific location of B73/HiII genomic DNA. Primers were designed based on the sequence obtained. Primer set Amp 1F/Amp 5R was used to amplify a 2212 bp fragment spanning the 5' to 3' junctions from native B73/HiII genome without insert DNA. Sequence analysis revealed that there was a two base pair deletion from the native B73 genome in the transgene insertion locus. Analysis of the DNA sequences from the cloned native B73 genomic fragment identified one ORF (>=200 codons) located downstream of the 3'-integration junction region. Additionally, there are no other ORFs across the original locus where the AAD-1 corn event DAS-40278-9 integrated. BLAST search also confirmed that both 5' end and 3' end border sequences from the event DAS40278-9 are located side by side on the same corn BAC clone.

Given the uniqueness of the 5'-integration junction of the AAD-1 corn event DAS-40278-9, two pairs of specific PCR primers, 1F5EndT1F/1F5EndT1R and Corn278-F/Corn278-R, were designed to amplify this insert-to-plant genome junction. As predicted, the desired DNA fragment was only generated in the genomic DNA of the AAD-1 corn event DAS-40278-9 but not any other transgenic or non-transgenic corn lines. Therefore, those two primer pairs can be used as AAD-1 corn event DAS-40278-9 event-specific identifiers.

Example 4

Genomic Characterization Via Flanking SSR Markers of DAS-40278-9

To characterize and describe the genomic insertion site, marker sequences located in proximity to the insert were determined. A panel of polymorphic SSR markers were used to identify and map the transgene location. Event pDAS 1740-278 is located on chromosome 2 at approximately 20 cM between SSR markers UMC1265 and MMC0111 at approximately 20 cM on the 2008 DAS corn linkage map. Table 6A summarizes the primer information for these two makers found to be in close proximity to transgene pDAS1740-278.

and 0.3 units of HotStart Taq DNA polymerase (Qiagen, Valencia, Calif.). Amplification was performed in a GeneAmp PCR System 9700 with a 384-dual head module (Applied Biosystems, Foster City, Calif.). The amplification program was as follows: (1) initial activation of Taq at 95° C. for 12 minutes; (2) 30 sec at 94° C.; (3) 30 sec at 55° C.; (4) 30 sec at 72° C.; (5) repeat steps 2-4 for 40 cycles; and (6) 30 min final extension at 72° C. The PCR products for each SSR marker panel were multiplexed together by adding 2 µl of each PCR product from the same plant to sterile deionized water for a total volume of 60 µl. Of the multiplexed PCR products, 0.5 ul were stamped into 384-well loading plates containing 5 µl of loading buffer comprised of a 1:100 ratio of GeneScan 500 base pair LIZ size standard and ABI HiDi Formamide (Applied Biosystems, Foster City, Calif.). The samples were then loaded onto an ABI Prism 3730x1 DNA Analyzer (Applied Biosystems, Foster City, Calif.) for capillary electrophoresis using the manufacturer's recommendations with a total run time of 36 minutes. Marker data was collected by the ABI Prism 3730x1 Automated Sequencer Data Collection software Version 4.0 and

TABLE 6A

Primer names, dye labels, locus positions, forward and reverse primer sequences, and significant notes for flanking makers associated with event pDAS1740-278.

| Primer Name | Label | Chr | ~cM | Bin | Forward Primer | Reverse Primer | Notes |
|---|---|---|---|---|---|---|---|
| umc1265 | NED | 2 | 20 | 2.02 | Seq ID No: 5'-GCCTAGTCGCCTA CCCTACCAAT-3' | Seq ID No: 5'-TGTGTTCTTGATT GGGTGAGACAT-3' | Left flanking marker |
| mmc0111 | FAM | 2 | 20 | 2.03 | Seq ID No: 32 5'-TACTGGGGATTAG AGCAGAAG-3' | Seq ID No: 33: 5'-AATCTATGTGTGA ACAGCAGC-3; | Right flanking marker |

Example 4.1 gDNA Isolation gDNA was extracted from leaf punches using the DNEasy 96 Plant Test Kit (Qiagen, Valencia, Calif.). Modifications were made to the protocol to accommodate for automation. Isolated gDNA was quantified using the PicoGreen® dye from Molecular Probes, Inc. (Eugene, Oreg.). The concentration of gDNA was diluted to 5 ng/µl for all samples using sterile deionized water.

Example 4.2

Screening of gDNA with Markers

The diluted gDNA was genotyped with a subset of simple sequence repeats (SSR) markers. SSR markers were synthesized by Applied Biosystems (Foster City, Calif.) with forward primers labeled with either 6-FAM, HEX/VIC, or NED (blue, green and yellow, respectively) fluorescent tags. The markers were divided into groups or panels based upon their fluorescent tag and amplicon size to facilitate post-PCR multiplexing and analysis.

PCR was carried out in 384-well assay plates with each reaction containing 5 ng of genomic DNA, 1.25×PCR buffer (Qiagen, Valencia, Calif.), 0.20 µM of each forward and reverse primer, 1.25 mM MgCl₂, 0.015 mM of each dNTP, extracted via GeneMapper 4.0 software (Applied Biosystems) for allele characterization and fragment size labeling.

Example 4.3

SSR Marker Results

The primer data for the flanking markers which were identified in the closest proximity to the transgene are listed in Table 6. The two closest associated markers, UMC1265 and MMC0111, are located approximately 20 cM away from the transgene insert on chromosome 2.

Example 5

Characterization of Acid-1 Protein in Event DAS-40278-9

The biochemical properties of the recombinant aad-1 protein derived from the transgenic maize event DAS-40278-9 were characterized. Sodium dodecyl sulfate polyacrylamide gel electrophoresis (SDS-PAGE, stained with Coomassie blue and glycoprotein detection methods), western blot, immunodiagnostic test strip assays, matrix assisted laser desorption/ionization time-of-flight mass spectrometry (MALDI-TOF MS) and protein sequencing analysis by tandem MS were used to characterize the biochemical properties of the protein.

Example 5.1

Immunodiagnostic Strip Assay

The presence of the aad-1 protein in the leaf tissue of DAS-40278-9 was confirmed using commercially prepared immunodiagnostic test strips from American Bionostica. The strips were able to discriminate between transgenic and nontransgenic plants by testing crude leaf extracts (data not shown). The non-transgenic extracts (XHH13) did not contain detectable amounts of immunoreactive protein. This result was also confirmed by western blot analysis.

To test for the expression of the aad-1 protein, an immunodiagnostic strip analysis was performed. Four leaf punches were collected from each plant for XHH13 (control plant) and event DAS-40278-9 bp pinching the tissue between the snap-cap lids of individually labeled 1.5-mL microfuge tubes. Upon receipt in the lab, 0.5 mL of aad-1 extraction buffer (American Bionostica, Swedesboro, N.J.) was added to each tube, and the tissue was homogenized using a disposable pestle followed by shaking the sample for ~10 seconds. After homogenization, the test strip was placed in the tube and allowed to develop for ~5 minutes. The presence or absence of the aad-1 protein in the plant extract was confirmed based on the appearance (or lack of appearance) of a test line on the immunodiagnostic strip. Once the expression of the aad-1 protein was confirmed for the transgenic event, the maize stalk tissue was harvested and lyophilized and stored at approximately −80° C. until use.

Example 5.2

Purification of the aad-1 Protein from Corn

Immuno-purified, maize-derived aad-1 protein (molecular weight: ~33 kDa) or crude aqueous extracts from corn stalk tissue were prepared. All leaf and stalk tissues were harvested and transported to the laboratory as follows: The leaves were cut from the plant with scissors and placed in cloth bags and stored at approximately −20° C. for future use. Separately, the stalks were cut off just above the soil line, placed in cloth bags and immediately frozen at approximately −80° C. for ~6 hours. The stalks were then placed in a lyophilizer for 5 days to remove water. Once the tissues were completely dried they were ground to a fine powder with dry ice and stored at approximately −80° C. until needed.

The maize-derived aad-1 protein was extracted from lyophilized stalk tissue in a phosphate-based buffer (see Table 7 for buffer components) by weighing out ~30 grams of lyophilized tissue into a chilled 1000 mL glass blender and adding 500 mL of extraction buffer. The tissue was blended on high for 60 seconds and the soluble proteins were harvested by centrifuging the sample for 20 minutes at 30,000×g. The pellet was re-extracted as described, and the supernatants were combined and filtered through a 0.45µ filter. The filtered supernatants were loaded at approximately +4° C. onto an anti- aad-1 immunoaffinity column that was conjugated with a monoclonal antibody prepared by Strategic Biosolution Inc. (MAb 473F1 85.1; Protein A purified; Lot #: 609.03C-2-4; 6.5 mg/mL (~35.2 mg total)) (Windham, Me.); Conjugated to CNBr-activated Sepharose 4B (GE Healthcare, Piscataway, N.J.). The non-bound proteins were collected and the column was washed extensively with pre-chilled 20 mM ammonium bicarbonate buffer, pH 8.0. The bound proteins were eluted with 3.5 M NaSCN, (Sigma, St. Louis, Mo.), 50 mM Tris (Sigma, St. Louis, Mo.) pH 8.0 buffer. Seven 5-mL-fractions were collected and fraction numbers 2 ⟶ 7 were dialyzed overnight at approximately +4° C. against 10 mM Tris, pH 8.0 buffer. The fractions were examined by SDS-PAGE and western blot and the remaining samples were stored at approximately +4° C. until used for subsequent analyses.

TABLE 7

The commercially available reference substances used in this study are listed in the following table:

| Reference Substance | Product Name | Lot Number | Assay | Reference |
|---|---|---|---|---|
| Soybean Trypsin Inhibitor | A component of the GelCode Glycoprotein Staining Kit | IA110577 | Glycosylation | Pierce Cat #: 1856274 |
| Horseradish Peroxidase | A component of the GelCode Glycoprotein Staining Kit | JG124509 | Glycosylation | Pierce Cat #: 1856273 |
| Bovine Serum Albumin Fraction V (BSA) | Pre-Diluted BSA Protein Assay Standard Set | FH71884A | Glycosylation, SDS-PAGE and Western Blot | Pierce Cat #: 23208 |
| Prestained Molecular Weight Markers | Novex Sharp Prestained Protein Markers | 469212 & 419493 | Western Blot | Invitrogen Cat #: LC5800, Molecular Weight Markers of 260, 160, 110, 80, 60, 50, 40, 30, 20, 15, 10 and 3.5 kDa |
| Molecular Weight Markers | Invitrogen Mark12 Protein Marker Mix | 39983 & 399895 | SDS-PAGE | Invitrogen Cat #: LC5677, Molecular Weight Markers of 200, 116.3, 97.4, 66.3, 55.4, 36.5, 31.0, 21.5, 14.4, 6.0, 3.5 and 2.5 kDa |

The protein that bound to the immunoaffinity column was examined by SDSPAGE and the results showed that the eluted fractions contained the aad-1 protein at an approximate molecular weight of 33 kDa. In addition, a western blot was also performed and was positive for the aad-1 protein. The maize-derived aad-1 protein was isolated from ~30 g of lyophilized stalk material.

Example 5.3

SDS-PAGE and Western Blot

Lyophilized tissue from event DAS-40278-9 and XHH13 stalk (~100 mg) were weighed out in 2-mL microfuge tubes and extracted with ~1 mL of PBST (Sigma, St. Louis, Mo.) containing 10% plant protease inhibitor cocktail (Sigma, St. Louis, Mo.). The extraction was facilitated by adding 4 small ball bearings and Geno-Grinding the sample for 1 minute. After grinding, the samples were centrifuged for 5 minutes at 20,000×g and the supernatants were mixed 4:1 with 5× Laemmli sample buffer (2% SDS, 50 mM Tris pH 6.8, 0.2 mg/mL bromophenol blue, 50% (w/w) glycerol containing 10% freshly added 2-mercaptoethanol) and heated for 5 minutes at ~100 ° C. After a brief centrifugation, 45 μL of the supernatant was loaded directly onto a BioRad Criterion SDS-PAGE gel (Bio-Rad, Hercules, Calif.) fitted in a Criterion Cell gel module. A positive reference standard of microbe-derived aad-1 was resuspended at 1 mg/mL in PBST pH 7.4 and further diluted with PBST. The sample was then mixed with Bio-Rad Laemmli buffer with 5% 2-mercaptoethanol and processed as described earlier. The electrophoresis was conducted with Tris/glycine/SDS buffer (Bio-Rad, Hercules, Calif.) at voltages of 150-200 V until the dye front approached the end of the gel. After separation, the gel was cut in half and one half was stained with Pierce GelCode Blue protein stain and the other half was electroblotted to a nitrocellulose membrane (Bio-Rad, Hercules, Calif.) with a Mini trans-blot electrophoretic transfer cell (Bio-Rad, Hercules, Calif.) for 60 minutes under a constant voltage of 100 volts. The transfer buffer contained 20% methanol and Tris/glycine buffer from Bio-Rad. For immunodetection, the membrane was probed with an aad-1 specific polyclonal rabbit antibody (Strategic Biosolution Inc., Newark, Del., Protein A purified rabbit polyclonal antibody Lot #: DAS F1 197-15 1, 1.6 mg/mL). A conjugate of goat anti-rabbit IgG (H+L) and alkaline phosphatase (Pierce Chemical, Rockford, Ill.) was used as the secondary antibody. SigmaFast BCIP/NBT substrate was used for development and visualization of the immunoreactive protein bands. The membrane was washed extensively with water to stop the reaction and a record of the results was captured with a digital scanner (Hewlett Packard, Palo Alto, Calif.).

In the *P. fluorescens*-produced aad-1 the major protein band, as visualized on Coomassie stained SDS-PAGE gels, was approximately 33 kDa. As expected, the corresponding maize-derived aad-1 protein (event DAS-40278-9) was identical in size to the microbe-expressed proteins. Predictably, the plant purified fractions contained a minor amount of non-immunoreactive impurities in addition to the aad-1 protein. The co-purified proteins were likely retained on the column by weak interactions with the column matrix or leaching of the monoclonal antibody off of the column under the harsh elution conditions. Other researchers have also reported the non-specific adsorption of peptides and amino acids on cyanogen-bromide activated Sepharose 4B immunoadsorbents (Kennedy and Barnes, 1983; Holroyde et al., 1976; Podlaski and Stem, 2008).

The *Pseudomonas*-derived aad-1 protein showed a positive signal of the expected size by polyclonal antibody western blot analysis. This was also observed in the DAS-40278-9 transgenic maize stalk extract. In the aad-1 western blot analysis, no immunoreactive proteins were observed in the control XHH13 extract and no alternate size proteins (aggregates or degradation products) were seen in the transgenic samples.

Example 5.4

Detection of Post-Translational Glycosylation

The immunoaffinity chromatography-purified, maize-derived aad-1 protein (Fraction #3) was mixed 4:1 with 5× Laemmli buffer. The microbe-derived aad-1, soybean trypsin inhibitor, bovine serum albumin and horseradish peroxidase were diluted with Milli-Q water to the approximate concentration of the plant-derived aad-1 and mixed with Bio-Rad Laemmli buffer. The proteins were then heated at ~95° C. for 5 minutes and centrifuged at 20000×g for 2 minutes to obtain a clarified supernatant. The resulting supernatants were applied directly to a Bio-RadCriterion Gel and electrophoresed with XT MES running buffer (Bio-Rad, Hercules, Calif.) essentially as described above except that the electrophoresis was run at 170 V for ~60 minutes. After electrophoresis, the gel was cut in half and one half was stained with GelCode Blue stain for total protein according to the manufacturers' protocol. After the staining was complete, the gel was scanned with a Molecular Dynamics densitometer to obtain a permanent visual record of the gel. The other half of the gel was stained with a GelCode Glycoprotein Staining Kit (Pierce Chemical, Rockford, Ill.) according to the manufacturers' protocol to visualize glycoproteins. The glycoproteins (with a detection limit as low as 0.625 ng per band) were visualized as magenta bands on a light pink background. After the glycoprotein staining was complete, the gel was scanned with a Hewlett Packard digital scanner to obtain a permanent visual record of the gel. After the image of the glycosylation staining was captured, the gel was stained with GelCode Blue to verify the presence of the non-glycosylated proteins. The results showed that both the maize- and microbe-derived aad-1 proteins had no detectable covalently linked carbohydrates. This result was also confirmed by peptide mass fingerprinting.

Example 5.5

Mass Spectrometry Peptide Mass Fingerprinting and Sequencing of Maize- and *Pseudomonas*-Derived aad-1

Mass Spectrometry analysis of the *Pseudomonas*- and maize-derived aad-1 was conducted. The aad-1 protein derived from transgenic corn stalk (event DAS-40278-9) was subjected to in-solution digestion by trypsin followed by MALDI-TOF MS and ESI-LC/MS. The masses of the detected peptides were compared to those deduced based on potential protease cleavage sites in the sequence of maize-derived aad-1 protein. The theoretical cleavage was generated in silico using Protein Analysis Worksheet (PAWS) freeware from Proteometrics LLC. The aad-1 protein, once denatured, is readily digested by proteases and will generate numerous peptide peaks.

In the trypsin digest of the transgenic-maize-derived aad-1 protein (event DAS-40278-9), the detected peptide fragments covered nearly the entire protein sequence lacking only one small tryptic fragment at the C-terminal end of the protein, $F^{248}$ to $R^{253}$ and one short (2 amino acids) peptide fragment. This analysis confirmed the maize-derived protein amino acid sequence matched that of the microbe-derived aad-1 protein. Results of these analyses indicate that the amino acid sequence of the maize-derived aad-1 protein was equivalent to the *P. fluorescens*-expressed protein.

Example 5.5.1

Tryptic Peptide Fragment Sequencing

In addition to the peptide mass fingerprinting, the amino acid residues at the N- and C-termini of the maize-derived aad-1 protein (immunoaffinity purified from maize event DAS-40278-9) were sequenced and compared to the sequence of the microbe-derived protein. The protein sequences were obtained, by tandem mass spectrometry, for the first 11 residues of the microbe- and maize-derived proteins (Table 8). The amino acid sequences for both proteins were A' H A ALS P LS Q R" (SEQ ID NO:30) showing the N-terminal methionine had been removed by an aminopeptidase (Table 8). The N-terminal aad-1 protein sequence was expected to be M' A HA ALS P LS Q R'$^2$. (SEQ ID NO:31) These results suggest that during or after translation in maize and *P. fluorescens*, the N-terminal methionine is cleaved by a methionine aminopeptidase (MAP). MAPs cleave methionyl residues rapidly when the second residue on the protein is small, such as Gly, Ala, Ser, Cys, Thr, Pro, and Val (Walsh, 2006). In addition to the methionine being removed, a small portion of the N-terminal peptide of the aad-1 protein was shown to have been acetylated after the N-terminal methionine was cleaved (Table 8). This result is encountered frequently with eukaryotic (plant) expressed proteins since approximately 80-90% of the N-terminal residues are modified (Polevoda and Sherman, 2003). Also, it has been shown that proteins with serine and alanine at the N-termini are the most frequently acetylated (Polevoda and Sherman, 2002). The two cotranslational processes, cleavage of N-terminal methionine residue and N-terminal acetylation, are by far the most common modifications and occur on the vast majority (~85%) of eukaryotic proteins (Polevoda and Sherman, 2002). However, examples demonstrating biological significance associated with N-terminal acetylation are rare (Polevoda and Sherman, 2000).

TABLE 8

Summary of N-terminal Sequence Data of AAD-1 Maize- and Microbe-Derived Proteins

| Source | Expected N-terminal Sequence[1] |
|---|---|
| *P. fluorescens* | $M^1$ A H A A L S P L S Q $R^{12}$ (SEQ ID NO: 31) |
| Maize Event DAS-40278-9 | $M^1$ A H A A L S P L S Q $R^{12}$ |

| Source | Expected N-terminal Sequence[2] | Relative[3] Abundance |
|---|---|---|
| *P. fluorescens* | A H A A L S P L S Q $R^{12}$ | 100% |
| Maize Event DAS-40278-9 | A H A A L S P L S Q $R^{12}$ | 31% |
| Maize Event DAS-40278-9 | $^{N-Ac}$A H A A L S P L S Q $R^{12}$ | 3% (SEQ ID NO: 30) |
| Maize Event DAS-40278-9 | H A A L S P L S Q $R^{12}$ | 50% (SEQ ID NO: 32) |
| Maize Event DAS-40278-9 | A A L S P L S Q $R^{12}$ | 6% (SEQ ID NO: 33) |
| Maize Event DAS-40278-9 | A L S P L S Q $R^{12}$ | 12% (SEQ ID NO: 34) |

[1]Expected N-terminal sequence of the first 12 amino acid residues of *P. fluorescens*- and maize- derived AAD-1
[2]Detected N-terminal sequences of *P. fluorescens*- and maize-derived AAD-1.
[3]The tandem MS data for the N-terminal peptides revealed a mixture of AHAALSPLSQR (acetylated) and N-Acetyl-AHAALSPLSQR (acetylated). "Ragged N-terminal ends" were also detected (peptides corresponding to amino acid sequences HAALSPLSQR, AALSPLSQR, and ALSPLSQR). The relative abundance, an estimate of relative peptide fragments quantify, was made based on the corresponding LC peak areas measureed at 214 nm.
Notes:
Numbers in superscript ($R^x$) indicate amino acid residue numbers in the sequence.
Amino acid residue abbreviations:
A: alanine
L: leucine
P: proline
R: arginine
T: threonine
H: histidine
M: methionine
Q: glutamine
S: serine In addition to N-acetylation, there was also slight N-terminal truncation that appeared during purification of the maize-derived aad-1 protein (Table 8). These "ragged-ends" resulted in the loss of amino acids A2, $H^3$ and $A^4$ (in varying forms and amounts) from the maize-derived protein. This truncation is thought to have occurred during the purification of the aad-1 protein as the western blot probe of the crude leaf extracts contained a single crisp band at the same MW as the microbe-derived aad-1 protein. The extraction buffer for the western blotted samples contained an excess of a protease inhibitor cocktail which contains a mixture of protease inhibitors with broad specificity for the inhibition of serine, cysteine, aspartic, and metalloproteases, and aminopeptidases.

The C-terminal sequence of the maize- and microbe-derived aad-1 proteins were determined as described above and compared to the expected amino acid sequences (Table 9). The results indicated the measured sequences were identical to the expected sequences, and both the maize- and microbe-derived aad-1 proteins were identical and unaltered at the C-terminus.

TABLE 9

Summary of C-terminal Sequence Data of AAD-1 Maize- and Microbe-Derived Proteins

| Source | Expected C-terminal Sequence[1] |
|---|---|
| P. fluorescens | $^{287}$TTVGGVRPAR$^{296}$ |
| Maize Event DAS-40278-9 | $^{287}$TTVGGVRPAR$^{296}$ (SEQ ID NO: 35) |

| Source | Detected C-terminal Sequence[2] |
|---|---|
| P. fluorescens | $^{287}$TTVGGVRPAR$^{296}$ |
| Maize Event DAS-40278-9 | $^{287}$TTVGGVRPAR$^{296}$ (SEQ ID NO: 35) |

[1]Expected C-terminal sequence of the last 10 amino acid residues of P. fluorescens- and maize- derived AAD-1.
[2]Detected C-terminal sequences of P. fluorescens- and maize-derived AAD-1.
Notes:
Number is superscript (R$^x$) indicate amino acid residue number in the sequence.
Amino acid residue abbreviations:
A: alanine
P: proline
T: threonine
G: glycine
R: arginine
V: valine Example 6

Field Expression, Nutrient Composition Analysis and Agronomic Characteristics of a Hybrid Maize Line Containing Event DAS-40278-9

The purpose of this study was to determine the levels of AAD-1 protein found in corn tissues. In addition, compositional analysis was performed on corn forage and grain to investigate the equivalency between the isogenic non-transformed corn line and the transgenic corn line DAS-40278-9 (unsprayed, sprayed with 2,4-D, sprayed with quizalofop, and sprayed with 2,4-D and quizalofop). Agronomic characteristics of the isogenic non-transformed corn line were also compared to the DAS-40278-9 corn. The Field expression, composition, and agronomic trials were conducted at six test sites located within the major corn-producing regions of the U.S and Canada. These sites represent regions of diverse agronomic practices and environmental conditions. The trials were located in Iowa, Illinois (2 sites), Indiana, Nebraska and Ontario, Canada.

All site mean values for the control, unsprayed AAD-1, AAD-1+quizalofop, AAD-1+2,4-D and AAD-1+both entry samples were within literature ranges for corn. A limited number of significant differences between unsprayed AAD-1, AAD-1+quizalofop, AAD-1+2,4-D or AAD-1+both corn and the control were observed, but the differences were not considered to be biologically meaningful because they were small and the results were within ranges found for commercial corn. Plots of the composition results do not indicate any biologically-meaningful treatment-related compositional differences among unsprayed AAD-1, AAD-1+quizalofop, AAD-1+2,4-D or AAD-1+both corn and the control corn line. In conclusion, unsprayed AAD-1, AAD-1+quizalofop, AAD-1+2,4-D and AAD-1+both corn composition results confirm equivalence of AAD-1 (Event DAS 40278-9) corn to conventional corn lines.

Example 6.1

Corn Lines Tested

Hybrid seed containing the DAS-40278-9 event and control plants which are conventional hybrid seed of the same genetic background as the test substance line, but do not contain the DAS-40278-9 event, are listed in Table 10.

TABLE 10

| Test Entry | Description |
|---|---|
| 1 | Non-aad-1 Control |
| 2 | aad-1 unsprayed |
| 3 | aad-1 sprayed w/quizalofop |
| 4 | aad-1 sprayed w/2,4-D |
| 5 | aad-1 sprayed w/2,4-D and quizalofop |

The corn plants described above were grown at locations within the major corn growing regions of the U.S. and Canada. The six field testing facilities, Richland, Iowa; Carlyle, Ill.; Wyoming, Ill.; Rockville, Ind.; York, Nebr.; and Branchton, Ontario, Canada (referred to as IA, IL1, IL2, IN, NE and ON) represent regions of diverse agronomic practices and environmental conditions for corn.

The test and control corn seed was planted at a seeding rate of approximately 24 seeds per row with seed spacing within each row of approximately 10 inches (25 cm). At each site, 4 replicate plots of each treatment were established, with each plot consisting of 2-25 ft rows. Plots were arranged in a randomized complete block (RCB) design, with a unique randomization at each site. Each corn plot was bordered by 2 rows of a non-transgenic maize hybrid of similar maturity. The entire trial site was surrounded by a minimum of 12 rows (or 30 ft) of a non-transgenic maize hybrid of similar relative maturity.

Appropriate insect, weed, and disease control practices were applied to produce an agronomically acceptable crop. The monthly maximum and minimum temperatures along with rainfall and irrigation were average for the site. These ranges are typically encountered in corn production.

Example 6.2

Herbicide Applications

Herbicide treatments were applied with a spray volume of approximately 20 gallons per acre (187 L/ha). These applications were designed to replicate maximum label rate commercial practices. Table 11 lists the herbicides that were used.

TABLE 11

| Herbicide | TSN | Concentration |
|---|---|---|
| Weedar 64 | 026491-0006 | 39%, 3.76 lb ae$^a$/gal, 451 g ae/l |
| Assure II | 106155 | 10.2%, 0.87 lb ai$^b$/gal, 104 g ai/l |

$^a$ae = acid equivalent.
$^b$ai = active ingredient.

2,4-D (Weedar 64) was applied as 3 broadcast over-the-top applications to Test Entries 4 and 5 (seasonal total of 3 lb ae/A). Individual applications were at pre-emergence and approximately V4 and V8-V8.5 stages. Individual target application rates were 1.0 lb ac/A for Weedar 64, or 1120 g ae/ha. Actual application rates ranged from 1096-1231 g ae/A.

Quizalofop (Assure II) was applied as a single broadcast over-the-top application to Test Entries 3 and 5. Application timing was at approximately V6 growth stage. The target application rate was 0.0825 lb ai/A for Assurell, or 92 g ai/ha. Actual application rates ranged from 90.8-103 g ai/ha.

Example 6.3

Agronomic Data Collection and Results

Agronomic characteristics were recorded for all test entries within Blocks 2, 3, and 4 at each location. Table 12 lists the following characteristics that were measured.

TABLE 12

| Trait | Evaluation Timing | Description of Data |
|---|---|---|
| Early Population | V1 and V4 | Number of plants emerged per plot. |
| Seedling Vigor | V4 | Visual estimate of average vigor of emerged plants per plot |
| Plant Vigor/Injury | Approximately 1-2 weeks after applications | Injury from herbicide applications. |
| Time to Silking | Approximately 50% Silking | The number of accumulated heat units from the time of planting until approximately 50% of the plants have emerged silks. |
| Time to Pollen Shed | Approximately 50% Pollen shed | The number of accumulated heat units from the time of planting until approximately 50% of the plants are shedding pollen |
| Pollen Viability | Approximately 50% | Evaluation of pollen color and shape over time |
| Plant Height | Approximately R6 | Height to the tip of the tassel |
| Ear Height | Approximately R6 | Height to the base of the primary ear |
| Stalk Lodging | Approximately R6 | Visual estimate of percent of plants in the plot with stalks broken below the primary ear |
| Root Lodging | Approximately R6 | Visual estimate of percent of plants in the plot leaning approximately 30° or more in the first ~½ meter above the soil surface |
| Final Population | Approximately R6 | The number of plants remaining per plot |
| Days to Maturity | Approximately R6 | The number of accumulated heat units from the time of planting until approximately 50% of the plants have reached physiological maturity. |
| Stay Green | Approximately R6 | Overall plant health |
| Disease Incidence | Approximately R6 | Visual estimate of foliar disease incidence |
| Insect Damage | Approximately R6 | Visual estimate of insect damage |

Note:
Heat Unit = ((MAX temp + MIN temp/2) − 50° F.

An analysis of the agronomic data collected from the control, aad-1 unsprayed, aad-1+2,4-D, aad-1+quizalofop, and aad-1+both entries was conducted. For the across-site analysis, no statistically significant differences were observed for early population (V1 and V4), vigor, final population, crop injury, time to silking, time to pollen shed, stalk lodging, root lodging, disease incidence, insect damage, days to maturity, plant height, and pollen viability (shape and color) values in the across location summary analysis (Table 13). For stay green and ear height, significant paired t-tests were observed between the control and the aad-1+quizalofop entries, but were not accompanied by significant overall treatment effects or False Discovery Rates (FDR) adjusted p-values (Table 13).

TABLE 13

Summary Analysis of Agronomic Characteristics Results Across Locations for the DAS-40278-9 aad-1 Corn (Sprayed and Unsprayed) and Control

| Analyte | Overall Trt. Effect (Pr > F)[a] | Control | Unsprayed (P-value,[b] Adj. P)[c] | Sprayed Quizalofop (P-value, Adj. P) | Sprayed 2,4-D (P-value, Adj. P) | Sprayed Both (P-value, Adj. P) |
|---|---|---|---|---|---|---|
| Early population V1 (no. of plants) | (0.351) | 42.8 | 41.3 (0.303, 0.819) | 41.7 (0.443, 8.819) | 41.9 (0.556, 0.819) | 44.1 (0.393, 0.819) |
| Early population V4 (no. of plants) | (0.768) | 43.1 | 43.3 (0.883, 0984) | 43.7 (0.687, 0.863) | 44.3 (0.423, 0.819) | 44.8 (0.263, 0.819) |
| Seedling Vigor[d] | (0.308) | 7.69 | 7.39 (0.197, 0.819) | 7.36 (0.161, 0.819) | 7.58 (0.633, 0.819) | 7.78 (0.729, 0.889) |

TABLE 13-continued

Summary Analysis of Agronomic Characteristics Results Across Locations for the DAS-40278-9 aad-1 Corn (Sprayed and Unsprayed) and Control

| Analyte | Overall Trt. Effect (Pr > F)[a] | Control | Unsprayed (P-value,[b] Adj. P)[c] | Sprayed Quizalofop (P-value, Adj. P) | Sprayed 2,4-D (P-value, Adj. P) | Sprayed Both (P-value, Adj. P) |
|---|---|---|---|---|---|---|
| Final population (number of plants) | (0.873) | 40.1 | 39.6 (0.747, 0.889) | 39.7 (0.802, 0.924) | 39.9 (0.943, 1.00) | 41.1 (0.521, 0.819) |
| Crop Injury-1st app.[e] | NA[l] | 0 | 0 | 0 | 0 | 0 |
| Crop Injury-2nd app.[e] | (0.431) | 0 | 0 (1.00, 1.00) | 0 (1.00, 1.00) | 0 (1.00, 1.00) | 0.28 (0.130, 0.819) |
| Crop Injury-3rd app.[e] | NA | 0 | 0 | 0 | 0 | 0 |
| Crop Injury-4th app.[e] | NA | 0 | 0 | 0 | 0 | 0 |
| Time to Silking (heat units)[f] | (0.294) | 1291 | 1291 (0.996, 1.00) | 1293 (0.781, 0.917) | 1304 (0.088, 0.819) | 1300 (0.224, 0.819) |
| Time to Pollen shed (heat units)[f] | (0.331) | 1336 | 1331 (0.564, 0.819) | 1342 (0.480, 0.819) | 1347 (0.245, 0.819) | 1347 (0.245, 0.819) |
| Pollen Shape 0 minutes (%)[g] | (0.872) | 10.9 | 10.9 (0.931, 1.00) | 11.3 (0.546, 0.819) | 11.4 (0.439, 0.819) | 11.3 (0.605, 0.819) |
| Pollen Shape 30 minutes (%) | (0.486) | 49.2 | 50.8 (0.618, 0.819) | 46.4 (0.409, 0.819) | 48.1 (0.739, 0.889) | 51.9 (0.409, 0.819) |
| Pollen Shape 60 minutes (%) | (0.724) | 74.4 | 74.7 (0.809, 0.924) | 73.6 (0.470, 0819) | 73.9 (0.629, 0.819) | 75.0 (0.629, 0.819) |
| Pollen Shape 120 minutes (%) | (0.816) | 82.6 | 82.6 (1.00, 1.00) | 82.6 (1.00, 1.00) | 82.6 (1.00, 1.00) | 82.5 (0.337, 0.819) |
| Pollen Color 30 minutes (%) | (0.524) | 51.9 | 52.5 (0.850, 0.960) | 48.9 (0.306, 0.819) | 50.3 (0.573, 0.819) | 53.6 (0.573, 0.819) |
| Pollen Color 60 minutes (%) | (0.32) | 75.3 | 75.9 (0.612, 0.819) | 74.2 (0.315, 0.819) | 74.2 (0.315, 0.819) | 75.9 (0.612, 0.819) |
| Pollen Color 120 minutes (%) | NA | 84.0 | 84.0 | 84.0 | 84.0 | 84.0 |
| Stalk Lodging (%) | (0.261) | 5.11 | 5.22 (0.356, 0.819) | 5.00 (0.356, 0.819) | 5.00 (0.356, 0.819) | 5.00 (0.356, 0.819) |
| Root Lodging (%) | (0.431) | 0.44 | 0.17 (0.457, 0.819) | 0.72 (0.457, 0.819) | 0.17 (0.457, 0.819) | 0.11 (0.373, 0.819) |
| Stay Green[i] | (0.260) | 4.67 | 4.28 (0.250, 0.819) | 3.92 (0.034[m], 0.819) | 4.17 (0.144, 0.819) | 4.11 (0.106, 0.819) |
| Disease Incidence[j] | (0.741) | 6.42 | 6.22 (0.383, 0.819) | 6.17 (0.265, 0.819) | 6.17 (0.265, 0.819) | 6.17 (0.265, 0.819) |
| Insect Damage[k] | (0.627) | 7.67 | 7.78 (0.500, 0.819) | 7.78 (0.0500, 0.819) | 7.72 (0.736, 0.889) | 7.56 (0.500, 0.819) |
| Days to Maturity (heat units)[f] | (04.87) | 2411 | 2413 (0.558, 0819) | 2415 ((0.302, 0.819) | 2416 (0.185, 0.819) | 2417 (0.104, 0.819) |
| Plant Height (cm) | (0.676) | 294 | 290 (0.206, 0.819) | 290 (0.209, 0.819) | 291 (0.350, 0.819) | 291 (0.286, 0.819) |
| Ear Height (cm) | (0.089) | 124 | 120 (0.089, 0.819) | 118 (0.018[m], 0.786) | 121 (0.214, 0.819) | 118 (0.016[m], 0.786) |

[a]Overall treatment effect estimated using an F-test.
[b]Comparison of the sprayed and unsprayed treatments to the control using a t-test.
[c]P-values adjusted using a False Discovery Rate (FDR) procedure.
[d]Visual estimate on 1-9 scale; 9 = tall plants with large robust leaves.
[e]0-100% scale; with 0 = no injury and 100 = dead plant.
[f]The number of heat units that have accumulated from the time of planting.
[g]0-100% scale; with % pollen grains with collapsed walls.
[h]0-100% scale; with % pollen grains with intense yellow color.
[i]Visual estimate on 1-9 scale with 1 no visible green tissue.
[j]Visual estimate on 1-9 scale with 1 being poor disease resistance.
[k]Visual estimate on 1-9 scale with 1 being poor insect resistance.
[l]NA = statistical analysis not performed since no variability across replicate or treatment.
[m]Statistical difference indicated by P-Value <0.05.

Example 6.4

Sample Collection

Samples for expression and composition analysis were collected as listed in Table 14.

TABLE 14

| Block | Tissue | Approx. Growth Stage[a] | Sample Size | Samples per Entry Control Entry 1 | Test Entries 2-5 |
|---|---|---|---|---|---|
| 1 (expression) | Leaf | V2-4 | 3 leaves | 3 | 3 |
|  | Leaf | V9 | 3 leaves | 3 | 3 |
|  | Pollen[b] | R1 | 1 plant | 3 | 3 |
|  | Root[b] | R1 | 1 plant | 3 | 3 |
|  | Leaf[b] | R1 | 1 leaf | 3 | 3 |
|  | Forage | R4 | 2 plants[c] | 3 | 3 |
|  | Whole Plant | R6 | 2 plants[c] 1 | 3 | 3 |
|  | Grain | R6-Maturity | ear | 3 | 3 |

| Block | Tissue | Growth Stage[a] | Sample Size | Control Entry 1 | Test Entries 2-5 |
|---|---|---|---|---|---|
| 2-4 (composition) | Forage | R4 | 3 plants[c] | 1 | 1 |
|  | Grain | R6-Maturity | 5 ears | 1 | 1 |

[a] Approximate growth stage.
[b] The pollen, root, and leaf samples collected at R1 collected from the same plant.
[c] Two plants chopped, combined and sub-sampled for expression, or 3 plants for composition

Example 6.5

Determination of Aad-1 Protein in Corn Samples

Samples of corn were analyzed for the amount of aad-1 protein. Soluble extractable aad-1 protein is quantified using an enzyme-linked immunosorbent assay (ELISA) kit purchased from Beacon Analytical System, Inc. (Portland, Me.).

Samples of corn tissues were isolated from the test plants and prepared for expression analysis by coarse grinding, lyophilizing and fine-grinding (if necessary) with a Geno/Grinder (Certiprep, Metuchen, N.J.). No additional preparation was required for pollen. The aad-1 protein was extracted from corn tissues with a phosphate buffered saline solution containing the detergent Tween-20 (PBST) containing 0.5% Bovine Serum Albumin (BSA). For pollen, the protein was extracted with a 0.5% PBST/BSA buffer containing 1 mg/mL of sodium ascorbate and 2% protease inhibitor cocktail. The plant tissue and pollen extracts were centrifuged; the aqueous supernatant was collected, diluted with appropriate buffer if necessary, and analyzed using an aad-1 ELISA kit in a sandwich format. The kit used the following steps. An aliquot of the diluted sample and a biotinylated anti-aad-1 monoclonal antibody are incubated in the wells of a microtiter plate coated with an immobilized anti-aad-1 monoclonal antibody. These antibodies bind with aad-1 protein in the wells and form a "sandwich" with aad-1 protein bound between soluble and the immobilized antibody. The unbound samples and conjugate are then removed from the plate by washing with PBST. An excess amount of streptavidin-enzyme (alkaline phosphatase) conjugate is added to the wells for incubation. At the end of the incubation period, the unbound reagents were removed from the plate by washing. Subsequent addition of an enzyme substrate generated a colored product. Since the aad-1 was bound in the antibody sandwich, the level of color development was related to the concentration of aad-1 in the sample (i.e., lower residue concentrations result in lower color development). The absorbance at 405 nm was measured using a Molecular Devices V-max or Spectra Max 190 plate reader. A calibration curve was generated and the aad-1 concentration in unknown samples was calculated from the polynomial regression equation using Soft-MAX Pro™ software which was compatible with the plate reader. Samples were analyzed in duplicate wells with the average concentration of the duplicate wells being reported.

A summary of the aad-1 protein concentrations (averaged across sites) in the various corn matrices is shown in Table 15. aad-1 average protein concentration ranged from 2.87 ng/mg dry weight in R1 stage root to 127 ng/mg in pollen. Expression results for the unsprayed and sprayed plots were similar. The aad-1 protein was not detected in any control samples, with the exception of one control root sample from the Indiana site.

TABLE 15

Summary of Mean Concentration Levels of aad-1 Protein Measured in the aad-1Unsprayed, aad-1 + Quizalofop, aad-1 + 2,4-D and aad-1 + Quizalofop and 2,4-D in Maize Tissues

| Corn Tissue | Treatment | AAD-1 ng/mg Tissue Dry Weight Mean | Std. Dev. | Range |
|---|---|---|---|---|
| V2-V4 Leaf | AAD-1 Unsprayed | 13.4 | 8.00 | 1.98-29.9 |
|  | AAD-1 + Quizalofop | 13.3 | 6.89 | 4.75-24.5 |
|  | AAD-1 + 2,4-D | 14.2 | 7.16 | 4.98-26.7 |
|  | AAD-1_Quizalofop and 2,4-D | 12.3 | 7.09 | 4.07-22.5 |
| V9 Leaf | AAD-1 Unsprayed | 5.96 | 2.50 | 2.67-10.9 |
|  | AAD-1 + Quizalofop | 5.38 | 1.84 | 2.52-9.15 |
|  | AAD-1 + 2,4-D | 6.37 | 2.41 | 3.03-10.9 |
|  | AAD-1_Quizalofop and 2,4-D | 6.52 | 2.38 | 3.11-11.1 |
| R1 Leaf | AAD-1 Unsprayed | 5.57 | 1.66 | 3.47-9.34 |
|  | AAD-1 + Quizalofop | 5.70 | 1.63 | 2.70-7.78 |
|  | AAD-1 + 2,4-D | 5.99 | 1.90 | 2.40-9.42 |
|  | AAD-1_Quizalofop and 2,4-D | 6.06 | 2.27 | 1.55-10.2 |
| Pollen | AAD-1 Unsprayed | 127 | 36.2 | 56.3-210 |
|  | AAD-1 + Quizalofop | 108 | 29.9 | 52.2-146 |
|  | AAD-1 + 2,4-D | 113 | 30.2 | 37.5-137 |
|  | AAD-1_Quizalofop and 2,4-D | 112 | 32.6 | 45.4-162 |
| R1 Root | AAD-1 Unsprayed | 2.92 | 1.87 | 0.42-6.10 |
|  | AAD-1 + Quizalofop | 3.09 | 1.80 | 0.56-6.06 |
|  | AAD-1 + 2,4-D | 3.92 | 2.03 | 0.91-7.62 |
|  | AAD-1_Quizalofop and 2,4-D | 2.87 | 1.23 | 1.09-5.56 |
| R4 Forage | AAD-1 Unsprayed | 6.87 | 2.79 | 2.37-12.1 |
|  | AAD-1 + Quizalofop | 7.16 | 2.84 | 3.05-11.6 |
|  | AAD-1 + 2,4-D | 7.32 | 2.46 | 2.36-10.6 |
|  | AAD-1_Quizalofop and 2,4-D | 6.84 | 2.31 | 2.25-10.3 |
| Whole plant | AAD-1 Unsprayed | 4.53 | 2.55 | 0.78-8.88 |
|  | AAD-1 + Quizalofop | 4.61 | 2.22 | 0.75-8.77 |
|  | AAD-1 + 2,4-D | 5.16 | 2.53 | 0.83-10.2 |
|  | AAD-1_Quizalofop and 2,4-D | 4.55 | 1.77 | 1.30-8.21 |
| Grain | AAD-1 Unsprayed | 5.00 | 1.53 | 2.66-8.36 |
|  | AAD-1 + Quizalofop | 4.63 | 1.51 | 1.07-6.84 |
|  | AAD-1 + 2,4-D | 4.98 | 1.78 | 2.94-9.10 |
|  | AAD-1_Quizalofop and 2,4-D | 4.61 | 1.62 | 1.81-7.49 |

[a] ND—value less than the method Limit Of Detection (LOD)
[b] Values in parentheses are between the method LOD and Limit Of quantitation (LOQ).

Example 6.6

Compositional Analysis

Samples of corn forage and grain were analyzed at for nutrient content with a variety of tests. The analyses performed for forage included ash, total fat, moisture, protein, carbohydrate, crude fiber, acid detergent fiber, neutral detergent fiber, calcium and phosphorus. The analyses performed for grain included proximates (ash, total fat, moisture, protein, carbohydrate, crude fiber, acid detergent fiber), neutral detergent fiber (NDF), minerals, amino acids, fatty acids, vitamins, secondary metabolites and anti-nutrients. The results of the nutritional analysis for corn forage and grain were compared with values reported in literature (see; Watson, 1982 (4); Watson, 1984 (5); ILSI Crop Composition Database, 2006 (6); OECD Consensus Document on Compositional Considerations for maize, 2002 (7); and Codex Alimentarius Commission 2001 (8)).

the control, but a significant overall treatment effect was not observed. For carbohydrates, a statistically significant overall treatment effect, paired t-test and FDR adjusted p-value was observed between the aad-1+quizalofop and the control. Also for carbohydrates, a significant paired t-test for the unsprayed aad-1 entry was observed, but without a significant FDR adjusted p-value. These differences are not biologically meaningful since all across-site results for these analytes were within the reported literature ranges for corn, and differences from the control were small (<23%).

TABLE 16

Summary of the Proximate, Fiber and Mineral Analysis of Corn Forage from All Sites.

| Proximate (% dry weight) | Literature Values[a] | Overall Treatment Effect (Pr > F)[b] | Control | Unsprayed (P-value[c] Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Protein | 3.14-15.9 | (0.054) | 7.65 | 6.51 (0.016[e], 0.066) | 6.41 (0.010[e], 0.051) | 7.17 (0.285, 0.450) | 7.13 (0.245, 0.402) |
| Fat | 0.296-6.7 | (0.068) | 2.29 | 2.08 (0.202, 0.357) | 1.78 (0.005[e], 0.028[e]) | 2.10 (0.233, 0.391) | 2.01 (0.093, 0.213) |
| Ash | 1.3-10.5 | (0.072) | 3.90 | 3.84 (0.742, 0.859) | 4.03 (0.525, 0.708) | 3.99 (0.673, 0.799) | 4.40 (0.019[e], 0.069) |
| Moisture | 53.3-87.5 | (0.819) | 69.5 | 69.2 (0.651, 0.782) | 69.5 (0.988, 0.988) | 69.8 (0.699, 0.820) | 70.0 (0.501, 0.687) |
| Carbohydrates | 66.9-94.5 | (0.026[e]) | 86.1 | 87.6 (0.015[e], 0.061) | 87.8 (0.006[e], 0.034[e]) | 86.8 (0.262, 0.424) | 86.5 (0.538, 0.708) |
| Fiber (% dry weight) | | | | | | | |
| Acid Detergent Fiber (ADF) | 16.1-47.4 | (0.968) | 26.5 | 26.6 (0.925, 0.970) | 26.8 (0.833, 0.925) | 26.0 (0.677, 0.800) | 26.8 (0.851, 0.937) |
| Neutral Detergent Fiber (NDF) | 20.3-63.7 | (0.345) | 41.6 | 43.6 (0.169, 0.322) | 43.3 (0.242, 0.402) | 41.3 (0.809, 0.911) | 41.6 (0.978, 0.985) |
| Minerals (% dry weight) | | | | | | | |
| Calcium | 0.071-0.6 | (0.321) | 0.212 | 0.203 (0.532, 0.708) | 0.210 (0.930, 0.970) | 0.215 (0.815, 0.911) | 0.231 (0.150, 0.296) |
| Phosphorus | 0.094-0.55 | (0.163) | 0.197 | 0.189 (0.198, 0.354) | 0.202 (0.427, 0.615) | 0.203 (0.288, 0.450) | 0.200 (0.608, 0.762) |

[a]Combined range.
[b]Overall treatment effect estimated using an F-test.
[c]Comparison of the transgenic treatments to the control using t-tests.
[d]P-values adjusted using a False Discovery Rate (FDR) procedure.
[e]Statistical difference indicated by P-value <0.05.

Example 6.6.1

Proximate, Fiber and Mineral Analysis of Forage

An analysis of the protein, fat, ash, moisture, carbohydrate, ADF, NDF, calcium and phosphorus in corn forage samples from the control, unsprayed aad-1, aad-1+quizalofop, aad-1+2,4-D and aad-1+both entries was performed. A summary of the results across all locations is shown in Table 16. For the across-site and individual-site analysis, all proximate, fiber and mineral mean values were within literature ranges. No statistical differences were observed in the across-site analysis between the control and transgenic entries for moisture, ADF, NDF, calcium and phosphorus. For protein and ash, significant paired t-tests were observed for the unsprayed AAD-1 (protein), the aad-1+quizalofop (protein), and aad-1+both (ash), but were not accompanied by significant overall treatment effects or FDR adjusted p-values. For fat, both a significant paired t-test and adjusted p-value was observed for aad-1+quizalofop compared with Example 6.6.2

Proximate and Fiber Analysis of Grain

A summary of the results for proximates (protein, fat, ash, moisture, cholesterol and carbohydrates) and fiber (ADF, NDF and total dietary fiber) in corn grain across all locations is shown in Table 17. All results for proximates and fiber were within literature ranges, and no significant differences in the across-site analysis were observed between the control and transgenic entries for fat, ash, NDF and total dietary fiber. For moisture, a significant overall treatment effect was observed, but not accompanied by significant paired t-tests or FDR adjusted p-values. For ADF, a significant paired t-test was observed for aad-1+both, but no significant overall treatment effect or FDR adjusted p-value was seen. For both protein and carbohydrates, significant pair-tests, adjusted p-values and overall treatment effects were found for the unsprayed aad-1, aad-1+quizalofop, and aad-1+both. Since these differences were small (<12%) and all values were within literature ranges, the differences are not considered biologically meaningful.

TABLE 17

Summary of the Proximate and Fiber Analysis of Corn Grain from All Sites.

| Proximate (% dry weight) | Literature Values[a] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Protein | 6-17.3 | (0.003[e]) | 9.97 | 10.9 (0.002[e], 0.016[e]) | 11.1 (0.0004[e], 0.013[e]) | 10.5 (0.061, 0.161) | 10.9 (0.002[e], 0.015[e]) |
| Fat | 1.2-18.8 | (0.369) | 4.26 | 4.19 (0.238, 0.397) | 4.16 (0.095, 0.215) | 4.26 (0.955, 0.977) | 4.22 (0.427, 0.615) |
| Ash | 0.62-6.28 | (0.553) | 1.45 | 1.55 (0.178, 0.330) | 1.52 (0.364, 0.557) | 1.45 (0.982, 0.985) | 1.51 (0.397, 0.587) |
| Moisture | 6.1-40.5 | (0.038[e]) | 25.1 | 25.5 (0.406, 0.594) | 24.4 (0.056, 0.152) | 24.5 (0.117, 0.254) | 24.5 (0.114, 0.250) |
| Cholesterol | NR[f] | NA[g] | <LOQ | <LOQ | <LOQ | <LOQ | <LOQ |
| Carbohydrate | 63.3-89.8 | (0.005[e]) | 84.3 | 83.3 (0.002[e], 0.015[e])) | 83.2 (0.001[e], 0.013[e]) | 83.8 (0.074, 0.185) | 83.4 (0.003[e], 0.019[e]) |
| Fiber (% dry weight) | | | | | | | |
| Acid Detergent Fiber (ADF) | 1.82-11.3 | (0.247) | 4.23 | 3.94 (0.130, 0.269) | 3.99 (0.197, 0.354) | 3.89 (0.078, 0.193) | 3.82 (0.035[e], 0.106) |
| Neutral Detergent Fiber (NDF) | 5.59-22.6 | (0.442) | 10.6 | 10.3 (0.455, 0.638) | 9.89 (0.120, 0.254) | 9.90 (0.121, 0.254) | 10.3 (0.552, 0.708) |
| Total Dietary Fiber | 8.3-35.3 | (0.579) | 13.4 | 12.8 (0.164, 0.313) | 12.9 (0.195, 0.353) | 13.1 (0.487, 0.679) | 12.9 (0.215, 0.370) |

[a] Combined range
[b] Overall treatment effect estimated using an F-test.
[c] comparison of the transgenic treatments to the control using t-tests.
[d] P-values adjusted using a False Discovery Rate (FDR) procedure.
[e] Statistical difference indicated by P-Value <0.05.
[f] NR = not reported.
[g] NA = statistical analysis was snot performed since a majority of the data was <LOQ.

Example 6.6.3

Mineral Analysis of Grain

An analysis of corn grain samples for the minerals calcium, chromium, copper, iodine, iron, magnesium, manganese, molybdenum, phosphorus, potassium, selenium, sodium, and zinc was performed. A summary of the results across all locations is shown in Table 18. All results were within the reported literature ranges. For the across-site analysis, no significant differences were observed for calcium, copper, iron, and potassium. Mean results for chromium, iodine, selenium and sodium were below the limit of quantitation of the method. For magnesium and phosphorus, significant paired t-tests were observed for the unsprayed aad-1 and the aad-1+quizalof op entries, but were not accompanied by significant overall treatment effects or FDR adjusted p-values. For manganese and molybdenum, a significant paired t-test was observed for the unsprayed aad-1, but a significant FDR adjusted p-value and overall treatment effect was not found. For the aad-1+both entry, a significant paired t-test was observed for zinc, but a significant FDR adjusted p-value or overall treatment effect was not present. Additionally, these differences from the control were small (<13%), and all values were within literature ranges, when available.

TABLE 18

Summary of the Mineral Analysis of Corn Grain from All Sites.

| Minerals (mg/100 g dry wt.) | Literature Values[a] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Calcium | 1.27-100 | (0.493) | 4.05 | 4.21 (0.146, 0.289) | 4.12 (0.505, 0.687) | 4.04 (0.944, 0977) | 4.06 (0898, 0.957) |
| Chromium | 0.006-0.016 | NA[e] | <LOQ | <LOQ | <LOQ | <LOQ | <LOQ |
| Copper | 0073-1.85 | (0963) | 0.144 | 0.151 (0.655, 0.782) | 0.146 (0.890, 0.957) | 0.141 (0.817, 0.911) | 0.149 (0.749, 0863) |
| Iodine | 7.3-81 | NA | <LOQ | <LOQ | <LOQ | <LOQ | <LOQ |
| Iron | 0.1-10 | (0.333) | 2.49 | 2.60 (0.086, 0.206) | 2.56 (0.310, 0.482) | 2.51 (0.801, 0.911) | 2.59 (0.145, 0.289) |
| Magnesium | 59.4-1000 | (0.072) | 122 | 129 (0.010[f], 0.051) | 128 (0.017[f], 0.066) | 126 (0.145, 0.289) | 127 (0.070, 0.177) |
| Manganese | 0.07-5.4 | (0.099) | 0.525 | 0.551 (0.025[f], 0.082) | 0.524 (0.884, 0.957) | 0.526 (0.942, 0.977) | 0.532 (0.505, 0.687) |
| Molybdenum | NR | (0.143) | 261 | 229 (0.020[f], 0.072) | 236 (0.067, 0.173) | 244 (0.206, 0.362) | 234 (0.046, 0.132) |

TABLE 18-continued

Summary of the Mineral Analysis of Corn Grain from All Sites.

| Minerals (mg/100 g dry wt.) | Literature Values[a] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Phosphorus | 147-750 | (0.102) | 289 | 303 (0.012[f], 0.057) | 300 (0.035[f], 0.106) | 299 (0.055, 0.150) | 298 (0.085, 0.206) |
| Potassium | 181-720 | (0.453) | 362 | 368 (0.330, 0.510) | 359 (0.655, 0.782) | 364 (0.722, 0.839) | 357 (0.454, 0.638) |
| Selenium | 0.001-01 | NA | <LOQ | <LOQ | <LOQ | <LOQ | <LOQ |
| Sodium | 0-150 | NA | <LOQ | <LOQ | <LOQ | <LOQ | <LOQ |
| Zinc | 0.65-3.72 | (0.166) | 2.26 | 2.32 (0.183, 0.336) | 2.34 (0.108, 0.238) | 2.29 (0.627, 0.768) | 2.37 (0.027[f], 0.085) |

[a]Combined range.
[b]Overall treatment effect estimated using an F-test.
[c]Comparison of the transgenic treatments to the control using t-tests.
[d]P-values adjusted using a False Discovery Rate (FDR) procedure
[e]NA = statistical analyusis was not performed since a majority fo the data was <LOQ.
[f]Statistical difference indicated by P-value <0.05.

Example 6.6.4

Amino Acid Analysis of Grain

Corn samples were analyzed for amino acid content in the control, unsprayed aad-1, aad-1+quizalofop, aad-1+2,4-D and aad-1+both corn, and a summary of the results over all locations and by individual field site are shown in Table 19. Levels of all amino acids were within the reported literature ranges, and no significant differences in the across-site analysis were observed for arginine, lysine, and tyrosine. Significant differences were observed for several of the amino acids in the across-site analysis. In these instances, the amino acid content of the control was lower than the aad-1 transgenic lines, which may be related to the overall lower protein content in the control grain compared with the aad-1 lines. For the unsprayed aad-1 entry, significant overall treatment effects along with significant paired t-tests and FDR adjusted p-values were found for all amino acids except arginine, glycine, lysine, tryptophan and tyrosine. For the aad-1+quizalofop entry, significant overall treatment effects along with significant paired t-tests and FDR adjusted p-values were found for all amino acids except arginine, cysteine, glycine, lysine, tryptophan and tyrosine. For the aad-1+2,4-D entry, significant overall treatment effects along with significant paired t-tests (with significant FDR adjusted p-values) were found for all amino acids except arginine, aspartic acid, glycine, histidine, lysine, tyrosine and valine. For the aad-1+both entry, significant overall treatment effects along with significant paired t-tests and FDR adjusted p-values were found for all amino acids except arginine, glycine, lysine, serine, tryptophan and tyrosine. Although there were many differences observed for amino acids, the differences were small (<15%), not observed across all sites, and all mean values were within reported literature ranges.

TABLE 19

Summary of the Amino Acid Analysis of Corn Grain from All Sites.

| Amino Acids (% dry wt.) | Literature Values[a] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Alanine | 0.44-1.39 | (0.002[e]) | 0.806 | 0.901 (0.0005[e], 0.013[e]) | 0.900 (0.005[e], 0.013[e]) | 0.863 (0.021[e], 0.074) | 0.894 (0.001[e], 0.013[e]) |
| Arginine | 0.12-0.64 | (0.371) | 0486 | 0.499 (0.286, 0.450) | 0.505 (0.139, 0.283) | 0.487 (0.929, 0.970) | 0.484 (0.897, 0.957) |
| Aspartic Acid | 0.34-1.21 | (0.010[e]) | 0.712 | 0.768 (0.002[e], 0.015[e]) | 0.764 (0.003[e], 0.021) | 0.743 (0.060, 0.160) | 0.762 (0.004[e], 0.027[e]) |
| Cysteine | 0.08-0.51 | (0.033[e]) | 0.213 | 0.225 (0.009[e], 0.050[e]) | 0.223 (0.020[e], 0.072) | 0.223 (0.018[e], 0.067) | 0.226 (0.005[e], 0.028[e]) |
| Glutamic Acid | 0.97-3.54 | (0.001[e]) | 1.97 | 2.22 (0.0003[e], 0.013[e]) | 2.21 (0.0004, 0.013[e]) | 2.12 (0.017[e], 0.067) | 2.20 (0.001[e], 0.013[e]) |
| Glycine | 0.18-0.54 | (0.052) | 0.383 | 0.397 (0.018[e], 0.067) | 0.398 (0.013[e], 0.059) | 0.390 (0.217, 0.371) | 0.397 (0.016[e], 0.066) |
| Histidine | 0.14-0.43 | (0.005[e]) | 0.283 | 0.303 (0.001[e], 0.013[e]) | 0.302 (0.002[e], 0.014[e]) | 0.295 (0.036, 0.109) | 0.302 (0.002[e], 0.014[e]) |
| Isoleucine | 0.18-0.71 | (0.003[e]) | 0.386 | 0.427 (0.001[e], 0.014[e]) | 0.427 (0.001[e], 0.014[e]) | 0.410 (0.044[e], 0127) | 0.431 (0.001[e], 0.013[e]) |
| Leucine | 0.64-2.49 | (0.001[e]) | 1.35 | 1.54 (0.0003[e], 0.013[e]) | 1.54 (0.003[e], 0.013[e]) | 1.47 (0.013[e], 0.059) | 1.53 (0.001[e], 0.013[e]) |
| Lysine | 0.05-056 | (0.211) | 0.310 | 0.315 (0.210, 0.367) | 0.316 (0.128, 0.265) | 0.309 (0.879, 0.956) | 0.316 (0.102, 0.226) |

TABLE 19-continued

Summary of the Amino Acid Analysis of Corn Grain from All Sites.

| Amino Acids (% dry wt.) | Literature Values[a] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Methionine | 0.10-0.47 | (0.003[e]) | 0.195 | 0.209 (0.001[e], 0.013[e]) | 0.209 (0.001[e], 0.013[e]) | 0.205 (0.014[e], 0.061) | 0.208 (0.001[e], 0.014[e]) |
| Phenylalanine | 0.24-0.93 | (0.002[e]) | 0551 | 0.617 (0.001[e], 0.013[e]) | 0.619 (0.001[e], 0.013[e]) | 0.592 (0.023[e], 0.077) | 0.615 (0.001[e], 0.013[e]) |
| Proline | 0.46-1.63 | (0.002[e]) | 0.910 | 1.01 (0.0004[e], 0.013[e]) | 1.01 (0.001[e], 0.013[e]) | 0.975 (0.012[e], 0.059) | 0.997 (0.001[e], 0.014[e]) |
| Serine | 0.24-0.91 | (0.009[e]) | 0.498 | 0.550 (0.002[e], 0.014[e]) | 0.550 (0.001[e], 0.014[e]) | 0.529 (0.042[e], 0.122) | 0.536 (0.015[e], 0.061) |
| Threonine | 0.22-0.67 | (0.005[e]) | 0.364 | 0394 (0.001[e], 0.014[e]) | 0394 (0.001[e], 0.013[e]) | 0.384 (0.023[e], 0.077) | 0.390 (0.003[e], 0.020[e]) |
| Tryptophan | 0.03-0.22 | 0.088) | 0.052 | 0.055 (0.067, 0.173) | 0.056 (0.025[e], 0.082) | 0.056 (0.014[e], 0.060) | 0.056 (0.029[e], 0.092) |
| Tyrosine | 0.10-0.79 | (0.390) | 0.336 | 0.355 (0.535, 0.708) | 0.375 (0.214, 0.370) | 0.339 (0.907, 0.964) | 0.314 (0.500, 0.687) |
| Valine | 0.21-0.86 | (0.005[e]) | 0.495 | 0.537 (0.002[e], 0.014[e]) | 0.538 (0.002[e], 0.014[e]) | 0.519 (0.054, 0.148) | 0.538 (0.001[e], 0.014) |

[a]Combined range.
[b]Overall treatment effect estimated using an F-test.
[c]Comparison of the transgenic treatments to the control using t-tests.
[d]P-values adjusted using a False Discovery Rate (FDR) procedure
[e]Statistical difference indicated by P-value <0.05.

Example 6.6.5

Fatty Acid Analysis of Grain

An analysis of corn grain samples for fatty acids was performed. A summary of the results across all locations is shown in Table 20. All results for the control, unsprayed aad-1, aad-1+quizalofop, aad-1+2,4-D and aad-1+both corn grain samples analyzed for these fatty acids were within the published literature ranges. Results for caprylic (8:0), capric (10:0), lauric (12:0), myristic (14:0), myristoleic (14:1), pentadecanoic (15:0), pentadecenoic (15:1), heptadecanoic (17:0), heptadecanoic (17:1), gamma linolenic (18:3), eicosadienoic (20:2), eicosatrienoic (20:3), and arachidonic (20:4) were below the method Limit of Quantitation (LOQ). In the across-site analysis, no significant differences were observed for 16:0 palmitic, 16:1 pamitoleic, 18:0 stearic, 18:2 linoleic, 18:3 linolenic, and 20:0 arachidic. For 18:1 oleic and 20:1 eicosenoic, significant paired t-tests were observed for the unsprayed aad-1 (18:1) and the aad-1+2, 4-D (18:1 and 20:1) entries, but were not accompanied by significant overall treatment effects or FDR adjusted p-values. For 22:0 behenic, a significant overall treatment effect and significant paired t-tests for aad-1+2,4-D and aad-1+both were found, but significant FDR adjusted p-values were not present.

TABLE 20

Summary of the Fatty Acid Analysis of Corn Grain from All Sites.

| Fatty Acids (% total fatty acids)[a] | Literature Values[b] | Overall Treatment Effect (Pr > F)[c] | Control | Unsprayed (P-value[d], Adj. P)[e] | Sprayed Quizalofop (P-value, Adj. P) | Sprayed 2,4-D (P-value, Adj. P) | Sprayed Both (P-value, Adj. P) |
|---|---|---|---|---|---|---|---|
| 8:0 Caparylic | 0.13-0.34 | NA[f] | <LOQ | <LOQ | <LOQ | <LOQ | <LOQ |
| 10:0 Capric | ND | NA | <LOQ | <LOQ | <LOQ | <LOQ | <LOQ |
| 12:0 Lauric | ND-0.687 | NA | <LOQ | <LOQ | <LOQ | <LOQ | <LOQ |
| 14:0 Myristic | ND-0.3 | NA | <LOQ | <LOQ | <LOQ | <LOQ | <LOQ |
| 14.1 Myristoleic | NR | NA | <LOQ | <LOQ | <LOQ | <LOQ | <LOQ |
| 15:0 Pentadecanoic | NR | NA | <LOQ | <LOQ | <LOQ | <LOQ | <LOQ |
| 15:1 Pentadecenoic | NR | NA | <LOQ | <LOQ | <LOQ | <LOQ | <LOQ |
| 16:0 Palmitic | 7-20.7 | (0.559) | 9.83 | 9.88 (0.618, 0.763) | 9.95 (0.280, 0.445) | 9.78 (0.617, 0.763) | 9.90 (0.544, 0.708) |
| 16:1 Palmitoleic | ND-1.0 | (0.552) | 0.056 | 0.044 (0.804, 0.911) | 0.047 (0.551, 0.708) | 0.041 (0.555, 0.708) | 0.079 (0.392, 0.582) |
| 17:0 Heptadecanoic | ND-0.11 | NA | <LOQ | <LOQ | <LOQ | <LOQ | <LOQ |
| 17:1 Heptadecenoic | ND-0.1 | NA | <LOQ | <LOQ | <LOQ | <LOQ | <LOQ |
| 18:0 Stearic | ND-3.4 | (0.561) | 2.04 | 1.98 (0.119, 0.254) | 2.01 (0.437, 0.626) | 2.00 (0.259, 0.421) | 2.02 (0.598, 0.756) |
| 18:1 Oleic | 17.4-46 | (0.076) | 31.3 | 30.4 (0.013[g], 0.059) | 30.8 (0.178, 0.329) | 30.4 (0.015[g], 0.061) | 30.7 (0092, 0.213) |
| 18:2 Linoleic | 34.0-70 | (0.474) | 47.5 | 48.3 (0.189, 0.345) | 48.4 (0.144, 0.289) | 48.0 (0.453, 0.638) | 48.5 (0.119, 0.254) |
| 18:3 Gamma Linolenic | NR | NA | <LOQ | <LOQ | <LOQ | <LOQ | <LOQ |

TABLE 20-continued

Summary of the Fatty Acid Analysis of Corn Grain from All Sites.

| Fatty Acids (% total fatty acids)[a] | Literature Values[b] | Overall Treatment Effect (Pr > F)[c] | Control | Unsprayed (P-value[d], Adj. P)[e] | Sprayed Quizalofop (P-value, Adj. P) | Sprayed 2,4-D (P-value, Adj. P) | Sprayed Both (P-value, Adj. P) |
|---|---|---|---|---|---|---|---|
| 18:3 Linoleic | ND-2.25 | (0.479) | 1.04 | 1.05 (0.537, 0.708) | 1.06 (0.202, 0.357) | 1.04 (0.842, 0.932) | 1.06 (0.266, 0.428) |
| 20:4 Arachidonic | 0.1-2 | (0.379) | 0.400 | 0.386 (0.061, 0.161) | 0.393 (0.341, 0.525) | 0.390 (0.153, 0.297) | 0.390 (0.175, 0.328) |
| 20:1 Eicosenoic | 0.17-1.92 | (0.107) | 0.232 | 0.226 (0.089, 0.210) | 0.230 (0.497, 0.687) | 0.223 (.013[g], 0.059) | 0.227 (0.121, 0.254) |
| 20:2 Eicosadienoic | ND-0.53 | NA | <LOQ | <LOQ | <LOQ | <LOQ | <LOQ |
| 20:3 Eicosatrienoic | 0.275 | NA | <LOQ | <LOQ | <LOQ | <LOQ | <LOQ |
| 20:4 Arachidonic | 0.465 | NA | <LOQ | <LOQ | <LOQ | <LOQ | <LOQ |
| 22:0 Behemic | ND-0.5 | (0.044[g]) | 0.136 | 0.088 (0.093, 0.213) | 0.076 (0.887, 0.957) | 0.086 (0011[g], 0.054) | 0.108 (0.023[g], 0.077) |

[a]Results converted from unites of % dry weight to % fatty acids.
[b]Combined range.
[c]Overall treatment effect estimated using an F-test.
[d]Comparison of the transgenic treatments to the control using t-tests.
[e]P-values adjusted using a False Discovery rate (FDR) procedure.
[f]NA = statistical analysis was not performed since a majority of the data was <LOQ.
[g]Statistical difference indicated by P-value <0.05.

Example 6.6.6

Vitamin Analysis of Grain

The levels of vitamin A, B1, B2, B5, B6, B12, C, D, E, niacin, and folic acid in corn grain samples from the control, unsprayed aad-1, aad-1+quizalofop, aad-1+2,4-D and aad-1+both corn entries were determined. A summary of the results across all locations is shown in Table 21. Vitamins B12, D and E were not quantifiable by the analytical methods used. All mean results reported for vitamins were similar to reported literature values, when available. Results for the vitamins without reported literature ranges (vitamins B5 and C) were similar to control values obtained (<22% difference from control). For the across-site analysis, no statistical differences were observed, with the exception of vitamins B1, C and niacin. Significant paired t-tests for Vitamins B1 were observed between the control and unsprayed aad-1, aad-1+quizalofop, and aad-1+both, but were not accompanied by significant overall treatment effects or FDR adjusted p-values. For vitamin C, a significant overall treatment effect was observed along with significant paired t-tests and FDR adjusted p-values for aad-1+quizalofop and aad-1+2,4-D. Similarly for niacin, a significant overall treatment effect was observed along with significant paired t-tests and FDR adjusted p-values for aad-1+quizalofop and aad-1+both. A significant paired t-test for the aad-1+2,4-D was also found for niacin for the aad-1+2,4-D entry, but was not accompanied by a significant overall treatment effect or FDR adjusted p-value. Since the differences were not observed across sites and values were within literature ranges (when available), the differences are not considered biologically meaningful.

TABLE 21

Summary of Vitamin Analysis of Corn Grain from All Sites.

| Vitamins (mg/kg dry weight) | Literature Values[b] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Beta Carotene (Vitamin A) | 0.19-46.8 | (0.649) | 1.80 | 1.85 (0.372, 0.566) | 1.80 (0.967, 0.983) | 1.82 (0770, 0.883) | 1.87 (0.221, 0.376) |
| Vitam B1 (Thiamin) | 1.3-40 | (0.068) | 3.47 | 3.63 (00.041[e], 0.121) | 3.67 (0.013[e], 0.059) | 3.54 (0.375, 0.567) | 3.64 (0.032[e], 0.100) |
| Vitamin B2 (Riboflavin) | 0.25-5.6 | (0.803) | 2.15 | 2.05 (0.443, 0.631) | 2.08 (0.600, 0.756) | 1.99 (0.227, 0.383) | 2.07 (0.543, 0.708) |
| Vitamin B5 (Pantothenic acid) | NR[f] | (0.820) | 5.28 | 5.17 (0.623, 0.766) | 5.09 (0.391, 0.582) | 5.29 (0.968, 0.983) | 5.10 (0.424, 0.615) |
| Vitamin B6 (Pyridoxine) | 3.68-11.3 | (0.431) | 6.52 | 6.57 (0.859, 0.938) | 6.66 (0.652, 0.782) | 6.66 (0.652, 0.782) | 7.08 (0.088, 0.210) |
| Vitamin B12 | NR | NA[g] | <LOQ | <LOQ | <LOQ | <LOQ | <LOQ |
| Vitamin C | NR | (0.018[e]) | 22.4 | 21.2 (0.268, 0.429) | 17.5 (0.005[e], 0.028[e]) | 18.0 (0.004[e], 0.026[e]) | 20.4 (0.068, 0.173) |
| Vitamin D | NR | NA | <LOQ | <LOQ | <LOQ | <LOQ | <LOQ |
| Vitamin E (alpha Tocopherol) | 1.5-68.7 | (0.558) | <LOQ | <LOQ | <LOQ | <LOQ | <LOQ |

TABLE 21-continued

Summary of Vitamin Analysis of Corn Grain from All Sites.

| Vitamins (mg/kg dry weight) | Literature Values[b] | Overall Treatment Effect (Pr > F)[b] | Control | Unsprayed (P-value[c], Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Niacin (Nicotinic acid, Vit. B3) | 9.3-70 | (0.013[e]) | 26.1 | 24.2 (0.050, 0.140) | 22.9 (0.002[e], 0.017[e]) | 23.7 (0.018[e], 0.067) | 22.9 (0.002[e], 0.016[e]) |
| Folic Acid | 0.15-683 | (0.881) | 0.594 | 0.588 (0.779, 0.890) | 0.574 (0.403, 0.592) | 0.592 (0.931, 0.970) | 0.597 (0.916, 0.970) |

[a]Combined range.
[b]Overall treatment effect estimated using an F-test.
[c]comparison of the transgenic treatments to the control using t-tests.
[d]P-values adjusted using a False Discovery Rate (FDR) procedure.
[e]Statistical difference indicated by P-value <0.05.
[f]NR = not reported.
[g]NA = statistical analysis was not performed since a majority of the data was <LOQ.

Example 6.6.7

Anti-Nutrient and Secondary Metabolite Analysis of Grain

The secondary metabolite (coumaric acid, ferulic acid, furfural and inositol) and anti-nutrient (phytic acid, raffinose, and trypsin inhibitor) levels in corn grain samples from the control, unsprayed aad-1, aad-1+quizalofop, aad-1+2,4-D and aad-1+both corn entries were determined. A summary of the results across all locations is shown in Table 22 and 23. For the across-site analysis, all values were within literature ranges. No significant differences between the aad-1 entries and the control entry results were observed in the across-site analysis for inositol and trypsin inhibitor. Results for furfural and raffinose were below the method's limit of quantitation. Significant paired t-tests were observed for coumaric acid (unsprayed aad-1, aad-1+2,4-D and aad-1+both), and ferulic acid (aad-1+quizalofop and aad-1+both). These differences were not accompanied by significant overall treatment effects or FDR adjusted p-values and were similar to the control (<10% difference). A significant overall treatment effect, paired t-test, and FDR adjusted p-value was found for phytic acid (unsprayed aad-1). Since all results were within literature ranges and similar to the control (<11% difference), these differences are not considered to be biologically meaningful.

TABLE 22

Summary of Secondary Metabolite Analysis of Corn Grain from All Sites.

| Secondary Metabolite (% dry weight) | Literature Values[a] | Overall Treatment Effect, (Pr > F)[b] | Control | Unsprayed (P-value,[c] Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Coumaric Acid | 0.003-0.058 | (0.119) | 0.021 | 0.020 (0.038[e], 0.113) | 0.020 (0.090, 0.211) | 0.019 (0.022[e], 0.074) | 0.020 (0.029[e], 0.091) |
| Ferulic Acid | 0.02-0.389 | (0.077) | 0.208 | 0.199 (0.051, 0.141) | 0.196 (0.010[e], 0.051) | 0.200 (0.080, 0.196) | 0.197 (0.019[e], 0.069) |
| Furfural | 0.0003-0.0006 | NA[f] | <LOQ | <LOQ | <LOQ | <LOQ | <LOQ |
| Inositol | 0.0089-0.377 | (0.734) | 0.218 | 0.224 (0.548, 0.708) | 0.218 (0.973, 0.984) | 0.213 (0.612, 0.763) | 0.211 (0.526, 0.708) |

[a]Combined range.
[b]Overall treatment effect estimated using an F-test.
[c]Comparison of the transgenic treatments control using t-tests.
[d]P-values adjusted using a False Discovery Rate (FDR) procedure.
[e]Statistical difference indicated by P-Value <0.05.
[f]NA = statistical analysis was not performed since a majority of the data was <LOQ.

TABLE 23

Summary of Anti-Nutrient Analysis of Corn Grain from All Sites.

| Anti-Nutrient (% dry weight) | Literature Values[a] | Overall Treatment Effect (Pr > F)[b] | Control | Unsprayed (P-value,[c] Adj. P)[d] | Sprayed Quizalofop (P-value, Adj. P) | Sprayed 2,4-D (P-value, Adj. P) | Sprayed Both (P-value, Adj. P) |
|---|---|---|---|---|---|---|---|
| Phytic Acid | 0.11-1.57 | (0.046[e]) | 0.727 | 0.806 (0.003[e], 0.020[e]) | 0.767 (0.099, 0.224) | 0.755 (0.245, 0.402) | 0.761 (0.158, 0.304) |
| Raffinose | 0.02-0.32 | NA[f] | <LOQ | <LOQ | <LOQ | <LOQ | <LOQ |
| Trypsin Inhibitor (TIU/mg) | 1.09-7.18 | (0.742) | 5.08 | 5.10 (0.954, 0.977) | 4.87 (0.631, 0.770) | 5.45 (0.387, 0.582) | 5.18 (0.813, 0.911) |

[a]Combined range
[b]Overall treatment effect estimated using an F-test.
[c]Comparison of the transgenic treatments to the control using t-tests.
[d]P-values adjusted using a False Discovery Rate (FDR) procedure.
[e]Statistical difference indicated by P-Value <0.05.
[f]NA = statistical analysis was not performed since a majority of the data was <LOQ.

Example 7

Additional Agronomic Trials

Agronomic characteristics of corn line 40278 compared to a near-isoline corn line were evaluated across diverse environments. Treatments included 4 genetically distinct hybrids and their appropriate near-isoline control hybrids tested across a total of 21 locations.

The four test hybrids were medium to late maturity hybrids ranging from 99 to 113 day relative maturity. Experiment A tested event DAS-40278-9 in the genetic background Inbred C x BC3S1 conversion. This hybrid has a relative maturity of 109 days and was tested at 16 locations (Table 24). Experiment B tested the hybrid background Inbred E x BC3S1 conversion, a 113 day relative maturity hybrid. This hybrid was tested at 14 locations, using a slightly different set of locations than Experiment A (Table 24). Experiments C and D tested hybrid backgrounds BC2S1 conversion x Inbred D and BC2S1 conversion x Inbred F, respectively. Both of these hybrids have a 99 day relative maturity and were tested at the same 10 locations.

TABLE 24

Locations of agronomic trials

| Location | Experiment | | | |
|---|---|---|---|---|
| | 2A | 2B | 2C | 2D |
| Atlantic, IA | X | X | | |
| Fort Dodge, IA | X | X | X | X |
| Huxley, IA | X | X | X | X |
| Nora Springs, IA | X | | | |
| Wyman, IA | X | X | | |
| Lincoln, IL | | X | | |
| Pontiac, IL | X | X | X | X |
| Princeton, IL | X | X | | |
| Seymour, IL | X | | | |
| Shannon, IL | X | | X | X |
| Viola, IL | X | X | | |
| Bremen, IN | X | X | X | X |
| Evansville, IN | | X | | |
| Fowler, IN | X | X | X | X |
| Mt. Vernon, IN | | X | | |
| Olivia, MN | | | X | X |
| Wayne, NE | X | X | | |
| York, NE | X | X | | |

TABLE 24-continued

Locations of agronomic trials

| Location | Experiment | | | |
|---|---|---|---|---|
| | 2A | 2B | 2C | 2D |
| Arlington, WI | X | | X | X |
| Patteville, WI | X | | X | X |
| Watertown, WI | | | X | X |

For each trial, a randomized complete block design was used with two replications per location and two row plots. Row length was 20 feet and each row was seeded at 34 seeds per row. Standard regional agronomic practices were used in the management of the trials.

Data were collected and analyzed for eight agronomic characteristics; plant height, ear height, stalk lodging, root lodging, final population, grain moisture, test weight, and yield. The parameters plant height and ear height provide information about the appearance of the hybrids. The agronomic characteristics of percent stalk lodging and root lodging determine the harvestability of a hybrid. Final population count measures seed quality and seasonal growing conditions that affect yield. Percent grain moisture at harvest defines the maturity of the hybrid, and yield (bushels/acre adjusted for moisture) and test weight (weight in pounds of a bushel of corn adjusted to 15.5% moisture) describe the reproductive capability of the hybrid.

Analysis of variance was conducted across the field sites using a linear model. Entry and location were included in the model as fixed effects. Mixed models including location and location by entry as random effects were explored, but location by entry explained only a small portion of variance and its variance component was often not significantly different from zero. For stock and root lodging a logarithmic transformation was used to stabilize the variance, however means and ranges are reported on the original scale. Significant differences were declared at the 95% confidence level. The significance of an overall treatment effect was estimated using a t-test.

Results from these agronomic characterization trials can be found in Table 25. No statistically significant differences were found for any of the four 40278 hybrids compared to the isoline controls (at $p<0.05$) for the parameters of ear height, stalk lodging, root lodging, grain moisture, test weight, and yield. Final population count and plant height were statistically different in Experiments A and B, respectively, but similar differences were not seen in comparisons with the other 40278 hybrids tested. Some of the variation seen may be due to low levels of genetic variability remaining from the backcrossing of the DAS-40278-9 event into the elite inbred lines. The overall range of values for the measured parameters are all within the range of values obtained for traditional corn hybrids and would not lead to a conclusion of increased weediness. In summary, agronomic characterization data indicate that 40278 corn is biologically equivalent to conventional corn.

TABLE 25

Analysis of agronomic characteristics

| Parameter (units) | Treatment | Mean | Range Min | Range Max | P-value |
|---|---|---|---|---|---|
| Experiment A | | | | | |
| Plant Height (inches) | AAD-1 | 96.31 | 94.00 | 99.00 | 0.6174 |
| | Control | 95.41 | 95.00 | 98.00 | |
| Ear Height (inches) | AAD-1 | 41.08 | 30.00 | 48.00 | 0.4538 |
| | Control | 44.42 | 40.00 | 47.00 | |
| Stalk Lodging (%) | AAD-1 | 3.64 | 0.00 | 27.70 | 0.2020 |
| | Control | 2.49 | 0.00 | 28.57 | |
| Root Lodging (%) | AAD-1 | 1.00 | 0.00 | 7.81 | 0.7658 |
| | Control | 0.89 | 0.00 | 28.33 | |
| Final Population (plants/acre in 1000's) | AAD-1 | 31.06 | 27.00 | 36.00 | 0.0230 |
| | Control | 32.17 | 27.00 | 36.00 | |
| Grain Moisture (%) | AAD-1 | 22.10 | 14.32 | 27.80 | 0.5132 |
| | Control | 21.84 | 14.52 | 31.00 | |
| Test Weight (lb/bushel) | AAD-1 | 54.94 | 51.10 | 56.80 | 0.4123 |
| | Control | 54.66 | 51.00 | 56.80 | |
| Yield (bushels/acre) | AAD-1 | 193.50 | 138.85 | 229.38 | 0.9712 |
| | Control | 187.05 | 99.87 | 256.72 | |
| Experiment B | | | | | |
| Plant Height (inches) | AAD-1 | 106.92 | 104.00 | 108.00 | 0.0178 |
| | Control | 100.79 | 95.00 | 104.00 | |
| Ear Height (inches) | AAD-1 | 51.75 | 49.00 | 50.00 | 0.1552 |
| | Control | 45.63 | 38.00 | 50.00 | |
| Stalk Lodging (%) | AAD-1 | 1.24 | 0.00 | 15.07 | 0.1513 |
| | Control | 0.72 | 0.00 | 22.22 | |
| Root Lodging (%) | AAD-1 | 0.64 | 0.00 | 6.15 | 0.2498 |
| | Control | 0.40 | 0.00 | 9.09 | |
| Final Population (plants/acre in 1000's) | AAD-1 | 31.30 | 26.00 | 37.00 | 0.4001 |
| | Control | 30.98 | 25.00 | 35.00 | |
| Grain Moisture (%) | AAD-1 | 23.71 | 14.34 | 28.70 | 0.9869 |
| | Control | 23.72 | 13.39 | 31.10 | |
| Test Weight (lb/bushel) | AAD-1 | 56.96 | 50.90 | 59.50 | 0.2796 |
| | Control | 56.67 | 52.00 | 60.10 | |
| Yield (bushels/acre) | AAD-1 | 200.08 | 102.32 | 258.36 | 0.2031 |
| | Control | 205.41 | 95.35 | 259.03 | |
| Experiment C | | | | | |
| Plant Height (inches) | AAD-1 | 95.92 | 94.00 | 96.00 | 0.1262 |
| | Control | 90.92 | 90.00 | 90.00 | |
| Ear Height (inches) | AAD-1 | 47.75 | 41.00 | 50.00 | 0.4630 |
| | Control | 43.75 | 37.00 | 46.00 | |
| Stalk Lodging (%) | AAD-1 | 6.74 | 0.00 | 27.47 | 0.4964 |
| | Control | 5.46 | 0.00 | 28.12 | |
| Root Lodging (%) | AAD-1 | 0.3512 | 0.00 | 7.58 | 0.8783 |
| | Control | 0.3077 | 0.00 | 33.33 | |
| Final Population (plants/acre in 1000's) | AAD-1 | 32.78 | 29.00 | 36.00 | 0.0543 |
| | Control | 31.68 | 24.00 | 35.00 | |
| Grain Moisture (%) | AAD-1 | 19.09 | 13.33 | 25.90 | 0.5706 |
| | Control | 19.36 | 13.66 | 26.50 | |
| Test Weight (lb/bushel) | AAD-1 | 54.62 | 42.10 | 58.80 | 0.1715 |
| | Control | 55.14 | 52.80 | 58.40 | |
| Yield (bushels/acre) | AAD-1 | 192.48 | 135.96 | 243.89 | 0.2218 |
| | Control | 200.35 | 129.02 | 285.58 | |
| Experiment D | | | | | |
| Stalk Lodging (%) | AAD-1 | 7.29 | 0.00 | 9.26 | 0.4364 |
| | Control | 4.17 | 0.00 | 39.06 | |
| Final Population (plants/acre in 1000's) | AAD-1 | 29.93 | 27.00 | 34.00 | 0.0571 |
| | Control | 31.86 | 29.00 | 35.00 | |
| Grain Moisture (%) | AAD-1 | 18.74 | 19.40 | 24.40 | 0.4716 |
| | Control | 19.32 | 13.35 | 25.70 | |
| Test Weight (lb/bushel) | AAD-1 | 56.59 | 54.80 | 58.30 | 0.0992 |
| | Control | 55.50 | 52.70 | 57.40 | |
| Yield (bushels/acre) | AAD-1 | 203.55 | 196.51 | 240.17 | 0.7370 |
| | Control | 199.82 | 118.56 | 264.11 | |

Example 8

Use of Corn Event DAS-40278-9 Insertion Site for Targeted Integration

Consistent agronomic performance of the transgene of corn event DAS-40278-9 over several generations under field conditions suggests that these identified regions around the corn event DAS-40278-9 insertion site provide good genomic locations for the targeted integration of other transgenic genes of interest. Such targeted integration overcomes the problems with so-called "position effect," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the disclosed teaching, a skilled person is able to target polynucleic acids of interest to the same insertion site on chromosome 2 as that in corn event DAS-40278-9 or to a site in close proximity to the insertion site in corn event DAS-40278-9. One such method is disclosed in International Patent Application No. WO2008/021207, herein incorporated by reference in its entirety.

Briefly, up to 20 Kb of the genomic sequence flanking 5' to the insertion site and up to 20 Kb of the genomic sequence flanking 3' to the insertion site (portions of which are identified with reference to SEQ ID NO:29) are used to flank the gene or genes of interest that are intended to be inserted into a genomic location on chromosome 2 via homologous recombination. The gene or genes of interest can be placed exactly as in the corn event DAS-40278-9 insertion site or can be placed anywhere within the 20 Kb regions around the corn event DAS-40278-9 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the donor DNA vector into the corn event DAS-40278-9 target site can be further enhanced by one of the several methods, including but not limited to the co-expression or up-regulation of recombination enhancing genes or down-regulation of endogenous recombination suppression genes. Furthermore, it is known in the art that double-stranded cleavage of specific sequences in the genome can be used to increase homologous recombination frequency, therefore insertion into the corn event DAS-40278-9 insertion site and its flanking regions can be enhanced by expression of natural or designed sequence-specific endonucleases for cleaving these sequences. Thus, using the teaching provided herein, any heterologous nucleic acid can be inserted on corn chromosome 2 at a target site located between a 5' molecular marker discussed in Example 4 and a 3' molecular marker discussed in Example 4, preferably within SEQ ID NO:29, and/or regions thereof as discussed elsewhere herein.

Example 9

Excision of the Pat Gene Expression Cassette from Corn Event DAS-40278-9

The removal of a selectable marker gene expression cassette is advantageous for targeted insertion into the genomic loci of corn event DAS-40278-9. The removal of the pat selectable marker from corn event DAS-40278-9 allows for the re-use of the pat selectable marker in targeted integration of polynucleic acids into chromosome 4 in subsequent generations of corn.

Using the disclosed teaching, a skilled person is able to excise polynucleic acids of interest from corn event DAS-40278-9. One such method is disclosed in Provisional U.S. Patent Application No. 61/297,628, herein incorporated by reference in its entirety.

Briefly, sequence-specific endonucleases such as zinc finger nucleases are designed which recognize, bind and cleave specific DNA sequences that flank a gene expression cassette. The zinc finger nucleases are delivered into the plant cell by crossing a parent plant which contains transgenic zinc finger nuclease expression cassettes to a second parent plant which contains corn event DAS-40278-9. The resulting progeny are grown to maturity and analyzed for the loss of the pat expression cassette via leaf painting with a herbicide which contains glufosinate. Progeny plants which are not resistant to the herbicide are confirmed molecularly and advanced for self-fertilization. The excision and removal of the pat expression cassette is molecularly confirmed in the progeny obtained from the self-fertilization. Using the teaching provided herein, any heterologous nucleic acid can be excised from corn chromosome 2 at a target site located between a 5' molecular marker and a 3' molecular marker as discussed in Example 4, preferably within SEQ ID NO:29 or the indicated regions thereof.

Example 10

Resistance to Brittlesnap

Brittlesnap refers to breakage of corn stalks by high winds following applications of growth regulator herbicides, usually during periods of fast growth. Mechanical "push" tests, which use a bar to physically push the corn to simulate damage due to high winds, were performed on hybrid corn containing event DAS-40278-9 and control plants not containing event DAS-40278-9. The treatments were completed at four different geographical locations and were replicated four times (there was an exception for one trial which was only replicated three times). The plots consisted of eight rows: four rows of each of the two hybrids, with two rows containing event DAS-40278-9 and two rows without the event. Each row was twenty feet in length. Corn plants were grown to the V4 developmental stage, and a commercial herbicide containing 2,4-D (Weedar 64, Nufarm Inc., Burr Ridge, Ill.) was applied at rates of 1120 g ac/ha, 2240 g ae/ha and 4480 g ae/ha. Seven days after application of the herbicide, a mechanical push test was performed. The mechanical push test for brittlesnap consisted of pulling a 4-foot bar down the two rows of corn to simulate wind damage. Height of the bar and speed of travel were set to provide a low level of stalk breakage (10% or less) with untreated plants to ensure a test severe enough to demonstrate a difference between treatments. The directionality of the brittlesnap treatment was applied against leaning corn.

Two of the trial locations experienced high winds and thunderstorms 2-3 days after application of the 2,4-D herbicide. On two consecutive days, a thunderstorm commenced in Huxley Iowa. Wind speeds of 2 to 17 m s$^{-1}$ with high speeds of 33 m s$^{-1}$ were reported at the site of the field plot. The wind direction was variable. On one day, a thunderstorm was reported in Lanesboro Minn. Winds of high velocity were reported at the site of this field plot. In addition, both storms produced rain. The combination of rain and wind attributed to the reported brittlesnap damage.

Assessments of the brittlesnap damage which resulted from the mechanical push test (and inclement weather) were made by visually rating the percentage of injury. Prior to the mechanical brittlesnap bar treatment, plant stand counts were made for the hybrid corn containing event DAS-40278-9 and controls. Several days after the brittlesnap bar treatment the plot stand counts were reassessed. The percentage of leaning and percentage of reduced stand within the plot was determined (Table 26). The data from the trials demonstrated that hybrid corn containing event DAS-40278-9 has less propensity for brittlesnap as compared to the null plants following an application of 2,4-D.

TABLE 26

DAS-40278-9 Corn Brittlesnap Tolerance to V4 Application of 2,4-D Amine. The percentage of brittlesnap was calculated for hybrid corn plants containing event DAS-40278-9 and compared to control plants which do not contain the event.

| Treatment | 278 (SL B01-278//4X P811XTR) | Null (SLB01//4XP811XTR) | 278 (SLB01VX-278/BE9515XT) | Null (SLB01VX//BE9515XT) |
|---|---|---|---|---|
| | Before Mechanical Snapping Mean$^3$ % Leaning 7-8 Days After Application$^1$ | | | |
| Weedar 64 1120 g ac/ha | 0% | 38% | 0% | 33% |
| Weedar 64 2240 g ac/ha | 1% | 42% | 0% | 33% |

TABLE 26-continued

DAS-40278-9 Corn Brittlesnap Tolerance to V4 Application of 2,4-D Amine. The percentage of brittlesnap was calculated for hybrid corn plants containing event DAS-40278-9 and compared to control plants which do not contain the event.

| Treatment | 278 (SL B01-278//4X P811XTR) | Null (SLB01//4XP811XTR) | 278 (SLB01VX-278/BE9515XT) | Null (SLB01VX//BE9515XT) |
|---|---|---|---|---|
| Weedar 64 4480 g ac/ha | 2% | 55% | 1% | 46% |
| Untreated | 0% | 0% | 0% | 0% |
| After Mechanical Snapping Mean[3] % Leaning 11-14 Days After Application | | | | |
| Weedar 64 1120 g ac/ha | 0% | 19% | 1% | 24% |
| Weedar 64 2240 g ac/ha | 4% | 30% | 7% | 27% |
| Weedar 64 4480 g ac/ha | 4% | 26% | 6% | 28% |
| Untreated | 0% | 0% | 0% | 0% |
| After Mechanical Snapping Mean[3] % Stand Reduction 11-14 Days After Application | | | | |
| Weedar 64 1120 g ac/ha | 3% | 38% | 6% | 42% |
| Weedar 64 2240 g ac/ha | 9% | 35% | 12% | 41% |
| Weedar 64 4480 g ac/ha | 9% | 40% | 16% | 40% |
| Untreated | 0% | 0% | 0% | 0% |

[1] Thunderstorm and high winds occurred 2-3 days after application in two trials
[2] Treatments replicated four times in a randomized complete block design (one trial was only completed for three replications
[3] Means corrected for occurrences in untreated (untreated means forced to zero)

Example 11

Protein Analysis of Grain

Grain with increased total protein content was produced from hybrid corn containing event DAS-40278-9 as compared to control plants not containing the event. Two consecutive multisite field trails were conducted that included non-sprayed and herbicide-treatments with three different herbicide combinations. In 7 of the 8 statistical comparisons, the DAS-40278-9 event produced grain with significantly higher total protein content (Table 27). This data is corroborated by analyses of individual amino acids.

TABLE 27

Protein content of grain from multisite field trials

| 2008 Field Season | Non-transgenic Near-isoline | Event DAS-40278-9 unsprayed | Event DAS-40278-9 quizalofop | Event DAS-40278-9 2,4-D | Event DAS-40278-9 quizalofop and 2,4-D |
|---|---|---|---|---|---|
| Mean | 9.97 | 10.9 | 11.1 | 10.5 | 10.9 |
| % increase over isoline | 0 | 9.3 | 11.3 | 5.3 | 9.3 |
| Paired t-test | NA | 0.0002 | 0.0004 | 0.061 | 0.002 |
| Mean | 10.9 | 11.6 | 11.7 | 11.7 | 11.5 |
| % increase over isoline | 0 | 6.4 | 7.3 | 7.2 | 5.5 |
| Paired t-test | NA | 0.0048 | 0.001 | 0.0012 | 0.0079 |

Example 12

Additional Agronomic Trials

Agronomic characteristics of hybrid corn containing event DAS-40278-9 compared to near-isoline corn were collected from multiple field trials across diverse geographic environments for a growing season. The data were collected and analyzed for agronomic characteristics as described in Example 7. The results for hybrid corn lines containing event DAS-40278-9 as compared to null plants are listed in Table 28. Additionally, agronomic characteristics for the hybrid corn lines containing event DAS-40278-9 and null plants sprayed with the herbicides quizalofop (280 g ae/ha) at the V3 stage of development and 2,4-D (2,240 g ae/ha) sprayed at the V6 stage of development are described in Table 29.

TABLE 28 yield, percent moisture, and final population results for hybrid corn containing event DAS-40278-9 as compared to the near-isoline control.

| Name | Yield | Grain Moisture (%) | Final Population (plants/acre Reported in 1000's) |
| --- | --- | --- | --- |
| Hybrid Corn Containing DAS-40278-9 | 218.1 | 21.59 | 31.69 |
| Control Hybrid Corn | 217.4 | 21.91 | 30.42 |

TABLE 29 yield, percent moisture, percentage stock lodging, percentage root lodging and total population for hybrid corn lines containing event DAS-40278-9 as compared to the near-isoline control.

| Trial | Yield | Grain Moisture (%) | Stock Lodge (%) | Root Lodge (%) | Final Population (plants/acre reported in 1000's) |
| --- | --- | --- | --- | --- | --- |
| Spray Trial | | | | | |
| Hybrid Corn #1 Containing DAS-40278-9 | 214.9 | 23.4 | 0.61 | 2.19 | 30 |
| Control Hybrid Corn #1 | 177.9 | 23.46 | 0.97 | 36.32 | 28.36 |
| LSD (0.5) | 13.3 | 1.107 | 0.89 | 10.7 | 1.1 |
| Non Spray | | | | | |
| Hybrid Corn #1 Containing DAS-40278-9 | 219.6 | 22.3 | 0.95 | 1.78 | 30.8 |
| Control Hybrid Corn #1 | 220.3 | 22.51 | 0.54 | 1.52 | 30.55 |
| LSD (0.5) | 6.9 | 0.358 | 0.98 | 1.65 | 0.7 |
| Spray Trial | | | | | |
| Hybrid Corn #2 Containing DAS-40278-9 | 198.6 | 26.76 | 0.38 | 2.08 | 29.29 |
| Control Hybrid Corn #2 | 172.3 | 23.76 | 1.5 | 39.16 | 28.86 |
| LSD (0.5) | 13.3 | 1.107 | 0.89 | 10.7 | 1.1 |
| Non Spray | | | | | |
| Hybrid Corn #2 Containing DAS-40278-9 | 207.8 | 24.34 | 0.22 | 0.59 | 31 |
| Control Hybrid Corn #2 | 206.2 | 24.88 | 0.35 | 0.12 | 30.94 |
| LSD (0.5) | 8.0 | 0.645 | 0.55 | 1.79 | 0.9 |

The invention claimed is:

1. A plant part of a transgenic corn plant, said part comprising a recombinant nucleic acid consisting of SEQ ID NO: 29 located in said plant's genome, wherein said corn plant's genome comprises a nucleic acid consisting of residues 1874-6689 of SEQ ID NO: 29 inserted between said plant's genomic sequences comprising residues 1-1873 of SEQ ID NO:29 and residues 6690-8557 of SEQ ID NO:29 to produce said recombinant nucleic acid consisting of SEQ ID NO: 29.

* * * * *